United States Patent [19]
Jacobs, Jr. et al.

[11] Patent Number: 6,015,890
[45] Date of Patent: Jan. 18, 2000

[54] EMBCAB OPERON OF MYCOBACTERIA AND MUTANTS THEREOF

[75] Inventors: William R. Jacobs, Jr., City Island, N.Y.; James M. Musser, Bellaire, Tex.; Amalio Telenti, Burgistein, Switzerland

[73] Assignee: Albert Einstein College of Medicine of Yeshiva University, Bronx, N.Y.

[21] Appl. No.: 08/822,586

[22] Filed: Mar. 20, 1997

[51] Int. Cl.⁷ .......................... C07H 21/04; C07H 21/02; C12Q 1/68; C12P 19/34
[52] U.S. Cl. .......................... 536/23.7; 435/6; 435/91.1; 435/863; 536/23.1; 536/24.32
[58] Field of Search ............................... 435/6, 91.1, 863; 536/23.1, 23.7, 24.32; 935/77

[56] References Cited

PUBLICATIONS

Belanger et al, "The embAB genes of Mycobacterium avium encode an arabinosyl transferase involved in cell wall arabinan biosynthesis that is the target for the antimycobacterial drug ethambutol", Proc. Natl. Acad. Sci. USA, vol. 93, pp. 11919–11924, Oct. 1, 1996.

Telenti et al, Mycobacterium smegmatis ethambutol resistance region: EmbC (embC) gene, partial cds, EmbA (emba) and embB (embG) genes, complete cds., direct submission to GenBank data base, accession No. U46844, Feb. 20, 1996.

*Primary Examiner*—James C. Housel
*Assistant Examiner*—Rodney P. Swartz
*Attorney, Agent, or Firm*—Amster, Rothstein & Ebenstein

[57] ABSTRACT

This invention relates to the identification, cloning, sequencing and characterization of the embCAB operon which determines mycobacterial resistance to the antimycobacterial drug ethambutol. The embCAB operon encodes the proteins which are the target of action of *Mycobacterium tuberculosis, Mycobacterium smegmatis*, and *Mycobacterium leprae* for ethambutol. The present invention provides purified and isolated embC, embA, and embB nucleic acids which comprise the embCAB operon, as well as mutated forms of these nucleic acids. The present invention also provides one or more single-stranded nucleic acid probes which specifically hybridize to the wild type embCAB operon or the mutated embCAB operon, and mixtures thereof, which may be formulated in kits, and used in the diagnosis of drug-resistant mycobacterial strain. The present invention also provides methods for the treatment and prevention of mycobacterial infections. In addition, the probes of the present invention may be used to determine the susceptibility of mycobacteria to ethambutol.

10 Claims, 25 Drawing Sheets

FIG. 1A

```
   1  GCGGCTGGCC CAGGACGTCT ACCCCAACCA GCCCAATGTT CGCCGCTACA CGGTGGACCT
      CGCCGACCGG GTCCTGCAGA TGGGGTTGGT CGGGTTACAA GCGGCGATGT GCCACCTGGA

61  ACGGACCGCC CTCTTCGCCG ACCCGCGTTT CGTCGTCGAG GACATTGGCC CGTTCGTGCT
      TGCCTGGCGG GAGAAGCGGC TGGGCGCAAA GCAGCAGCTC CTGTAACCGG GCAAGCACGA

121  GGCCATCCGC AAGCCGCAGG AGAGCGCGTG ATGGCTACCG AAGCCGCCCC ACCCCGTATC
      CCGGTAGGCG TTCGGCGTCC TCTCGCGCAC TACCGATGGC TTCGGCGGGG TGGGGCATAG

181  GCCGTCCGGC TACCATCTAC CTCCGTGCGC GACGCGGGAG CAAACTACCG GATCGCCCGG
      CGGCAGGCCG ATGGTAGATG GAGGCACGCG CTGCGCCCTC GTTTGATGGC CTAGCGGGCC

241  TACGTCGCTG TGGTGGCGGG TCTGCTAGGC GCTGTGCTGG CCATCGCCAC CCCACTGCTG
      ATGCAGCGAC ACCACCGCCC AGACGATCCG CGACACGACC GGTAGCGGTG GGGTGACGAC

301  CCGGTCAACC AGACCACCGC GCAATTGAAC TGGCCCCAAA ACGGACGTT CGCCAGTGTC
      GGCCAGTTGG TCTGGTGGCG CGTTAACTTG ACCGGGGTTT TGCCGTGCAA GCGGTCACAG

361  GAGGCACCGC TGATTGGCTA CGTGGCCACC GACTTGAACA TCACCGTCCC CTGCCAGGCC
      CTCCGTGGCG ACTAACCGAT GCACCGGTGG CTGAACTTGT AGTGGCAGGG GACGGTCCGG

421  GCCGCCGGAC TGGCCGGATC GCAGAACACC GGCAAGACGG TGTTGTTGTC AACGGTGCCC
      CGGCGGCCTG ACCGGCCTAG CGTCTTGTGG CCGTTCTGCC ACAACAACAG TTGCCACGGG

481  AAGCAGGCGC CTAAGGCCGT CGATCGCGGG CTGCTGCTGC AACGGGCCAA CGACGACCTG
      TTCGTCCGCG GATTCCGGCA GCTAGCGCCC GACGACGACG TTGCCCGGTT GCTGCTGGAC

541  GTGCTTGTGG TGCGTAATGT CCCGTTGGTC ACCGCCCCGC TGAGTCAGGT GCTCGGCCCG
      CACGAACACC ACGCATTACA GGGCAACCAG TGGCGGGGCG ACTCAGTCCA CGAGCCGGGC

601  ACCTGTCAGC GGTTGACATT CACCGCGCAC GCCGATCGGG TCGCCGCCGA ATTCGTCGGA
      TGGACAGTCG CCAACTGTAA GTGGCGCGTG CGGCTAGCCC AGCGGCGGCT TAAGCAGCCT

661  CTGGTGCAGG GACCCAATGC TGAGCACCCC GGTGCACCGC TGCGCGGTGA GCGCAGCGGC
      GACCACGTCC CTGGGTTACG ACTCGTGGGG CCACGTGGCG ACGCGCCACT CGCGTCGCCG

721  TACGACTTCC GCCCGCAGAT CGTCGGGGTG TTCACCGACC TGGCCGGGCC GGCGCCACCG
      ATGCTGAAGG CGGGCGTCTA GCAGCCCCAC AAGTGGCTGG ACCGGCCCGG CCGCGGTGGC

781  GGTCTGAGCT TCTCGGCGAG CGTGGATACC CGCTACAGCA GCAGCCCCAC GCCGCTGAAG
      CCAGACTCGA AGAGCCGCTC GCACCTATGG GCGATGTCGT CGTCGGGGTG CGGCGACTTC

841  ATGGCCGCCA TGATCCTCGG GGTAGCGCTC ACCGGCGCCG CCCTGGTGGC GCTGCACATC
      TACCGGCGGT ACTAGGAGCC CCATCGCGAG TGGCCGCGGC GGGACCACCG CGACGTGTAG

901  CTGGACACCG CCGACGGCAT GCGGCACCGG CGGTTCCTGC CGCGCGCTG GTGGTCGACC
      GACCTGTGGC GGCTGCCGTA CGCCGTGGCC GCCAAGGACG GCGCGCGAC CACCAGCTGG

961  GGCGGTCTGG ACACCCTGGT TATCGCCGTG CTGGTGTGGT GGCATTTCGT CGGGGCCAAC
      CCGCCAGACC TGTGGGACCA ATAGCGGCAC GACCACACCA CCGTAAAGCA GCCCCGGTTG

1021  ACCTCCGACG ACGGCTACAT CCTGACCATG GCCCGGGTGT CCGAGCATGC GGGCTATATG
      TGGAGGCTGC TGCCGATGTA GGACTGGTAC CGGGCCCACA GGCTCGTACG CCCGATATAC
```

FIG. 4A

```
1081  GCCAACTACT ACCGCTGGTT CGGCACACCC GAGGCGCCTT TCGGCTGGTA CTACGACCTG
      CGGTTGATGA TGGCGACCAA GCCGTGTGGG CTCCGCGGAA AGCCGACCAT GATGCTGGAC

1141  CTGGCGCTGT GGGCTCATGT CAGCACGGCC AGTATCTGGA TGCGCCTACC CACCCTGGCG
      GACCGCGACA CCCGAGTACA GTCGTGCCGG TCATAGACCT ACGCGGATGG GTGGGACCGC

1201  ATGGCGCTCA CCTGCTGGTG GGTAATCAGC CGTGAGGTCA TTCCCCGGCT GGGGCACGCC
      TACCGCGAGT GGACGACCAC CCATTAGTCG GCACTCCAGT AAGGGGCCGA CCCCGTGCGG

1261  GTCAAGACGA GCCGGGCAGC GGCGTGGACG GCGGCGGGCA TGTTTCTGGC TGTCTGGCTG
      CAGTTCTGCT CGGCCCGTCG CCGCACCTGC CGCCGCCCGT ACAAAGACCG ACAGACCGAC

1321  CCGCTGGACA ACGGCCTTCG GCCCGAGCCG ATCATCGCCC TGGGCATCCT GCTGACCTGG
      GGCGACCTGT TGCCGGAAGC CGGGCTCGGC TAGTAGCGGG ACCCGTAGGA CGACTGGACC

1381  TGCTCGGTGG AGCGGGCGGT GGCCACCAGC CGGCTGCTGC CGGTGGCAAT CGCCTGCATC
      ACGAGCCACC TCGCCCGCCA CCGGTGGTCG GCCGACGACG GCCACCGTTA GCGGACGTAG

1441  ATCGGTGCCT TGACCCTGTT CTCCGGGCCG ACGGGCATCG CCTCGATCGG TGCGCTGCTG
      TAGCCACGGA ACTGGGACAA GAGGCCCGGC TGCCCGTAGC GGAGCTAGCC ACGCGACGAC

1501  GTCGCGATCG GGCCGCTACG GACCATCCTG CACCGGCGTT CCAGGCGGTT CGGCGTGCTA
      CAGCGCTAGC CCGGCGATGC CTGGTAGGAC GTGGCCGCAA GGTCCGCCAA GCCGCACGAT

1561  CCACTGGTGG CGCCGATCCT GGCCGCGGCC ACCGTCACCG CGATCCCGAT CTTTCGTGAT
      GGTGACCACC GCGGCTAGGA CCGGCGCCGG TGGCAGTGGC GCTAGGGCTA GAAAGCACTA

1621  CAGACCTTCG CGGGCGAGAT CCAGGCCAAC CTCCTCAAGC GTGCCGTAGG GCCCAGCCTG
      GTCTGGAAGC GCCCGCTCTA GGTCCGGTTG GAGGAGTTCG CACGGCATCC CGGGTCGGAC

1681  AAGTGGTTCG ACGAACACAT CCGCTACGAG CGGCTGTTCA TGGCCAGCCC CGACGGCTCG
      TTCACCAAGC TGCTTGTGTA GGCGATGCTC GCCGACAAGT ACCGGTCGGG GCTGCCGAGC

1741  ATCGCCCGCC GCTTCGCCGT GCTGGCCTTG GTGCTGGCGC TCGCGGTATC GGTGGCAATG
      TAGCGGGCGG CGAAGCGGCA CGACCGGAAC CACGACCGCG AGCGCCATAG CCACCGTTAC

1801  TCGTTACGTA AGGGCCGCAT TCCAGGTACC GCTGCTGGAC CGAGCCGCCG CATCATCGGC
      AGCAATGCAT TCCCGGCGTA AGGTCCATGG CGACGACCTG GCTCGGCGGC GTAGTAGCCG

1861  ATCACGATCA TTTCCTTCCT CGCGATGATG TTCACCCCGA CAAAGTGGAC CCATCACTTC
      TAGTGCTAGT AAAGGAAGGA GCGCTACTAC AAGTGGGGCT GTTTCACCTG GGTAGTGAAG

1921  GGGGTGTTCG CGGGGTTGGC CGGGTCGCTG GGGGCGCTTG CCGCGGTCGC GGTGACGGGC
      CCCCACAAGC GCCCCAACCG GCCCAGCGAC CCCCGCGAAC GGCGCCAGCG CCACTGCCCG

1981  GCTGCGATGC GCTCGCGGCG GAACCGGACC GTGTTCGCCG CCGTGGTGGT CTTCGTGTTG
      CGACGCTACG CGAGCGCCGC CTTGGCCTGG CACAAGCGGC GGCACCACCA GAAGCACAAC

2041  GCCCTGTCGT TCGCCAGTGT CAACGGCTGG TGGTACGTGT CCAACTTCGG TGTGCCATGG
      CGGGACAGCA AGCGGTCACA GTTGCCGACC ACCATGCACA GGTTGAAGCC ACACGGTACC

2101  TCGAACTCGT TTCCGAAGTG GCGATGGTCG CTTACCACCG CACTCCTCGA GCTGACGGTG
      AGCTTGAGCA AAGGCTTCAC CGCTACCAGC GAATGGTGGC GTGAGGAGCT CGACTGCCAC

2161  CTGGTGCTGC TGCTAGCGGC ATGGTTCCAC TTCGTCGCCA ACGGTGACGG GCGCCGAACA
      GACCACGACG ACGATCGCCG TACCAAGGTG AAGCAGCGGT TGCCACTGCC CGCGGCTTGT

2221  GCCAGGCCAA CCCGGTTTAG GCACGACTA  GCCGGAATTG TCCAGTCCCC GTTGGCAATT
      CGGTCCGGTT GGGCCAAATC CCGTGCTGAT CGGCCTTAAC AGGTCAGGGG CAACCGTTAA
```

FIG. 4B

```
2281  GCCACGTGGT TGCTGGTGCT TTTCGAGGTG GTATCGCTGA CCCAGGCGAT GATTTCCCAG
      CGGTGCACCA ACGACCACGA AAAGCTCCAC CATAGCGACT GGGTCCGCTA CTAAAGGGTC

2341  TACCCGGCGT GGTCGGTTGG CCGGTCTAAC CTACAGGCTT TGGCCGGCAA GACCTGCGGG
      ATGGGCCGCA CCAGCCAACC GGCCAGATTG GATGTCCGAA ACCGGCCGTT CTGGACGCCC

2401  CTGGCCGAAG ACGTGCTGGT GGAGCTGGAT CCCAACGCAG GCATGCTGGC GCCGGTGACC
      GACCGGCTTC TGCACGACCA CCTCGACCTA GGGTTGCGTC CGTACGACCG CGGCCACTGG

2461  GCGCCGTTGG CCGACGCCCT GGGAGCCGGC CTGTCTGAAG CCTTCACACC CAACGGCATT
      CGCGGCAACC GGCTGCGGGA CCCTCGGCCG GACAGACTTC GGAAGTGTGG GTTGCCGTAA

2521  CCCGCCGACG TCACCGCCGA CCCGGTGATG GAACGTCCAG GGGATCGCAG TTTCCTCAAC
      GGGCGGCTGC AGTGGCGGCT GGGCCACTAC CTTGCAGGTC CCCTAGCGTC AAAGGAGTTG

2581  GACGACGGGC TGATCACCGG CAGCGAACCC GGCACCGAAG GGGCACCAC GGCCGCACCG
      CTGCTGCCCG ACTAGTGGCC GTCGCTTGGG CCGTGGCTTC CCCCGTGGTG CCGGCGTGGC

2641  GGAATCAACG GCTCCGCGC CCGGCTGCCC TACAACCTGG ACCCGGCCCG TACACCGGTG
      CCTTAGTTGC CGAGGGCGCG GGCCGACGGG ATGTTGGACC TGGGCCGGGC ATGTGGCCAC

2701  CTGGGCAGCT GGCGAGCCGG CGTGCAGGTG CCCGCCATGC TGCGGTCGGG CTGGTACCGG
      GACCCGTCGA CCGCTCGGCC GCACGTCCAC GGGCGGTACG ACGCCAGCCC GACCATGGCC

2761  CTGCCCACCA ACGAGCAGCG GGACAGGGCG CCGCTGCTGG TGGTGACGGC GGCCGGGCGA
      GACGGGTGGT TGCTCGTCGC CCTGTCCCGC GGCGACGACC ACCACTGCCG CCGGCCCGCT

2821  TTCGACTCCC GCGAGGTCCG GTTGCAGTGG GCCACCGACG AGCAAGCGGC CGCCGGACAC
      AAGCTGAGGG CGCTCCAGGC CAACGTCACC CGGTGGCTGC TCGTTCGCCG GCGGCCTGTG

2881  CACGGTGGGT CGATGGAATT CGCCGACGTC GGTGCCGCGC CGGCCTGGCG CAACCTGCGC
      GTGCCACCCA GCTACCTTAA GCGGCTGCAG CCACGGCGCG GCCGGACCGC GTTGGACGCG

2941  GCACCACTGT CCGCCATCCC GAGCACCGCC ACCCAGGTCC GGTTGGTCGC CGACGACCAG
      CGTGGTGACA GGCGGTAGGG CTCGTGGCGG TGGGTCCAGG CCAACCAGCG GCTGCTGGTC

3001  GATCTGGCGC CGCAGCACTG GATCGCCCTC ACACCACCGC GGATTCCGCG GGTGCGCACG
      CTAGACCGCG GCGTCGTGAC CTAGCGGGAG TGTGGTGGCG CCTAAGGCGC CCACGCGTGC

3061  CTGCAGAACG TGGTGGGCGC AGCGGATCCG GTGTTCCTGG ACTGGCTGGT GGGGCTGGCA
      GACGTCTTGC ACCACCCGCG TCGCCTAGGC CACAAGGACC TGACCGACCA CCCCGACCGT

3121  TTCCCCTGCC AACGCCCGTT CGGCCACCAA TACGGCGTCG ACGAGACACC CAAGTGGCGG
      AAGGGGACGG TTGCGGGCAA GCCGGTGGTT ATGCCGCAGC TGCTCTGTGG GTTCACCGCC

3181  ATCCTGCCGG ACCGGTTCGG CGCCGAAGCC AACTCACCGG TGATGGATCA CAATGGCGGT
      TAGGACGGCC TGGCCAAGCC GCGGCTTCGG TTGAGTGGCC ACTACCTAGT GTTACCGCCA

3241  GGCCCGCTGG GCATCACCGA GCTGCTGATG CGCGCAACCA CGGTGGCCAG CTACCTCAAA
      CCGGGCGACC CGTAGTGGCT CGACGACTAC GCGCGTTGGT GCCACCGGTC GATGGAGTTT

3301  GACGACTGGT TTAGGGACTG GGGCGCGTTA CAGCGGTTGA CGCCTTACTA CCCCGACGCC
      CTGCTGACCA AATCCCTGAC CCCGCGCAAT GTCGCCAACT GCGGAATGAT GGGGCTGCGG

3361  CAGCCCGCTG ATCTGAACCT AGGAACGGTG ACTCGCAGCG GCTGTGGAG TCCGGCGCCG
      GTCGGGCGAC TAGACTTGGA TCCTTGCCAC TGAGCGTCGC CCGACACCTC AGGCCGCGGC

3421  TTGCGCCGCG GCTAGAAGTG CCGTGGCCAC CGACTCGGCG ACAACCTCCG CGGCCCCGCA
      AACGCGGCGC CGATCTTCAC GGCACCGGTG GCTGAGCCGC TGTTGGAGGC GCCGGGGCGT
```

FIG. 4C

```
3481  TCCTCACCGC CCTTAACCGC GTCGCCTACC ATCGAGCCTC GTGCCCCACG ACGGTAATGA
      AGGAGTGGCG GGAATTGGCG CAGCGGATGG TAGCTCGGAG CACGGGGTGC TGCCATTACT

3541  GCGATCTCAC CGGATCGCAC GCCTAGCAGC CGTCGTCTCG GAATCGCGG GTCTGCTGCT
      CGCTAGAGTG GCCTAGCGTG CGGATCGTCG GCAGCAGAGC CCTTAGCGCC CAGACGACGA

3601  GTGCGGCATC GTTCCGCTGC TTCCGGTGAA CCAAACCACC GCGACCATCT TCTGGCCGCA
      CACGCCGTAG CAAGGCGACG AAGGCCACTT GGTTTGGTGG CGCTGGTAGA AGACCGGCGT

3661  GGGCAGCACC GCCGACGGCA ACATCACCCA GATCACCGCC CCTCTGGTAT CCGGGGCGCC
      CCCGTCGTGG CGGCTGCCGT TGTAGTGGGT CTAGTGGCGG GGAGACCATA GGCCCCGCGG

3721  ACGCGCGCTG GACATCTCGA TCCCCTGCTC GGCCATCGCC ACGCTGCCCG CCAACGGCGG
      TGCGCGCGAC CTGTAGAGCT AGGGGACGAG CCGGTAGCGG TGCGACGGGC GGTTGCCGCC

3781  CCTGGTGCTG TCCACACTGC CGGCCGGTGG CGTGGATACC GGTAAGGCCG GGCTGTTCGT
      GGACCACGAC AGGTGTGACG GCCGGCCACC GCACCTATGG CCATTCCGGC CCGACAAGCA

3841  CCGCGCCAAC CAGGACACGG TCGTGGCGTT CCGCGACTCG GTGGCCGCGG TGGCGGCCCG
      GGCGCGGTTG GTCCTGTGCC AGCACCGCAA GGCGCTGAGC CACCGGCGCC ACCGCCGGGC

3901  CTCCACGATC GCAGCGGGAG GCTGTAGCGC GCTGCATATC TGGGCCGATA CCGGCGGCGC
      GAGGTGCTAG CGTCGCCCTC CGACATCGCG CGACGTATAG ACCCGGCTAT GGCCGCCGCG

3961  GGGCGCTGAT TTTATGGGTA TACCCGGCGG CGCCGGGACC CTGCCGCCGG AGAAGAAGCC
      CCCGCGACTA AAATACCCAT ATGGGCCGCC GCGGCCCTGG GACGGCGGCC TCTTCTTCGG

4021  ACAGGTTGGC GGCATCTTCA CCGACCTGAA GGTCGGAGCG CAGCCCGGGC TGTCGGCCCG
      TGTCCAACCG CCGTAGAAGT GGCTGGACTT CCAGCCTCGC GTCGGGCCCG ACAGCCGGGC

4081  CGTCGACATC GACACTCGGT TTATCACGAC GCCCGGCGCG CTCAAGAAGG CCGTGATGCT
      GCAGCTGTAG CTGTGAGCCA AATAGTGCTG CGGGCCGCGC GAGTTCTTCC GGCACTACGA

4141  CCTCGGCGTG CTGGCGGTCC TGGTAGCCAT GGTGGGGCTG GCCGCGCTGG ACCGGCTCAG
      GGAGCCGCAC GACCGCCAGG ACCATCGGTA CCACCCCGAC CGGCGCGACC TGGCCGAGTC

4201  CAGGGGCCGC ACCCTGCGCG ACTGGCTGAC CCGATATCGC CCGCGGGTGC GGGTCGGATT
      GTCCCCGGCG TGGGACGCGC TGACCGACTG GGCTATAGCG GGCGCCCACG CCCAGCCTAA

4261  CGCCAGCCGG CTCGCTGACG CAGCGGTGAT CGCGACCTTG TTGCTCTGGC ATGTCATCGG
      GCGGTCGGCC GAGCGACTGC GTCGCCACTA GCGCTGGAAC AACGAGACCG TACAGTAGCC

4321  CGCCACCTCG TCCGATGACG GCTACCTTCT GACCGTCGCC CGGGTCGCCC CGAAGGCCGG
      GCGGTGGAGC AGGCTACTGC CGATGGAAGA CTGGCAGCGG GCCCAGCGGG GCTTCCGGCC

4381  CTATGTAGCC AACTACTACC GGTATTTCGG CACGACGGAG GCGCCGTTCG ACTGGTATAC
      GATACATCGG TTGATGATGG CCATAAAGCC GTGCTGCCTC CGCGGCAAGC TGACCATATG

4441  ATCGGTGCTT GCCCAGCTGG CGGCGGTGAG CACCGCCGGC GTCTGGATGC GCCTGCCCGC
      TAGCCACGAA CGGGTCGACC GCCGCCACTC GTGGCGGCCG CAGACCTACG CGGACGGGCG

4501  CACCCTGGCC GGAATCGCCT GCTGGCTGAT CGTCAGCCGT TTCGTGCTGC GGCGGCTGGG
      GTGGGACCGG CCTTAGCGGA CGACCGACTA GCAGTCGGCA AAGCACGACG CCGCCGACCC

4561  ACCGGGCCCG GCGGGCTGG CGTCCAACCG GGTCGCTGTG TTCACCGCTG GTGCGGTGTT
      TGGCCCGGGC CCGCCCGACC GCAGGTTGGC CCAGCGACAC AAGTGGCGAC CACGCCACAA

4621  CCTGTCCGCC TGGCTGCCGT TCAACAACGG CCTGCGTCCC GAGCCGCTGA TCGCGCTGGG
      GGACAGGCGG ACCGACGGCA AGTTGTTGCC GGACGCAGGG CTCGGCGACT AGCGCGACCC
```

FIG. 4D

```
4681  TGTGCTGGTC ACGTGGGTGT TGGTGGAACG GTCGATCGCG CTCGGACGGC TGGCCCCGGC
      ACACGACCAG TGCACCCACA ACCACCTTGC CAGCTAGCGC GAGCCTGCCG ACCGGGGCCG

4741  CGCGGTAGCC ATCATCGTGG CGACGCTTAC CGCGACGCTG GCACCGCAGG GGTTGATCGC
      GCGCCATCGG TAGTAGCACC GCTGCGAATG GCGCTGCGAC CGTGGCGTCC CCAACTAGCG

4801  GCTGGCCCCG CTGCTGACTG GTGCGCGCGC CATCGCCCAG AGGATCCGGC GCCGCGGGC
      CGACCGGGGC GACGACTGAC CACGCGCGCG GTAGCGGGTC TCCTAGGCCG CGGCGGCCCG

4861  GACCGATGGA CTGCTGGCGC CGCTGGCGGT GCTGGCCGCG GCGTTGTCGC TGATCACCGT
      CTGGCTACCT GACGACCGCG GCGACCGCCA CGACCGGCGC CGCAACAGCG ACTAGTGGCA

4921  GGTGGTGTTT CGGGACCAGA CGCTGGCCAC GGTGGCCGAA TCGGCACGCA TCAAGTACAA
      CCACCACAAA GCCCTGGTCT GCGACCGGTG CCACCGGCTT AGCCGTGCGT AGTTCATGTT

4981  GGTCGGCCCG ACCATCGCCT GGTACCAGGA CTTCCTGCGC TACTACTTCC TTACCGTGGA
      CCAGCCGGGC TGGTAGCGGA CCATGGTCCT GAAGGACGCG ATGATGAAGG AATGGCACCT

5041  GAGCAACGTT GAGGGGTCGA TGTCCCGCCG GTTCGCGGTG CTGGTGTTGC TGTTCTGCCT
      CTCGTTGCAA CTCCCCAGCT ACAGGGCGGC CAAGCGCCAC GACCACAACG ACAAGACGGA

5101  GTTCGGGGTG CTGTTCGTGC TGCTGCGGCG CGGCCGGGTG GCGGGGCTGG CCAGCGGCCC
      CAAGCCCCAC GACAAGCACG ACGACGCCGC GCCGGCCCAC CGCCCCGACC GGTCGCCGGG

5161  GGCCTGGCGA CTGATCGGCA CTACGGCGGT CGGCCTGCTG CTGCTCACGT TCACGCCAAC
      CCGGACCGCT GACTAGCCGT GATGCCGCCA GCCGGACGAC GACGAGTGCA AGTGCGGTTG

5221  CAAGTGGGCC GTGCAGTTCG GCGCATTCGC CGGGCTGGCC GGGGTGTTGG GTGCGGTCAC
      GTTCACCCGG CACGTCAAGC CGCGTAAGCG GCCCGACCGG CCCCACAACC CACGCCAGTG

5281  CGCGTTCACC TTTGCCCGCA TCGGTCTACA TAGTCGACGC AACCTCACGC TGTACGTGAC
      GCGCAAGTGG AAACGGGCGT AGCCAGATGT ATCAGCTGCG TTGGAGTGCG ACATGCACTG

5341  CGCGTTGCTG TTCGTGCTGG CGTGGGCAAC CTCGGGCATC AACGGGTGGT TCTACGTCGG
      GCGCAACGAC AAGCACGACC GCACCGTTG GAGCCCGTAG TTGCCACCA AGATGCAGCC

5401  CAACTACGGG GTGCCGTGGT ATGACATCCA GCCCGTCATC GCCAGCCACC CGGTGACGTC
      GTTGATGCCC CACGGCACCA TACTGTAGGT CGGGCAGTAG CGGTCGGTGG GCCACTGCAG

5461  GATGTTTCTG ACGCTGTCGA TCCTCACCGG ATTGCTGGCA GCCTGGTATC ACTTCCGGAT
      CTACAAAGAC TGCGACAGCT AGGAGTGGCC TAACGACCGT CGGACCATAG TGAAGGCCTA

5521  GGACTACGCC GGGCACACCG AAGTCAAAGA CAACCGGCGC AACCGCATCT TGGCCTCTAC
      CCTGATGCGG CCCGTGTGGC TTCAGTTTCT GTTGGCCGCG TTGGCGTAGA ACCGGAGATG

5581  GCCACTGCTG GTGGTCGCGG TGATCATGGT CGCAGGCGAA GTCGGCTCGA TGGCCAAGGC
      CGGTGACGAC CACCAGCGCC ACTAGTACCA GCGTCCGCTT CAGCCGAGCT ACCGGTTCCG

5641  CGCGGTGTTC CGTTACCCGC TTTACACCAC CGCCAAGGCC AACCTGACCG CGCTCAGCAC
      GCGCCACAAG GCAATGGGCG AAATGTGGTG GCGGTTCCGG TTGGACTGGC GCGAGTCGTG

5701  CGGGCTGTCC AGCTGTGCGA TGGCCGACGA CGTGCTGGCC GAGCCCGACC CCAATGCCGG
      GCCCGACAGG TCGACACGCT ACCGGCTGCT GCACGACCGG CTCGGGCTGG GGTTACGGCC

5761  CATGCTGCAA CCGGTTCCGG GCCAGGCGTT CGGACCGGAC GGACCGCTGG GCGGTATCAG
      GTACGACGTT GGCCAAGGCC CGGTCCGCAA GCCTGGCCTG CCTGGCGACC CGCCATAGTC

5821  TCCCGTCGGC TTCAAACCCG AGGGCGTGGG CGAGGACCTC AAGTCCGACC CGGTGGTCTC
      AGGGCAGCCG AAGTTTGGGC TCCCGCACCC GCTCCTGGAG TTCAGGCTGG GCCACCAGAG
```

FIG. 4E

```
5881  CAAACCCGGG CTGGTCAACT CCGATGCGTC GCCCAACAAA CCCAACGCCG CCATCACCGA
      GTTTGGGCCC GACCAGTTGA GGCTACGCAG CGGGTTGTTT GGGTTGCGGC GGTAGTGGCT

5941  CTCCGCGGGC ACCGCCGGAG GGAAGGGCCC GGTCGGGATC AACGGGTCGC ACGCGGCGCT
      GAGGCGCCCG TGGCGGCCTC CCTTCCCGGG CCAGCCCTAG TTGCCCAGCG TGCGCCGCGA

6001  GCCGTTCGGA TTGGACCCGG CACGTACCCC GGTGATGGGC AGCTACGGGG AGAACAACCT
      CGGCAAGCCT AACCTGGGCC GTGCATGGGG CCACTACCCG TCGATGCCCC TCTTGTTGGA

6061  GGCCGCCACG GCCACCTCGG CCTGGTACCA GTTACCGCCC CGCAGCCCGG ACCGGCCGCT
      CCGGCGGTGC CGGTGGAGCC GGACCATGGT CAATGGCGGG GCGTCGGGCC TGGCCGGCGA

6121  GGTGGTGGTT TCCGCGGCCG CGCCATCTG GTCCTACAAG GAGGACGGCG ATTTCATCTA
      CCACCACCAA AGGCGCCGGC GCGGTAGAC CAGGATGTTC CTCCTGCCGC TAAAGTAGAT

6181  CGGCCAGTCC CTGAAACTGC AGTGGGGCGT TCACCGGCCG ACGGCCGCA TCCAGCCACT
      GCCGGTCAGG GACTTTGACG TCACCCCGCA AGTGGCCGGC CTGCCGGCGT AGGTCGGTGA

6241  GGGGCAGGTA TTTCCGATCG ACATCGGACC GCAACCCGCG TGGCGCAATC TGCGGTTTCC
      CCCCGTCCAT AAAGGCTAGC TGTAGCCTGG CGTTGGGCGC ACCGCGTTAG ACGCCAAAGG

6301  GCTGGCCTGG GCGCCGCCGG AGGCCGACGT GGCGCGCATT GTCGCCTATG ACCCGAACCT
      CGACCGGACC CGCGGCGGCC TCCGGCTGCA CCGCGCGTAA CAGCGGATAC TGGGCTTGGA

6361  GAGCCCTGAG CAATGGTTCG CCTTCACCCC GCCCCGGGTT CCGGTGCTGG AATCTCTGCA
      CTCGGGACTC GTTACCAAGC GGAAGTGGGG CGGGGCCCAA GGCCACGACC TTAGAGACGT

6421  GCGGTTGATC GGGTCAGCGA CACCGGTGTT GATGGACATC GCGACCGCAG CCAACTTCCC
      CGCCAACTAG CCCAGTCGCT GTGGCCACAA CTACCTGTAG CGCTGGCGTC GGTTGAAGGG

6481  CTGCCAGCGA CCGTTTTCCG AGCATCTCGG CATTGCCGAG CTTCCGCAGT ACCGGATCCT
      GACGGTCGCT GGCAAAAGGC TCGTAGAGCC GTAACGGCTC GAAGGCGTCA TGGCCTAGGA

6541  GCCGGACCAC AAGCAGACGG CGGCGTCGTC GAACCTATGG CAGTCCAGCT CGACCGGCGG
      CGGCCTGGTG TTCGTCTGCC GCCGCAGCAG CTTGGATACC GTCAGGTCGA GCTGGCCGCC

6601  TCCGTTCCTG TTCACCCAGG CGCTGCTGCG CACCTCGACG ATCGCCACGT ACCTGCGTGG
      AGGCAAGGAC AAGTGGGTCC GCGACGACGC GTGGAGCTGC TAGCGGTGCA TGGACGCACC

6661  GGACTGGTAT CGCGACTGGG GATCGGTGGA GCAGTACCAC CGGCTGGTGC CGGCCGATCA
      CCTGACCATA GCGCTGACCC CTAGCCACCT CGTCATGGTG GCCGACCACG GCCGGCTAGT

6721  GGCTCCAGAC GCCGTTGTCG AGGAGGGCGT GATCACTGTG CCCGGCTGGG GTCGGCCAGG
      CCGAGGTCTG CGGCAACAGC TCCTCCCGCA CTAGTGACAC GGGCCGACCC CAGCCGGTCC

6781  ACCGATCAGG GCGCTGCCAT GACACAGTGC GCGAGCAGAC GCAAAAGCAC CCCAAATCGG
      TGGCTAGTCC CGCGACGGTA CTGTGTCACG CGCTCGTCTG CGTTTTCGTG GGGTTTAGCC

6841  GCGATTTTGG GGGCTTTTGC GTCTGCTCGC GGGACGCGCT GGGTGGCCAC CATCGCCGGG
      CGCTAAAACC CCCGAAAACG CAGACGAGCG CCCTGCGCGA CCCACCGGTG GTAGCGGCCC

6901  CTGATTGGCT TTGTGTTGTC GGTGGCGACG CCGCTGCTGC CCGTCGTGCA GACCACCGCG
      GACTAACCGA AACACAACAG CCACCGCTGC GGCGACGACG GGCAGCACGT CTGGTGGCGC

6961  ATGCTCGACT GGCCACAGCG GGGGCAACTG GCAGCGTGA CCGCCCCGCT GATCTCGCTG
      TACGAGCTGA CCGGTGTCGC CCCCGTTGAC CGTCGCACT GGCGGGGCGA CTAGAGCGAC

7021  ACGCCGGTCG ACTTTACCGC CACCGTGCCG TGCGACGTGG TGCGCGCCAT GCCACCCGCG
      TGCGGCCAGC TGAAATGGCG GTGGCACGGC ACGCTGCACC ACGCGCGGTA CGGTGGGCGC
```

FIG. 4F

```
7081  GGCGGGGTGG TGCTGGGCAC CGCACCCAAG CAAGGCAAGG ACGCCAATTT GCAGGCGTTG
      CCGCCCCACC ACGACCCGTG GCGTGGGTTC GTTCCGTTCC TGCGGTTAAA CGTCCGCAAC

7141  TTCGTCGTCG TCAGCGCCCA GCGCGTGGAC GTCACCGACC GCAACGTGGT GATCTTGTCC
      AAGCAGCAGC AGTCGCGGGT CGCGCACCTG CAGTGGCTGG CGTTGCACCA CTAGAACAGG

7201  GTGCCGCGCG AGCAGGTGAC GTCCCCGCAG TGTCAACGCA TCGAGGTCAC CTCTACCCAC
      CACGGCGCGC TCGTCCACTG CAGGGGCGTC ACAGTTGCGT AGCTCCAGTG GAGATGGGTG

7261  GCCGGCACCT TCGCCAACTT CGTCGGGCTC AAGGACCCGT CGGGCGCGCC GCTGCGCAGC
      CGGCCGTGGA AGCGGTTGAA GCAGCCCGAG TTCCTGGGCA GCCCGCGCGG CGACGCGTCG

7321  GGCTTCCCCG ACCCCAACCT GCGCCCGCAG ATTGTCGGGG TGTTCACCGA CCTGACCGGG
      CCGAAGGGGC TGGGGTTGGA CGCGGGCGTC TAACAGCCCC ACAAGTGGCT GGACTGGCCC

7381  CCCGCGCCGC CCGGGCTGGC GGTCTCGGCG ACCATCGACA CCCGGTTCTC CACCCGGCCG
      GGGCGCGGCG GGCCCGACCG CCAGAGCCGC TGGTAGCTGT GGGCCAAGAG GTGGGCCGGC

7441  ACCACGCTGA AACTGCTGGC GATCATCGGG GCGATCGTGG CCACCGTCGT CGCACTGATC
      TGGTGCGACT TTGACGACCG CTAGTAGCCC CGCTAGCACC GGTGGCAGCA GCGTGACTAG

7501  GCGTTGTGGC GCCTGGACCA GTTGGACGGG CGGGGCTCAA TTGCCCAGCT CCTCCTCAGG
      CGCAACACCG CGGACCTGGT CAACCTGCCC GCCCCGAGTT AACGGGTCGA GGAGGAGTCC

7561  CCGTTCCGGC CTGCATCGTC GCCGGGCGGC ATGCGCCGGC TGATTCCGGC AAGCTGGCGC
      GGCAAGGCCG GACGTAGCAG CGGCCCGCCG TACGCGGCCG ACTAAGGCCG TTCGACCGCG

7621  ACCTTCACCC TGACCGACGC CGTGGTGATA TTCGGCTTCC TGCTCTGGCA TGTCATCGGC
      TGGAAGTGGG ACTGGCTGCG GCACCACTAT AAGCCGAAGG ACGAGACCGT ACAGTAGCCG

7681  GCGAATTCGT CGGACGACGG CTACATCCTG GGCATGGCCC GAGTCGCCGA CCACGCCGGC
      CGCTTAAGCA GCCTGCTGCC GATGTAGGAC CCGTACCGGG CTCAGCGGCT GGTGCGGCCG

7741  TACATGTCCA ACTATTTCCG CTGGTTCGGC AGCCCGGAGG ATCCCTTCGG CTGGTATTAC
      ATGTACAGGT TGATAAAGGC GACCAAGCCG TCGGGCCTCC TAGGGAAGCC GACCATAATG

7801  AACCTGCTGG CGCTGATGAC CCATGTCAGC GACGCCAGTC TGTGGATGCG CCTGCCAGAC
      TTGGACGACC GCGACTACTG GGTACAGTCG CTGCGGTCAG ACACCTACGC GGACGGTCTG

7861  CTGGCCGCCG GGCTAGTGTG CTGGCTGCTG CTGTCGCGTG AGGTGCTGCC CCGCCTCGGG
      GACCGGCGGC CCGATCACAC GACCGACGAC GACAGCGCAC TCCACGACGG GGCGGAGCCC

7921  CCGGCGGTGG AGGCCAGCAA ACCCGCCTAC TGGGCGGCGG CCATGGTCTT GCTGACCGCG
      GGCCGCCACC TCCGGTCGTT TGGGCGGATG ACCCGCCGCC GGTACCAGAA CGACTGGCGC

7981  TGGATGCCGT TCAACAACGG CCTGCGGCCG GAGGGCATCA TCGCGCTCGG CTCGCTGGTC
      ACCTACGGCA AGTTGTTGCC GGACGCCGGC CTCCCGTAGT AGCGCGAGCC GAGCGACCAG

8041  ACCTATGTGC TGATCGAGCG GTCCATGCGG TACAGCCGGC TCACACCGGC GGCGCTGGCC
      TGGATACACG ACTAGCTCGC CAGGTACGCC ATGTCGGCCG AGTGTGGCCG CCGCGACCGG

8101  GTCGTTACCG CCGCATTCAC ACTGGGTGTG CAGCCCACCG GCCTGATCGC GGTGGCCGCG
      CAGCAATGGC GGCGTAAGTG TGACCCACAC GTCGGGTGGC CGGACTAGCG CCACCGGCGC

8161  CTGGTGGCCG GCGGCCGCCC GATGCTGCGG ATCTTGGTGC GCCGYCATCG CCTGGTCGGC
      GACCACCGGC CGCCGGCGGG CTACGACGCC TAGAACCACG CGGCRGTAGC GGACCAGCCG

8221  ACGTTGCCGT TGGTGTCGCC GATGCTGGCC GCCGGCACCG TCATCCTGAC CGTGGTGTTC
      TGCAACGGCA ACCACAGCGG CTACGACCGG CGGCCGTGGC AGTAGGACTG GCACCACAAG
```

FIG. 4G

```
8281  GCCGACCAGA CCCTGTCAAC GGTGTTGGAA GCCACCAGGG TTCGCGCCAA AATCGGGCCG
      CGGCTGGTCT GGGACAGTTG CCACAACCTT CGGTGGTCCC AAGCGCGGTT TTAGCCCGGC

8341  AGCCAGGCGT GGTATACCGA GAACCTGCGT TACTACTACC TCATCCTGCC CACCGTCGAC
      TCGGTCCGCA CCATATGGCT CTTGGACGCA ATGATGATGG AGTAGGACGG GTGGCAGCTG

8401  GGTTCGCTGT CGCGGCGCTT CGGCTTTTTG ATCACCGCGC TATGCCTGTT CACCGCGGTG
      CCAAGCGACA GCGCCGCGAA GCCGAAAAAC TAGTGGCGCG ATACGGACAA GTGGCGCCAC

8461  TTCATCATGT TGCGGCGCAA GCGAATTCCC AGCGTGGCCC GCGGACCGGC GTGGCGGCTG
      AAGTAGTACA ACGCCGCGTT CGCTTAAGGG TCGCACCGGG CGCCTGGCCG CACCGCCGAC

8521  ATGGGCGTCA TCTTCGGCAC CATGTTCTTC CTGATGTTCA CGCCCACCAA GTGGGTGCAC
      TACCCGCAGT AGAAGCCGTG GTACAAGAAG GACTACAAGT GCGGGTGGTT CACCCACGTG

8581  CACTTCGGGC TGTTCGCCGC CGTAGGGGCG GCGATGGCCG CGCTGACGAC GGTGTTGGTA
      GTGAAGCCCG ACAAGCGGCG GCATCCCCGC CGCTACCGGC GCGACTGCTG CCACAACCAT

8641  TCCCCATCGG TGCTGCGCTG GTCGCGCAAC CGGATGGCGT TCCTGGCGGC GTTATTCTTC
      AGGGGTAGCC ACGACGCGAC CAGCGCGTTG GCCTACCGCA AGGACCGCCG CAATAAGAAG

8701  CTGCTGGCGT TGTGTTGGGC CACCACCAAC GGCTGGTGGT ATGTCTCCAG CTACGGTGTG
      GACGACCGCA ACACAACCCG GTGGTGGTTG CCGACCACCA TACAGAGGTC GATGCCACAC

8761  CCGTTCAACA GCGCGATGCC GAAGATCGAC GGGATCACAG TCAGCACAAT CTTTTTCGCC
      GGCAAGTTGT CGCGCTACGG CTTCTAGCTG CCCTAGTGTC AGTCGTGTTA GAAAAGCGG

8821  CTGTTTGCGA TCGCCGCCGG CTATGCGGCC TGGCTGCACT TCGCGCCCCG CGGCGCCGGC
      GACAAACGCT AGCGGCGGCC GATACGCCGG ACCGACGTGA AGCGCGGGGC GCCGCGGCCG

8881  GAAGGGCGGC TGATCCGCGC GCTGACGACA GCCCCGGTAC CGATCGTGGC CGGTTTCATG
      CTTCCCGCCG ACTAGGCGCG CGACTGCTGT CGGGGCCATG GCTAGCACCG GCCAAAGTAC

8941  GCGGCGGTGT TCGTCGCGTC CATGGTGGCC GGGATCGTGC GACAGTACCC GACCTACTCC
      CGCCGCCACA AGCAGCGCAG GTACCACCGG CCCTAGCACG CTGTCATGGG CTGGATGAGG

9001  AACGGCTGGT CCAACGTGCG GGCGTTTGTC GGCGGCTGCG GACTGGCCGA CGACGTACTC
      TTGCCGACCA GGTTGCACGC CCGCAAACAG CCGCCGACGC CTGACCGGCT GCTGCATGAG

9061  GTCGAGCCTG ATACCAATGC GGGTTTCATG AAGCCGCTGG ACGGCGATTC GGGTTCTTGG
      CAGCTCGGAC TATGGTTACG CCCAAAGTAC TTCGGCGACC TGCCGCTAAG CCCAAGAACC

9121  GGCCCCTTGG GCCCGCTGGG TGGAGTCAAC CCGGTCGGCT TCACGCCCAA CGGCGTACCG
      CCGGGGAACC CGGGCGACCC ACCTCAGTTG GGCCAGCCGA AGTGCGGGTT GCCGCATGGC

9181  GAACACACGG TGGCCGAGGC GATCGTGATG AAACCCAACC AGCCCGGCAC CGACTACGAC
      CTTGTGTGCC ACCGGCTCCG CTAGCACTAC TTTGGGTTGG TCGGGCCGTG GCTGATGCTG

9241  TGGGATCGCC CGACCAAGCT GACGAGTCCT GGCATCAATG GTTCTACGGT GCCGCTGCCC
      ACCCTACGCG GCTGGTTCGA CTGCTCAGGA CCGTAGTTAC CAAGATGCCA CGGCGACGGG

9301  TATGGGCTCG ATCCCGCCCG GGTACCGTTG GCAGGCACCT ACACCACCGG CGCACAGCAA
      ATACCCGAGC TAGGGCGGGC CCATGGCAAC CGTCCGTGGA TGTGGTGGCC GCGTGTCGTT

9361  CAGAGCACAC TCGTCTCGGC GTGGTATCTC CTGCCTAAGC CGGACGACGG GCATCCGCTG
      GTCTCGTGTG AGCAGAGCCG CACCATAGAG GACGGATTCG CCGCTGCTGCC CGTAGGCGAC

9421  GTCGTGGTGA CCGCCGCGGG CAAGATCGCC GGCAACAGCG TGCTGCACGG GTACACCCCC
      CAGCACCACT GGCGGCGCCC GTTCTAGCGG CCGTTGTCGC ACGACGTGCC CATGTGGGGG
```

FIG. 4H

```
9481   GGGCAGACTG TGGTGCTCGA ATACGCCATG CCGGGACCCG GAGCGCTGGT ACCCGCCGGG
       CCCGTCTGAC ACCACGAGCT TATGCGGTAC GGCCCTGGGC CTCGCGACCA TGGGCGGCCC

9541   CGGATGGTGC CCGACGACCT ATACGGAGAG CAGCCCAAGG CGTGGCGCAA CCTGCGCTTC
       GCCTACCACG GGCTGCTGGA TATGCCTCTC GTCGGGTTCC GCACCGCGTT GGACGCGAAG

9601   GCCCGAGCAA AGATGCCCGC CGATGCCGTC GCGGTCCGGG TGGTGGCCGA GGATCTGTCG
       CGGGCTCGTT TCTACGGGCG GCTACGGCAG CGCCAGGCCC ACCACCGGCT CCTAGACAGC

9661   CTGACACCGG AGGACTGGAT CGCGGTGACC CCGCCGCGGG TACCGGACCT GCGCTCACTG
       GACTGTGGCC TCCTGACCTA GCGCCACTGG GGCGGCGCCC ATGGCCTGGA CGCGAGTGAC

9721   CAGGAATATG TGGGCTCGAC GCAGCCGGTG CTGCTGGACT GGGCGGTCGG TTTGGCCTTC
       GTCCTTATAC ACCCGAGCTG CGTCGGCCAC GACGACCTGA CCCGCCAGCC AAACCGGAAG

9781   CCGTGCCAGC AGCCGATGCT GCACGCCAAT GGCATCGCCG AAATCCCGAA GTTCCGCATC
       GGCACGGTCG TCGGCTACGA CGTGCGGTTA CCGTAGCGGC TTTAGGGCTT CAAGGCGTAG

9841   ACACCGGACT ACTCGGCTAA GAAGCTGGAC ACCGACACGT GGGAAGACGG CACTAACGGC
       TGTGGCCTGA TGAGCCGATT CTTCGACCTG TGGCTGTGCA CCCTTCTGCC GTGATTGCCG

9901   GGCCTGCTCG GGATCACCGA CCTGTTGCTG CGGGCCCACG TCATGGCCAC CTACCTGTCC
       CCGGACGAGC CCTAGTGGCT GGACAACGAC GCCCGGGTGC AGTACCGGTG GATGGACAGG

9961   CGCGACTGGG CCCGCGATTG GGGTTCCCTG CGCAAGTTCG ACACCCTGGT CGATGCCCCT
       GCGCTGACCC GGGCGCTAAC CCCAAGGGAC GCGTTCAAGC TGTGGGACCA GCTACGGGGA

10021  CCCGCCCAGC TCGAGTTGGG CACCGCGACC CGCAGCGGCC TGTGGTCACC GGGCAAGATC
       GGGCGGGTCG AGCTCAACCC GTGGCGCTGG GCGTCGCCGG ACACCAGTGG CCCGTTCTAG

10081  CGAATTGGTC CATAG
       GCTTAACCAG GTATC
```

FIG. 4I

```
   1 TGTTCGACGA TCCGCGGTTC GAGGTGTCCG ACCACGGTCC GTTCGTGCTC GCGATCAGGA
     ACAAGCTGCT AGGCGCCAAG CTCCACAGGC TGGTGCCAGG CAAGCACGAG CGCTAGTCCT

61 AACCCGGGGG AAAGCCGGAG ACCGATGGCC ACTGATATCC CGTTAGCATC GAAGCCCGTG
     TTGGGCCCCC TTTCGGCCTC TGGCTACCGG TGACTATAGG GCAATCGTAG CTTCGGGCAC

121 ACCGGTCCGC ATGCAGCGGG TGGCAGCAAC CACCGCACCG CGCGGCTCGT CGCGATCATC
     TGGCCAGGCG TACGTCGCCC ACCGTCGTTG GTGGCGTGGC GCGCCGAGCA GCGCTAGTAG

181 GCCGGACTTC TCGGCACGCT GATGGCGATC GCGACGCCGC TGCTGCCGGT CGAGCAGACC
     CGGCCTGAAG AGCCGTGCGA CTACCGCTAG CGCTGCGGCG ACGACGGCCA GCTCGTCTGG

241 ACCGCCGAGC TCAACTGGCC GCAGAACGGC GTCTGGCAGA GCGTCGACGC GCCGCTGATC
     TGGCGGCTCG AGTTGACCGG CGTCTTGCCG CAGACCGTCT CGCAGCTGCG CGGCGACTAG

301 GGCTACGTCG CGACCGACCT GACCGTCACC GTGCCGTGCC AGGCCGCCGC GGGCCTGGTG
     CCGATGCAGC GCTGGCTGGA CTGGCAGTGG CACGGCACGG TCCGGCGGCG CCCGGACCAC

361 GGACCGGAGA ACCGCAACCG CAGCGTGCTG TTGTCGACGG TGCCCAAGCA GGCCCCCAAG
     CCTGGCCTCT TGGCGTTGGC GTCGCACGAC AACAGCTGCC ACGGGTTCGT CCGGGGGTTC

421 GCCATCGACC GCGGCCTGCT GATCGAACGC ATCAACAACG ACCTCACGGT CATCGTGCGC
     CGGTAGCTGG CGCCGGACGA CTAGCTTGCG TAGTTGTTGC TGGAGTGCCA GTAGCACGCG

481 AACACCCCGG TCGTCAGCGC ACCGCTGGAG CAGGTGCTCA GCCCCGACTG CCGGTACCTG
     TTGTGGGGCC AGCAGTCGCG TGGCGACCTC GTCCACGAGT CGGGGCTGAC GGCCATGGAC

541 ACGTTCACCG CGCACGCCGA CAAGGTGACC GGTGAGTTCG TCGGCCTCAC GCAGGGTCCC
     TGCAAGTGGC GCGTGCGGCT GTTCCACTGG CCACTCAAGC AGCCGGAGTG CGTCCCAGGG

601 GATGACGACG ACCCGGGCGA GGCGGTGCGC GGCGAGCGCA GCGGCTACGA CTTCCGTCCC
     CTACTGCTGC TGGGCCCGCT CCGCCACGCG CCGCTCGCGT CGCCGATGCT GAAGGCAGGG

661 CAGATCGTCG GTGTGTTCAC CGACCTGTCC GGCCCGGCGC CCGAAGGGCT GCAGTTGTCG
     GTCTAGCAGC CACACAAGTG GCTGGACAGG CCGGGCCGCG GGCTTCCCGA CGTCAACAGC

721 GCGACCATCG ACACGCGCTA CAGCACGTCG CCGACCCTGC TGAAACTGCT CGCGATGATC
     CGCTGGTAGC TGTGCGCGAT GTCGTGCAGC GGCTGGGACG ACTTTGACGA GCGCTACTAG

781 GTGGGCGTCG CGATGACCGT CATCGCGCTC GGCGCGCTGC ACGTGCTGGA CTGCGCCGAC
     CACCCGCAGC GCTACTGGCA GTAGCGCGAG CCGCGCGACG TGCACGACCT GACGCGGCTG

841 GGCCGGCGCC ACAAGCGCTT CCTGCCGTCG CGCTGGTGGT CGATGACGCC GCTGGACGGG
     CCGGCCGCGG TGTTCGCGAA GGACGGCAGC GCGACCACCA GCTACTGCGG CGACCTGCCC

901 CTGGTCAGCG CGATGCTGGT GTGGTGGCAC TTCGTCGGCG CCAACACGGC CGACGACGGC
     GACCAGTCGC GCTACGACCA CACCACCGTG AAGCAGCCGC GGTTGTGCCG GCTGCTGCCG

961 TACATCCTGA CCATGGCCCG TGTGTCCGAG CACGCCGGCT ACATGGCCAA CTACTACCGC
     ATGTAGGACT GGTACCGGGC ACACAGGCTC GTGCGGCCGA TGTACCGGTT GATGATGGCG

1021 TGGTTCGGTA CGCCTGAGTC GCCGTTCGGC TGGTACTACG ACCTGCTGGC GTTGTGGGCG
     ACCAAGCCAT GCGGACTCAG CGGCAAGCCG ACCATGATGC TGGACGACCG CAACACCCGC
```

FIG. 6A

```
1081  CACGTGTCGA CGGCCAGCGT GTGGATGCGC TTCCCCACGC TGCTCATGGG TCTGGCCTGC
      GTGCACAGCT GCCGGTCGCA CACCTACGCG AAGGGGTGCG ACGAGTACCC AGACCGGACG

1141  TGGTGGGTGA TCAGCCGCGA GGTCATCCCG CGCCTGGGCG CCGCCGCCAA GCACAGCCGC
      ACCACCCACT AGTCGGCGCT CCAGTAGGGC GCGGACCCGC GGCGGCGGTT CGTGTCGGCG

1201  GCCGCGGCAT GGACCGCCGC GGGCCTGTTC CTGGCGTTCT GGCTGCCGCT CAACAACGGG
      CGGCGCCGTA CCTGGCGGCG CCCGGACAAG GACCGCAAGA CCGACGGCGA GTTGTTGCCC

1261  TTGCGCCCCG AGCCCATCAT CGCGCTGGGC ATCCTGCTGA CGTGGTGCTC GGTGGAGCGC
      AACGCGGGGC TCGGGTAGTA GCGCGACCCG TAGGACGACT GCACCACGAG CCACCTCGCG

1321  GGCGTCGCGA CCAGCAGGCT GCTGCCGGTG CCGTCGCCA TCATCATCGG TGCACTCACG
      CCGCAGCGCT GGTCGTCCGA CGACGGCCAC CGGCAGCGGT AGTAGTAGCC ACGTGAGTGC

1381  CTGTTCTCCG GCCCCACCGG CATCGCCGCT GTCGGCGCCC TGCTGGTCGC CATCGGACCG
      GACAAGAGGC CGGGGTGGCC GTAGCGGCGA CAGCCGCGGG ACGACCAGCG GTAGCCTGGC

1441  CTGAAAACCA TTGTGGCCGC GCATGTTTCA CGGTTCGGCT ATTGGGCACT GCTGGCGCCG
      GACTTTTGGT AACACCGGCG CGTACAAAGT GCCAAGCCGA TAACCCGTGA CGACCGCGGC

1501  ATCGCCGCGG CGGGCACCGT CACGATCTTC CTGATCTTCC GCGACCAGAC CCTGGCCGCC
      TAGCGGCGCC GCCCGTGGCA GTGCTAGAAG GACTAGAAGG CGCTGGTCTG GGACCGGCGG

1561  GAACTGCAGG CCAGCAGCTT CAAGTCGGCC GTCGGCCCCA GCCTGGCCTG GTTCGACGAG
      CTTGACGTCC GGTCGTCGAA GTTCAGCCGG CAGCCGGGGT CGGACCGGAC CAAGCTGCTC

1621  CACATCCGCT ACTCACGCCT GTTCACCACA AGCCCCGACG GTTCGGTGGC GCGGCGCTTC
      GTGTAGGCGA TGAGTGCGGA CAAGTGGTGT TCGGGGCTGC CAAGCCACCG CGCCGCGAAG

1681  GCGGTGCTCA CGCTGCTGCT CGCGCTGGCG GTGTCGATCG CGATGACGCT GCGCAAGGGC
      CGCCACGAGT GCGACGACGA GCGCGACCGC CACAGCTAGC GCTACTGCGA CGCGTTCCCG

1741  CGCATCCCCG GCACCGCGCT GGGCCCGAGC AGACGCATCA TCGGCATCAC GATCATCTCG
      GCGTAGGGGC CGTGGCGCGA CCCGGGCTCG TCTGCGTAGT AGCCGTAGTG CTAGTAGAGC

1801  TTCCTCGCGA TGATGTTCAC CCCGACCAAG TGGACCCACC AATTCGGTGT GTTCGCCGGC
      AAGGAGCGCT ACTACAAGTG GGGCTGGTTC ACCTGGGTGG TTAAGCCACA CAAGCGGCCG

1861  CTCGCGGGGT GCCTCGGCGC CCTGGCCGCC GTCGCGGTCA CCACGACCGC GATGAAGTCG
      GAGCGCCCCA CGGAGCCGCG GGACCGGCGG CAGCGCCAGT GGTGCTGGCG CTACTTCAGC

1921  CGGCGTAACC GCACGGTGTT CGGCGCGGCA GTGCTGTTCG TGACGGCGCT GTCGTTCGCG
      GCCGCATTGG CGTGCCACAA GCCGCGCCGT CACGACAAGC ACTGCCGCGA CAGCAAGCGC

1981  ACGGTCAACG GCTGGTGGTA CGTGTCCAAT TTCGGTGTGC CCTGGTCGAA CTCGTTCCCC
      TGCCAGTTGC CGACCACCAT GCACAGGTTA AAGCCACACG GGACCAGCTT GAGCAAGGGG

2041  GAGTTCAAGT TCGGGTTCAC CACGATGCTG CTGGGCCTGT CGGTGCTCGC GCTGCTGGTC
      CTCAAGTTCA AGCCCAAGTG GTGCTACGAC GACCCGGACA GCCACGAGCG CGACGACCAG

2101  GCGGCATGGT TCCACTTCAG CGGGCGCGAC GTCTCGCCCG ACCGGCCGCA ACGGCGCTGG
      CGCCGTACCA AGGTGAAGTC GCCCGCGCTG CAGAGCGGGC TGGCCGGCGT TGCCGCGACC

2161  CAGCGCCTTC TGGTCGCCCC GCTCGCGGTC GCCACGTGGG CACTGGTGAT CTTCGAGGTG
      GTCGCGGAAG ACCAGCGGGG CGAGCGCCAG CGGTGCACCC GTGACCACTA GAAGCTCCAC

2221  GTCTCGCTGA CGCTGGGGAT GATCAACCAG TACCCGGCGT GGTCGGTGGG CCGCTCCAAC
      CAGAGCGACT GCGACCCCTA CTAGTTGGTC ATGGGCCGCA CCAGCCACCC GGCGAGGTTG
```

FIG. 6B

```
2281  CTCAACGCCC TGACCGGCAA GACCTGCGGA CTGGCCAACG ACGTGCTGGT CGAGCAGAAC
      GAGTTGCGGG ACTGGCCGTT CTGGACGCCT GACCGGTTGC TGCACGACCA GCTCGTCTTG

2341  GCCAACGCGG GCATGCTCAC CCCGATCGGT GAGCCGGCCG GTCAGGCGCT CGGCGCCGTG
      CGGTTGCGCC CGTACGAGTG GGGCTAGCCA CTCGGCCGGC CAGTCCGCGA GCCGCGGCAC

2401  ACCTCGCTGG GCTTCGGGCC GAACGGCATC CCCTCGGATG TCTCCGCGGA CCCCGTCATG
      TGGAGCGACC CGAAGCCCGG CTTGCCGTAG GGGAGCCTAC AGAGGCGCCT GGGGCAGTAC

2461  GAGCAGCCCG GCACGGACAA CTTCGCCGAC AGCGACTCCG GCGTCGTCAC CGGCACCGAG
      CTCGTCGGGC CGTGCCTGTT GAAGCGGCTG TCGCTGAGGC CGCAGCAGTG GCCGTGGCTC

2521  GTCGGCACGG AAGGCGGCAC CACAGCTGCC GCGGGCATCA ACGGATCCCG CGCGCGCCTG
      CAGCCGTGCC TTCCGCCGTG GTGTCGACGG CGCCCGTAGT TGCCTAGGGC GCGCGCGGAC

2581  CCGTACGGCC TGAACCCGGC CACCACGCCG GTGCTCGGTT CGTGGCGTTC GGGCACACAG
      GGCATGCCGG ACTTGGGCCG GTGGTGCGGC CACGAGCCAA GCACCGCAAG CCCGTGTGTC

2641  CAGCCCGCGG TGCTGCGCTC GGCGTGGTAC CGGCTGCCCG ACCGCGACCA GGCGGGCCCG
      GTCGGGCGCC ACGACGCGAG CCGCACCATG GCCGACGGGC TGGCGCTGGT CCGCCCGGGC

2701  CTGCTCGTGG TGTCGGCCGC CGGTCGGTTC GACCAGGGCG AGGTCGAGGT GCAGTGGGCC
      GACGAGCACC ACAGCCGGCG GCCAGCCAAG CTGGTCCCGC TCCAGCTCCA CGTCACCCGG

2761  ACCGACGAGC AGGCCGCGGC CAACGAGCCG GGCGGCAGCA TCACCTTCGG TGACGTCGGC
      TGGCTGCTCG TCCGGCGCCG GTTGCTCGGC CCGCCGTCGT AGTGGAAGCC ACTGCAGCCG

2821  GCGGCCCCGG CCTGGCGCAA CCTGCGCGCC CCGCTGAGCT CGATCCCGCC CGAGGCCACC
      CGCCGGGGCC GGACCGCGTT GGACGCGCGG GGCGACTCGA GCTAGGGCGG GCTCCGGTGG

2881  CAGATCCGGC TGGTCGCCAG CGACGACGAT CTCGCACCCC AGCACTGGAT CGCCCTGACC
      GTCTAGGCCG ACCAGCGGTC GCTGCTGCTA GAGCGTGGGG TCGTGACCTA GCGGGACTGG

2941  CCGCCGCGCA TCCCCGAGCT GCGCACGCTG CAGGAGGTCG TCGGATCGTC CGACCCGGTG
      GGCGGCGCGT AGGGGCTCGA CGCGTGCGAC GTCCTCCAGC AGCCTAGCAG GCTGGGCCAC

3001  ATGCTGGACT GGCTCGTAGG CCTGGCGTTC CCGTGCCAGC GGCCGTTCGA CCACCGCTAC
      TACGACCTGA CCGAGCATCC GGACCGCAAG GCACGGTCG CCGGCAAGCT GGTGGCGATG

3061  GGCGTCGTCG AGGTGCCCAA GTGGCGCATC CTGCCGGACC GGTTCGGCGC CGAGGCCAAT
      CCGCAGCAGC TCCACGGGTT CACCGCGTAG GACGGCCTGG CCAAGCCGCG GCTCCGGTTA

3121  TCGCCGGTCA TGGACTACCT GGGCGGCGGC CCGCTCGGCA TCACCGAGCT GCTGCTGCGC
      AGCGGCCAGT ACCTGATGGA CCCGCCGCCG GGCGAGCCGT AGTGGCTCGA CGACGACGCG

3181  CCGTCGTCGG TGCCGACCTA CCTCAAGGAC GACTGGTACC GCGACTGGGG CTCGTTGCAG
      GGCAGCAGCC ACGGCTGGAT GGAGTTCCTG CTGACCATGG CGCTGACCCC GAGCAACGTC

3241  CGGCTGACGC CGTGGTACCC GGACGCCCAG CCGGCGCGCC TGGACCTCGG CACGGCCACG
      GCCGACTGCG GCACCATGGG CCTGCGGGTC GGCCGCGCGG ACCTGGAGCC GTGCCGGTGC

3301  CGCAGCGGCT GGTGGAGCCC GGCGCCCTG CGGCTGAGTT GAGCGGCTGA GCTAGCGGCT
      GCGTCGCCGA CCACCTCGGG CCGCGGGGAC GCCGACTCAA CTCGCCGACT CGATCGCCGA

3361  GAGCGATCAC GGTAGGGCCC ACGCGCGCCC GCATGGCCGA CGCTCACATG CGGGTCGCAT
      CTCGCTAGTG CCATCCCGGC TGCGCGCGGG CGTACCGGCT GCGAGTGTAC GCCCAGCGTA

3421  ACCATCGAGC CTCGTGCCGG GCGATGAACA GCGTGAGCGA ACAGCAGATG ACGCAGTGAC
      TGGTAGCTCG GAGCACGGCC CGCTACTTGT CGCACTCGCT TGTCGTCTAC TGCGTCACTG
```

FIG. 6C

3481 CGAACCGTCC CGCATCGCAC GCCTGATCGC TGTCGTCGCC GGCATCGCGG GCGTGTTGTT
     GCTTGGCAGG GCGTAGCGTG CGGACTAGCG ACAGCAGCGG CCGTAGCGCC CGCACAACAA

3541 GTGCGGTCTG GTTCCACTGC TCCCGGTGGA GGAGACCACC GCGACCGTCC TGTGGCCGCA
     CACGCCAGAC CAAGGTGACG AGGGCCACCT CCTCTGGTGG CGCTGGCAGG ACACCGGCGT

3601 GGGTGTGGGT GCCGACGGCA ACGTCACCGA ACTGACGGCG CCGCTGGTGG CCGGGGCGCC
     CCCACACCCA CGGCTGCCGT TGCAGTGGCT TGACTGCCGC GGCGACCACC GGCCCCGCGG

3661 GCGGGCACTC GACGTCACGA TCCCGTGCCG CGCCGTGGCC GAGCTTCCCG CCGACGGCGG
     CGCCCGTGAG CTGCAGTGCT AGGGCACGGC GCGGCACCGG CTCGAAGGGC GGCTGCCGCC

3721 CGTGGTGTTC TCGACGAACC CGGCAGGCGG CATCGAGGCC GGCCGCAACG GCATGTTCAT
     GCACCACAAG AGCTGCTTGG GCCGTCCGCC GTAGCTCCGG CCGGCGTTGC CGTACAAGTA

3781 CCGCGCCAAC GCCGACGTGG TCTACGTCGC GTTCCGCGAC ACGGTCGCCG GGTCGCACC
     GGCGCGGTTG CGGCTGCACC AGATGCAGCG CAAGGCGCTG TGCCAGCGGC CCAGCGTGG

3841 GCGTGAGGCC GTCGATTCCG GCGCGTGCAG TGAGATCCAC GTCTGGGCCG ACGTCAGCGC
     CGCACTCCGG CAGCTAAGGC CGCGCACGTC ACTCTAGGTG CAGACCCGGC TGCAGTCGCG

3901 GGTGGGCGCC GACTTCGCCG GTATCCCCGA CGCCAGCGGA ACCCTGCCCG TCGACAAGCG
     CCACCCGCGG CTGAAGCGGC CATAGGGGCT GCGGTCGCCT TGGGACGGGC AGCTGTTCGC

3961 CCCCCAGGTC TCGGGTGTCT TCACCGACCT CAAGGTGCCC GCGCAGCCCG GCCTGGCCGC
     GGGGGTCCAG AGCCCACAGA AGTGGCTGGA GTTCCACGGG CGCGTCGGGC CGGACCGGCG

4021 GCGCATCGAC ATCGACACCC GCTTCATCAC GTCACCGACC CTGCTGAAGA CCGCCGTGAT
     CGCGTAGCTG TAGCTGTGGG CGAAGTAGTG CAGTGGCTGG GACGACTTCT GGCGGCACTA

4081 GGTGCTCGGC CTCGCGTGCG TCATCGGGTC GATCGTCGCG CTGGCCCTGT TGGACCGCGG
     CCACGAGCCG GAGCGCACGC AGTAGCCCAG CTAGCAGCGC GACCGGGACA ACCTGGCGCC

4141 ATGGCGCAGG CGCCCNGCGC GCACGCGCGG ACGCGCCGGG CTGTGGACGT GGATCACCGA
     TACCGCGTCC GCGGGNCGCG CGTGCGCGCC TGCGCGGCCC GACACCTGCA CCTAGTGGCT

4201 CACCGGCGTG ATCGGCGGCC TGCTCATCTG GCACATCGTC GGCGCGCCCA CGTCCGACGA
     GTGGCCGCAC TAGCCGCCGG ACGAGTAGAC CGTGTAGCAG CCGCGCGGGT GCAGGCTGCT

4261 CGGCTACAAC ATGACCATCG CCCGGGTGGC GTCCGAGGCG GGTTACACGA CGAACTACTA
     GCCGATGTTG TACTGGTAGC GGGCCCACCG CAGGCTCCGC CCAATGTGCT GCTTGATGAT

4321 CCGCTACTTC GGCGCGTCCG AGGCCCCGTT CGACTGGTAC CAGAGCGTGC TGTCGCACCT
     GGCGATGAAG CCGCGCAGGC TCCGGGGCAA GCTGACCATG GTCTCGCACG ACAGCGTGGA

4381 GGCCTCGATC AGCACCGCGG GCGTGTGGAT GCGGCTGCCC GCCACGGCGG CCGCTATCGC
     CCGGAGCTAG TCGTGGCGCC CGCACACCTA CGCCGACGGG CGGTGCCGCC GGCGATAGCG

4441 GACGTGGCTG ATCATCAGCC GCTGCGTGCT GCCCCGCATC GGCAGGCGCG TCGCGGCCAA
     CTGCACCGAC TAGTAGTCGG CGACGCACGA CGGGGCGTAG CCGTCCGCGC AGCGCCGGTT

4501 CCGCGTCGCG ATGCTCACCG CGGGTGCGAC GTTCCTGGCC GCGTGGCTGC CGTTCAACAA
     GGCGCAGCGC TACGAGTGGC GCCCACGCTG CAAGGACCGG CGCACCGACG GCAAGTTGTT

4561 CGGTTTGCGT CCCGAACCGC TGATCGCGTT CGCGGTGATC ACGGTGTGGA TGCTGGTGGA
     GCCAAACGCA GGGCTTGGCG ACTAGCGCAA GCGCCACTAG TGCCACACCT ACGACCACCT

4621 GAACTCCATC GGCACGCGGC GCCTGTGGCC CGCGGCCGTC GCGATCGTCA TCGCGATGTT
     CTTGAGGTAG CCGTGCGCCG CGGACACCGG CGCCGGCAG CGCTAGCAGT AGCGCTACAA

FIG. 6D

| | | | | | |
|---|---|---|---|---|---|
| 4681 | CTCCGTCACA | CTCGCCCCGC | AGGGCCTGAT | CGCGCTGGCG | CCGCTGCTGG TCGGCGCGCG |
| | GAGGCAGTGT | GAGCGGGGCG | TCCCGGACTA | GCGCGACCGC | GGCGACGACC AGCCGCGCGC |
| 4741 | CGCCATCGGC | CGCGTCGTCA | CCGCCCGCCG | TGCGGCACCG | GGATCCTGGC GTCCCTGCCC |
| | GCGGTAGCCG | GCGCAGCAGT | GGCGGGCGGC | ACGCCGTGGC | CCTAGGACCG CAGGGACGGG |
| 4801 | GCTCGCGGCG | TCGGTCGCCG | TGGTCTTCGT | GATCATCTTC | CGCGATCAGA CCCTGGCCAC |
| | CGAGCGCCGC | AGCCAGCGGC | ACCAGAAGCA | CTAGTAGAAG | GCGCTAGTCT GGGACCGGTG |
| 4861 | GGTCGCCGAG | TCGGTGCGCA | TCAAGTACGT | CGTGGGACCG | ACCATCCCCT GGTACCAGGA |
| | CCAGCGGCTC | AGCCACGCGT | AGTTCATGCA | GCACCCTGGC | TGGTAGGGGA CCATGGTCCT |
| 4921 | ATTCCTGCGG | TACTACTTCC | TCACGGTCGA | GGACAGCGTC | GACGGATCCC TGACCCGCCG |
| | TAAGGACGCC | ATGATGAAGG | AGTGCCAGCT | CCTGTCGCAG | CTGCCTAGGG ACTGGGCGGC |
| 4981 | ATTCGCGGTG | CTGGTGCTGC | TGCTGTGCCT | GTTCGGCCTC | ATCATGGTGC TGCTGCGCCG |
| | TAAGCGCCAC | GACCACGACG | ACGACACGGA | CAAGCCGGAG | TAGTACCACG ACGACGCGGC |
| 5041 | CGGCCGGGTG | CCCGGCGCGG | TGAGCGGGCC | GCTGTGGCGG | CTGTGCGGAT CGACCGCGAT |
| | GCCGGCCCAC | GGGCCGCGCC | ACTCGCCCGG | CGACACCGCC | GACACGCCTA GCTGGCGCTA |
| 5101 | CGGCCTGCTG | CTGTTGATCC | TCACCCCCAC | CAAGTGGGCG | ATCCAGTTCG GCGCGTTCGC |
| | GCCGGACGAC | GACAACTAGG | AGTGGGGGTG | GTTCACCCGC | TAGGTCAAGC CGCGCAAGCG |
| 5161 | GGGCCTGGCC | GGCGCCCTCG | GTGGTGTGAC | GGCATTCGCG | TTCGCGCGCG TGGGCCTGCA |
| | CCCGGACCGG | CCGCGGGAGC | CACCACACTG | CCGTAAGCGC | AAGCGCGCGC ACCCGGACGT |
| 5221 | CAGCCGACGC | AACCTCGCGC | TGTACGTCAC | CGCGCTGCTG | TTCATCCTGG CGTGGGCCAC |
| | GTCGGCTGCG | TTGGAGCGCG | ACATGCAGTG | GCGCGACGAC | AAGTAGGACC GCACCCGGTG |
| 5281 | CTCGGGCCTC | AACGGCTGGT | TCTACGTCGG | CAACTACGGC | GTGCCGTGGT TCGACAAGCA |
| | GAGCCCGGAG | TTGCCGACCA | AGATGCAGCC | GTTGATGCCG | CACGGCACCA AGCTGTTCGT |
| 5341 | GCCTGTGATC | GCGCATTACC | CGGTCACCAC | GATCTTCCTG | GTGCTCGCGA TCGTCGGCGG |
| | CGGACACTAG | CGCGTAATGG | GCCAGTGGTG | CTAGAAGGAC | CACGAGCGCT AGCAGCCGCC |
| 5401 | TCTGCTCGCA | GGCTGGCTGC | ACTTCCGCAT | GGACTACGCG | GGGCACACCG AGGTGGCCGA |
| | AGACGAGCGT | CCGACCGACG | TGAAGGCGTA | CCTGATGCGC | CCCGTGTGGC TCCACCGGCT |
| 5461 | CACCGGCAGA | AACCGCGCGC | TCGCCTCGAC | GCCGCTGTTG | ATCGTCGCGA CCATCATGGT |
| | GTGGCCGTCT | TTGGCGCGCG | AGCGGAGCTG | CGGCGACAAC | TAGCAGCGCT GGTAGTACCA |
| 5521 | GGTGCTCGAA | CTCGGCTCGA | TGGTCAAGGC | CACCGTGGGC | CGCTACCCCG TCTACACCGT |
| | CCACGAGCTT | GAGCCGAGCT | ACCAGTTCCG | GTGGCACCCG | GCGATGGGGC AGATGTGGCA |
| 5581 | GGGCTCGGCC | AACATCGCCG | CGCTGCGCTC | GGCCGGCGAC | AGCTGTGCGA TGGCCGACGC |
| | CCCGAGCCGG | TTGTAGCGGC | GCGACGCGAG | CCGGCCGCTG | TCGACACGCT ACCGGCTGCG |
| 5641 | CGTGCTGGTC | GAGGCCGACC | CCAACGAGGG | CATGCTGCAA | CCGGTTCCGG GCCAGCGGTT |
| | GCACGACCAG | CTCCGGCTGG | GGTTGCTCCC | GTACGACGTT | GGCCAAGGCC CGGTCGCCAA |
| 5701 | CGGTGACTAC | GGCCCGCTGG | GCGGCGAGGA | CCCCGTCGGC | TTCACCCCCA GCGGCGTCAG |
| | GCCACTGATG | CCGGGCGACC | CGCCGCTCCT | GGGGCAGCCG | AAGTGGGGGT CGCCGCAGTC |
| 5761 | CGAACACCTC | GAACCCGAGC | CCGTCGGGAC | CAACCCGGGC | ACCCCGAACT CCGAGGGGCC |
| | GCTTGTGGAG | CTTGGGCTCG | GGCAGCCCTG | GTTGGGCCCG | TGGGGCTTGA GGCTCCCCGG |
| 5821 | GGTCGACAAG | CCCAACATCG | GTATCGCCTA | CGCCGGGGAC | ACCGGCGGCG GCTACGCCCC |
| | CCAGCTGTTC | GGGTTGTAGC | CATAGCGGAT | GCGGCCCCTG | TGGCCGCCGC CGATGCGGGG |

FIG. 6E

```
5881  CGAGGGCGTC AACGGGTCGC GGGTGTTCCT GCCCTTCGGC CTGGACCCGT CCCGCACCCC
      GCTCCCGCAG TTGCCCAGCG CCCACAAGGA CGGGAAGCCG GACCTGGGCA GGGCGTGGGG

5941  GGTGATGGGC AGCTACGGCG AGAACAAGCT GGCCGCCAAG GCCACGTCGG CCTGGTACCA
      CCACTACCCG TCGATGCCGC TCTTGTTCGA CCGGCGGTTC GGTGCAGCC GGACCATGGT

6001  GCTGCCGCCC CGCACGCCGG ACCGCCGCT GGTGACCGTC GCCGCGGCAG GCGCCATCTG
      CGACGGCGGG GCGTGCGGCC TGGCGGGCGA CCACTGGCAG CGGCGCCGTC GCGGTAGAC

6061  GTACTACGAG GAAGACGGCT CGTTCAACTA CGGCCAGTCG CTCAAGCTGC AGTGGGGTGT
      CATGATGCTC CTTCTGCCGA GCAAGTTGAT GCCGGTCAGC GAGTTCGACG TCACCCCACA

6121  GCACCGGCCC GACGGCACCT ACCAGGCGCT GTCGGAGGTC CAGCCCATCG ACATCTTCCA
      CGTGGCCGGG CTGCCGTGGA TGGTCCGCGA CAGCCTCCAG GTCGGGTAGC TGTAGAAGGT

6181  GCAGAAGGCG TGGCGCAACC TGCGGTTCCC GCTCGCGTGG GCGCCGCCGG AGGCCAACGT
      CGTCTTCCGC ACCGCGTTGG ACGCCAAGGG CGAGCGCACC CGCGGCGGCC TCCGGTTGCA

6241  CGCGCGCATC GTCGCCGACG ACCCCAACCT GTCCGAGGAC CAGTGGTGCG CGTTCACGCC
      GCGCGCGTAG CAGCGGCTGC TGGGGTTGGA CAGGCTCCTG GTCACCACGC GCAAGTGCGG

6301  GCCGCGCGTT CCGGTGCTGC AGACCGCGCA GCAGTTCCTC GGATCGCAGA CCCCGGTGCT
      CGGCGCGCAA GGCCACGACG TCTGGCGCGT CGTCAAGGAG CCTAGCGTCT GGGGCCACGA

6361  CATGGACATC GCCACGGCCG CGAACTTCCC GTGCCAGCGG CCATTCGCCG AGCGGCTCGG
      GTACCTGTAG CGGTGCCGGC GCTTGAAGGG CACGGTCGCC GGTAAGCGGC TCGCCGAGCC

6421  TGTTGCCGAG TTGCCCGAGT ACCGCATCAT CCCCAACTTC AAGCAGATGG TGGTGTCGTC
      ACAACGGCTC AACGGGCTCA TGGCGTAGTA GGGGTTGAAG TTCGTCTACC ACCACAGCAG

6481  CAACCAGTGG CAGTCCGCCG CCGACGGTGG GCCGTTCCTG TTCATCCAGG CGCTGCTGAG
      GTTGGTCACC GTCAGGCGGC GGCTGCCACC CGGCAAGGAC AAGTAGGTCC GCGACGACTC

6541  GACCGAGGCG ATCCCGACCT ATCTGCGTGA CGACTGGTAC CGCGACTGGG GCTCGATCGA
      CTGGCTCCGC TAGGGCTGGA TAGACGCACT GCTGACCATG GCGCTGACCC CGAGCTAGCT

6601  GCGCTACATC CGGGTGGTAC CGCAGGAGCA GGCGCCCACA GCCGCCATCG AGGAAGGATC
      CGCGATGTAG GCCCACCATG GCGTCCTCGT CCGCGGGTGT CGGCGGTAGC TCCTTCCTAG

6661  GACGCGAGTG TTCGGATGGA GTCGCGGCGG ACCGATCAGG GCACTGCCGT GAGCGGCAAC
      CTGCGCTCAC AAGCCTACCT CAGCGCCGCC TGGCTAGTCC CGTGACGGCA CTCGCCGTTG

6721  ATGGATGAAG CCGTGAGCGG CAACATGGAT GAAGCCGTGA GCGCCGGCAA GGACGTGCGG
      TACCTACTTC GGCACTCGCC GTTGTACCTA CTTCGGCACT CGCGGCCGTT CCTGCACGCC

6781  ATCGCACGCT GGGTCGCCAC CATCGCGGGC CTGCTCGGAT TCGTGCTCTC CGTGTCCATC
      TAGCGTGCGA CCCAGCGGTG GTAGCGCCCG GACGAGCCTA AGCACGAGAG GCACAGGTAG

6841  CCGCTGCTGC CGGTCACGCA GACCACGGCC ACGCTGAACT GGCCGCAGCA GGGCAGGCTC
      GGCGACGACG GCCAGTGCGT CTGGTGCCGG TGCGACTTGA CCGGCGTCGT CCCGTCCGAG

6901  GACAACGTCA CCGCTCCGCT GATCTCGCAG GCCCCGTTGG AGCTGACCGC GACCGTGCCG
      CTGTTGCAGT GGCGAGGCGA CTAGAGCGTC CGGGGCAACC TCGACTGGCG CTGGCACGGC

6961  TGCTCGGTGG TGCGCGACCT GCCCCCCGAG GGCGGCCTGG TGTTCGGCAC CGCACCCGCC
      ACGAGCCACC ACGCGCTGGA CGGGGGGCTC CCGCCGGACC ACAAGCCGTG GCGTGGGCGG

7021  GAGGGCCGCG ACGCCGCACT CAACGCGATG CTGGTCAACG TCACCGAGAC CCGCGTCGAC
      CTCCCGGCGC TGCGGCGTGA GTTGCGCTAC GACCAGTTGC AGTGGCTCTG GGCGCAGCTG
```

FIG. 6F

```
7081  GTGATCGTGC GCAACGTCGT CGTCGCGAGC GTGAACCGCG ACCGCGTCGC GGGACCTGAC
      CACTAGCACG CGTTGCAGCA GCAGCGCTCG CACTTGGCGC TGGCGCAGCG CCCTGGACTG

7141  TGCCAACGCA TCGAGATCAC GTCGAACCTG GATGGCACCT ACGCCGATTT CGTCGGTCTC
      ACGGTTGCGT AGCTCTAGTG CAGCTTGGAC CTACCGTGGA TGCGGCTAAA GCAGCCAGAG

7201  ACACAGATTT CCGGTGAGGA CGCGGGCAAG CTGCAGCGCA CCGGCTACCC CGACCCGAAT
      TGTGTCTAAA GGCCACTCCT GCGCCCGTTC GACGTCGCGT GGCCGATGGG GCTGGGCTTA

7261  CTGCGGCCCG CGATCGTCGG TGTGTTCACC GACCTCACCG GCCCTGCGCC GCAGGGACTG
      GACGCCGGGC GCTAGCAGCC ACACAAGTGG CTGGAGTGGC CGGGACGCGG CGTCCCTGAC

7321  TCGGTGTCGG CGGAGATCGA CACGCGCTTC ACGACGCACC CCACGGCGCT CAAGCTCGCG
      AGCCACAGCC GCCTCTAGCT GTGCGCGAAG TGCTGCGTGG GGTGCCGCGA GTTCGAGCGC

7381  GCCATGCTGC TGGCGATCGT GTCGACCGTC ATCGCGCTGC TCGCGCTGTG GCGCCTCGAC
      CGGTACGACG ACCGCTAGCA CAGCTGGCAG TAGCGCGACG AGCGCGACAC CGCGGAGCTG

7441  CGGCTCGACG GGCGGCGCAT GCACCGCCTG ATCCCGACGC GCTGGCGCAC GGTCACCGCG
      GCCGAGCTGC CCGCCGCGTA CGTGGCGGAC TAGGGCTGCG CGACCGCGTG CCAGTGGCGC

7501  GTCGACGGCG TGGTGGTCGG CGGCATGGCG ATCTGGTACG TGATCGGCGC CAACTCGTCC
      CAGCTGCCGC ACCACCAGCC GCCGTACCGC TAGACCATGC ACTAGCCGCG GTTGAGCAGG

7561  GACGACGGCT ACATCCTGCA GATGGCGCGC ACGGCCGAGC ACGCGGGCTA CATGGCGAAC
      CTGCTGCCGA TGTAGGACGT CTACCGCGCG TGCCGGCTCG TGCGCCCGAT GTACCGCTTG

7621  TACTTCCGCT GGTTCGGCAG CCCCGAGGAC CCGTTCGGCT GGTACTACAA CGTGCTGGCG
      ATGAAGGCGA CCAAGCCGTC GGGGCTCCTG GGCAAGCCGA CCATGATGTT GCACGACCGC

7681  CTCATGACCA AGGTGAGCGA CGCCAGCATC TGGATCCGAT TGCCCGACTT GATCTGTGCC
      GAGTACTGGT TCCACTCGCT GCGGTCGTAG ACCTAGGCTA ACGGGCTGAA CTAGACACGG

7741  CTGATCTGCT GGCTGCTGCT GTCCCGTGAG GTGCTGCCGC GGCTGGGACC CGCGGTGGCC
      GACTAGACGA CCGACGACGA CAGGGCACTC CACGACGGCG CCGACCCTGG GCGCCACCGG

7801  GGCAGTCGCG CGGCGATGTG GGCCGCGGGC CTGGTGCTGC TTGGTGCGTG GATGCCGTTC
      CCGTCAGCGC GCCGCTACAC CCGGCGCCCG GACCACGACG AACCACGCAC CTACGGCAAG

7861  AACAACGGCC TGCGCCCCGA GGGCCAGATC GCCACGGGCG CGCTGATCAC CTATGTCCTG
      TTGTTGCCGG ACGCGGGGCT CCCGGTCTAG CGGTGCCCGC GCGACTAGTG GATACAGGAC

7921  ATCGAACGCG CCGTCACCTC GGGCCGGCTC ACCCCGGCGG CGCTGGCCAT CACGACGGCC
      TAGCTTGCGC GGCAGTGGAG CCCGGCCGAG TGGGGCCGCC GCGACCGGTA GTGCTGCCGG

7981  GCGTTCACGC TCGGTATCCA GCCGACCGGT CTGATCGCCG TCGCCGCACT GCTGGCCGGT
      CGCAAGTGCG AGCCATAGGT CGGCTGGCCA GACTAGCGGC AGCGGCGTGA CGACCGGCCA

8041  GGCCGTCCGA TCCTGCGCAT CGTCATCCGC CGCCGTCGCC TCGACGGGAC CTGGCCGCTG
      CCGGCAGGCT AGGACGCGTA GCAGTAGGCG GCGGCAGCGG AGCTGCCCTG GACCGGCGAC

8101  ATCGCGCCAC TGCTGGCCGC GGGCACCGTG ATCCTGGCCG TGGTGTTCGC CGACCAGACC
      TAGCGCGGTG ACGACCGGCG CCCGTGGCAC TAGGACCGGC ACCACAAGCG GCTGGTCTGG

8161  ATCGCAACGG TGCTGGAGGC CACCAGGATC CGCACCGCGA TCGGGCCCAG CCAGGAGTGG
      TAGCGTTGCC ACGACCTCCG GTGGTCCTAG GCGTGGCGCT AGCCCGGGTC GGTCCTCACC

8221  TGGACCGAGA AGCTGCGCTA CTACTACCTG ATCCTGCCGA CCACCGACGG CGCGATCTCG
      ACCTGGCTCT TCGACGCGAT GATGATGGAC TAGGACGGCT GGTGGCTGCC GCGCTAGAGC
```

FIG. 6G

```
8281  CGGCGCGTGG CGTTCGTGTT CACCGCGATG TGCCTGTTCC CCTCGCTGTT CATGATGTTG
      GCCGCGCACC GCAAGCACAA GTGGCGCTAC ACGGACAAGG GGAGCGACAA GTACTACAAC

8341  CGGCGCAAGC ACATCGCGGG CGTCGCACGC GGCCCGGCCT GGCGCCTAAT GGGCATCATC
      GCCGCGTTCG TGTAGCGCCC GCAGCGTGCG CCGGGCCGGA CCGCGGATTA CCCGTAGTAG

8401  TTCGCCACCA TGTTCTTCCT GATGTTCACG CCCACCAAGT GGACCCACCA CTTCGGCCTG
      AAGCGGTGGT ACAAGAAGGA CTACAAGTGC GGGTGGTTCA CCTGGGTGGT GAAGCCGGAC

8461  TTCGCCGCGG TGGGCGGTGC GATGGCCGCG CTGGCGACCG TGCTGGTGTC GCCCACGGTG
      AAGCGGCGCC ACCCGCCACG CTACCGGCGC GACCGCTGGC ACGACCACAG CGGGTGCCAC

8521  CTGCGCTCGG CGCGCAACCG GATGGCGTTC CTGTCGCTCG TGTTGTTCGT GCTGGCGTTC
      GACGCGAGCC GCGCGTTGGC CTACCGCAAG GACAGCGAGC ACAACAAGCA CGACCGCAAG

8581  TGCTTCGCCT CCACCAACGG CTGGTGGTAC GTGTCGAACT TCGGTGCGCC GTTCAACAAT
      ACGAAGCGGA GGTGGTTGCC GACCACCATG CACAGCTTGA AGCCACGCGG CAAGTTGTTA

8641  TCGGTGCCCA AGGTCGGCGG TGTCCAGATC AGCGCGATCT TCTTCGCGCT GTCGGCGATC
      AGCCACGGGT TCCAGCCGCC ACAGGTCTAG TCGCGCTAGA AGAAGCGCGA CAGCCGCTAG

8701  GCGGCCCTGT GGGCGTTCTG GTTGCACCTG ACGCGTCGCA CCGAATCCCG TGTGGTGGAC
      CGCCGGGACA CCCGCAAGAC CAACGTGGAC TGCGCAGCGT GGCTTAGGGC ACACCACCTG

8761  CGGTTGACCG CGGCGCCCAT CCCCGTCGCG GCCGGGTTCA TGGTCGTGGT GATGATGGCG
      GCCAACTGGC GCCGCGGGTA GGGGCAGCGC CGGCCCAAGT ACCAGCACCA CTACTACCGC

8821  TCCATGGCGA TCGGCGTGGT GCGCCAGTAC CCGACGTACT CCAACGGGTG GCCAACATC
      AGGTACCGCT AGCCGCACCA CGCGGTCATG GCTGCATGA GGTTGCCCAC CCGGTTGTAG

8881  CGCGCGTTCG CGGGCGGTTG CGGCCTGGCC GACGACGTTC TGGTGGAACC GGATTCGAAC
      GCGCGCAAGC GCCCGCCAAC GCCGGACCGG CTGCTGCAAG ACCACCTTGG CCTAAGCTTG

8941  GCGGGCTTCC TCACGCCGCT GCCCGGCGCG TACGGTCCGC TTGGCCCGCT GGGCGGCGAG
      CGCCCGAAGG AGTGCGGCGA CGGGCCGCGC ATGCCAGGCG AACCGGGCGA CCCGCCGCTC

9001  GACCCGCAGG GCTTCTCCCC CGACGGTGTT CCCGACCGCA TCATCGCCGA GGCCATCCGC
      CTGGGCGTCC CGAAGAGGGG GCTGCCACAA GGGCTGGCGT AGTAGCGGCT CCGGTAGGCG

9061  CTCAACAATC CGCAGCCGGG CACCGATTAC GACTGGAACC GACCGATCAA GCTCGACGAG
      GAGTTGTTAG GCGTCGGCCC GTGGCTAATG CTGACCTTGG CTGGCTAGTT CGAGCTGCTC

9121  CCGGGCATCA ACGGTTCCAC CGTGCCGCTG CCCTACGGCC TCGACCCGAA GCGGGTTCCG
      GGCCCGTAGT TGCCAAGGTG GCACGGCGAC GGGATGCCGG AGCTGGGCTT CGCCCAAGGC

9181  GTCGCGGGTA CGTACTCCAC CGAGGCGCAA CAGGAGAGCA GGCTGTCCTC GGCGTGGTAC
      CAGCGCCCAT GCATGAGGTG GCTCCGCGTT GTCCTCTCGT CCGACAGGAG CCGCACCATG

9241  GAGCTTCCAG CCCGCGACGA GACCGAACGG GCTGCGCATC CGCTGGTGGT CATCACCGCC
      CTCGAAGGTC GGGCGCTGCT CTGGCTTGCC CGACGCGTAG GCGACCACCA GTAGTGGCGG

9301  GCGGGCACCA TCACCGGCGA GAGCGTCGCC AACGGCCTGA CGACCGGCCA GACCGTGGAC
      CGCCCGTGGT AGTGGCCGCT CTCGCAGCGG TTGCCGGACT GCTGGCCGGT CTGGCACCTG

9361  CTGGAGTACG CGACCCGCGG CCCGGACGGC ACCCTGGTGC CGCGGGCCG GGTGACACCG
      GACCTCATGC GCTGGGCGCC GGGCCTGCCG TGGGACCACG GCGCCCGGC CCACTGTGGC

9421  TACGACGTGG GGCCCACCCC GTCGTGGCGC AACCTGCGCT ACCCGCGCTC GGAGATCCCC
      ATGCTGCACC CCGGGTGGGG CAGCACCGCG TTGGACGCGA TGGGCGCGAG CCTCTAGGGG
```

FIG. 6H

```
9481    GACGATGCCG  TCGCGGTGCG  CGTGGTGGCC  GAGGATCTGT  CACTGAGCCA  GGGCGACTGG
        CTGCTACGGC  AGCGCCACGC  GCACCACCGG  CTCCTAGACA  GTGACTCGGT  CCCGCTGACC

9541    ATCGCGGTGA  CCCCGCCGCG  GGTGCCCGAG  CTGCAGTCGG  TGCAGGAGTA  CGTCGGCTCC
        TAGCGCCACT  GGGGCGGCGC  CCACGGGCTC  GACGTCAGCC  ACGTCCTCAT  GCAGCCGAGG

9601    GATCAGCCCG  TGCTGATGGA  CTGGGCCGTG  GGTCTGGCGT  TCCCGTGCCA  GCAGCCCATG
        CTAGTCGGGC  ACGACTACCT  GACCCGGCAC  CCAGACCGCA  AGGGCACGGT  CGTCGGGTAC

9661    CTGCACGCCA  ACGGCGTCAC  CGAGGTGCCC  AAGTTCCGCA  TCTCGCCGGA  CTACTACGCC
        GACGTGCGGT  TGCCGCAGTG  GCTCCACGGG  TTCAAGGCGT  AGAGCGGCCT  GATGATGCGG

9721    AAGCTGCAGA  GCACCGACAC  GTGGCAGGAC  GGCATCAACG  GCGGCCTGCT  GGGCATCACC
        TTCGACGTCT  CGTGGCTGTG  CACCGTCCTG  CCGTAGTTGC  CGCCGGACGA  CCCGTAGTGG

9781    GACCTGCTGC  TGCGGGCCTC  GGTGATGTCG  ACCTACCTGT  CGCAGGACTG  GGCCAGGAC
        CTGGACGACG  ACGCCCGGAG  CCACTACAGC  TGGATGGACA  GCGTCCTGAC  CCCGGTCCTG

9841    TGGGGTTCGT  TGCGCAAGTT  CGACACCGTC  GTCGAAGCGA  CGCCTGCCGA  ACTCGATTTC
        ACCCCAAGCA  ACGCGTTCAA  GCTGTGGCAG  CAGCTTCGCT  GCGGACGGCT  TGAGCTAAAG

9901    GGCTCCCAGA  CCCACAGCGG  TCTCTACAGC  CCGGGGCCTT  TGCGCATCCG  ACCTTGACAT
        CCGAGGGTCT  GGGTGTCGCC  AGAGATGTCG  GGCCCCGGAA  ACGCGTAGGC  TGGAACTGTA
```

FIG. 6I

EMBCAB OPERON OF MYCOBACTERIA AND MUTANTS THEREOF

STATEMENT OF GOVERNMENT INTEREST

This invention was made with government support under NIH Grant Nos. AI-37004 and AI-37015. As such, the government has certain rights in this invention.

BACKGROUND OF THE INVENTION

This invention is based upon the discovery by the inventors of the embC, embA, and embB genes that comprise the embCAB operon, and novel proteins encoded by the embCAB operon which are associated with the biosynthesis of the mycobacterial cell wall and are involved in resistance to the antimycobacterial drug ethambutol (EMB). The discovery of the embCAB operon and the proteins encoded by the operon will have important implications in the diagnosis and treatment of drug-resistant mycobacterial strains.

EMB is a selective antimycobacterial drug recommended for clinical use in 1996 (Karlson, A. G., Am Rev Resp Dis 84, 905–906 (1961)). Today, EMB remains an important component of tuberculosis treatment programs. Unfortunately, resistance to ethambutol has been described in 2–4% of clinical isolates of M. tuberculosis in the USA and other countries, and is prevalent among isolates from patients with multidrug-resistant tuberculosis (Bloch, A B., Cauthen, G M., Onorato, I M., et al. Nationwide survey of drug-resistant tuberculosis in the United States. JAMA 271, 665–671 (1994)).

EMB targets the mycobacterial cell wall, a unique structure among prokaryotes which consists of an outer layer of mycolic acids covalently bound to peptidoglycan via the arabinogalactan (Besra, G. S. & Chatterjee, D. in Tuberculosis. Pathogenesis, protection, and control (ed Bloom, B. R.) 285–306 (ASM Press, Washington D.C., 1994)). Lipoarabinomannan, another cell wall component of significant biological importance, shares with arabinogalactan the overall structure of the arabinan polymer (Chatterjee, D., et al., J. Biol Chem 266, 9652–9660 (1991)).

EMB inhibits the in vivo conversion of $[^{14}C]$glucose into cell wall arabinan (Takayama, K. & Kolburn, J. O., Antimicrob Agents Chemother 33, 143–1499 (1989)), and results in the accumulation of the lipid carrier decaprenyl-P-arabinose (Wolucka, B. A., et al., J Biol Chem 269, 23328–23335 (1994)), which suggest that the drug interferes with the transfer of arabinose to the cell wall acceptor. The synthesis of lipoarabinomannan is also inhibited in the presence of EMB (Deng, L., et al. Antimicrob Agents Chemother 39, 694–701 (1995)), (Mikusova, K., et al., Antimicrob Agents Chemother 39, 2484–2489 (1995)); again, this indicates a specific effect on arabinan biosynthesis.

Thus, there is a need for the identification and characterization of new target genes and proteins in strains of mycobacteria that exhibit resistance to drugs. This would require the identification of genes that participate in the biosynthesis of the mycobacterial cell wall and the identification of mutants of these genes encoding proteins that confer resistance to drugs. Characterization of the molecular target(s) of EMB could provide information on targets for new chemotherapeutic agents, and facilitate development of diagnostic strategies for the detection of resistant strains of mycobacteria.

SUMMARY OF THE INVENTION

The present invention is directed to the nucleic acid sequences of the embCAB operon which encode the proteins comprising the target of action of M. tuberculosis, M. smegmatis and M. leprae for ethambutol (EMB). The present invention further provides for the identification, isolation, sequencing, and characterization of these nucleic acid sequences and proteins for which they encode.

The present invention specifically provides purified and isolated wild type nucleic acid sequences of the embC, embA, and embB genes which comprise the embCAB operon, as well as mutated forms of these genes. The present invention also provides one or more single-stranded nucleic acid probes which specifically hybridize to wild type nucleic acid sequences of the genes of the embCAB operon and to mutated nucleic acid sequences of the embCAB operon, and mixtures thereof, which may be formulated in kits, and used in the detection of drug resistant mycobacterial strains.

The present invention also provides purified active embCAB proteins encoded by the genes of the embCAB operon. Also provided are antibodies immunoreactive with the protein(s) expressed by the wild type genes of the embCAB operon, and analogues thereof, as well as antibodies immunoreactive with the protein(s) expressed by the mutated genes of the embCAB operon. Additional objects of the invention will be apparent from the description which follows.

BRIEF DESCRIPTION OF THE FIGURES

Figure 1A:
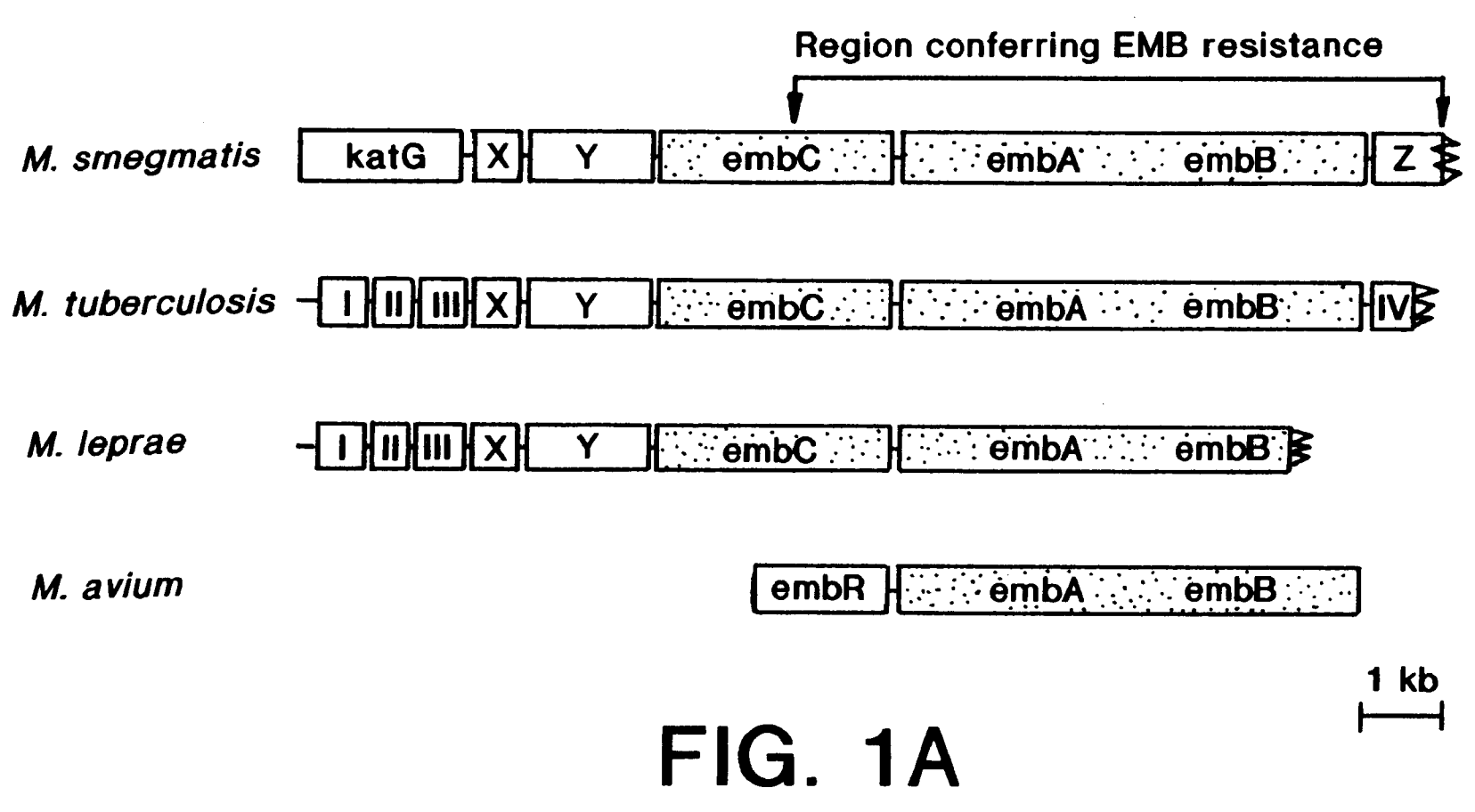

FIGS. 1A–1C: FIGS. 1A through 1C set forth the organization of the emb region of mycobacteria. FIG. 1A sets forth diagrammatical representations showing that M. smegmatis, M. tuberculosis, and M. leprae (GenBank accession numbers: U46844, U68480, L78821, and Z80343) present a conserved organization over a 14 kb region; three homologous emb genes preceded by a predicted coding region (Y), and by orfX, encoding a putative protein belonging to the short-chain alcohol dehydrogenase family (X). M. Avium (GenBank U66560) is an exception, as the region contains the embAB preceded by a putative regulator (embR) (Belanger, A. E. et al. Proc Natl Acad Sci USA 21, 11919–11924 (1996)). In M. smegmatis, the region is limited by the katG and by a putative transporter of the major facilitator family (Z). Corresponding areas in M. tuberculosis and M. leprae carry sequences encoding for hypothetical proteins (I–IV). FIG. 1B sets forth the results of a primer extension analysis. A definitive transcription start site (TSS) is present 51 bp upstream of M. smegmatis embC (a purine preceded by a high GC content −10 hexamer). No TSS was identified upstream of embA (*=start codon). A possible TSS was mapped downstream of the overlapping embA stop and embB putative start codon. FIG. 1C sets forth a diagrammatical representation of the secondary structure analysis of the EmbA, EmbC, and EmbB (EMBCAB) proteins. The EMBCAB are integral membrane proteins with 12 transmembrane domains and a C-terminal globular region of predicted periplasmic location. The proposed EMB resistance determining region in EmbB (ERDR), is marked.

FIG. 2 sets forth an alignment of the protein sequences of EMBCAB proteins (SEQ. ID. NOS:1–44). Mutations (*) in EMB-resistant M. smegmatis (Sm) and M. tuberculosis (Tb) involved EmbB amino acids in a highly conserved region. M. leprae (Lp) presents a glutamine at the conserved Ile-303 position. Av: M. avium.

FIG. 3 sets forth a schematic of the map of the embCAB operon as found in M. tuberculosis.

FIG. 4: FIG. 4 sets forth the nucleic acid sequence of the embCAB operon of M. tuberculosis (SEQ. ID. NO:45).

FIG. 3 sets forth a schematic of the map of the embCAB operon as found in M. smegmatis.

FIG. 6: FIG. 4 sets forth the nucleic acid sequence of the embCAB operon of *M. smegmatis* (SEQ. ID. NO:46).

FIG. 7 sets forth the results of automated DNA sequencing which indicates the exact missense mutations of codon 306 of the embb nucleic acid sequence. The sequence containing the missense mutation ATG is SEQ. ID. NO:47; GTG is SEQ. ID. NO:48; CTG is SEQ. ID. NO:49; ATA is SEQ. ID. NO:50; ATT is SEQ. ID. NO:51; and ATC is SEQ. ID. NO:52.

DETAILED DESCRIPTION OF THE INVENTION

Figure 1B:
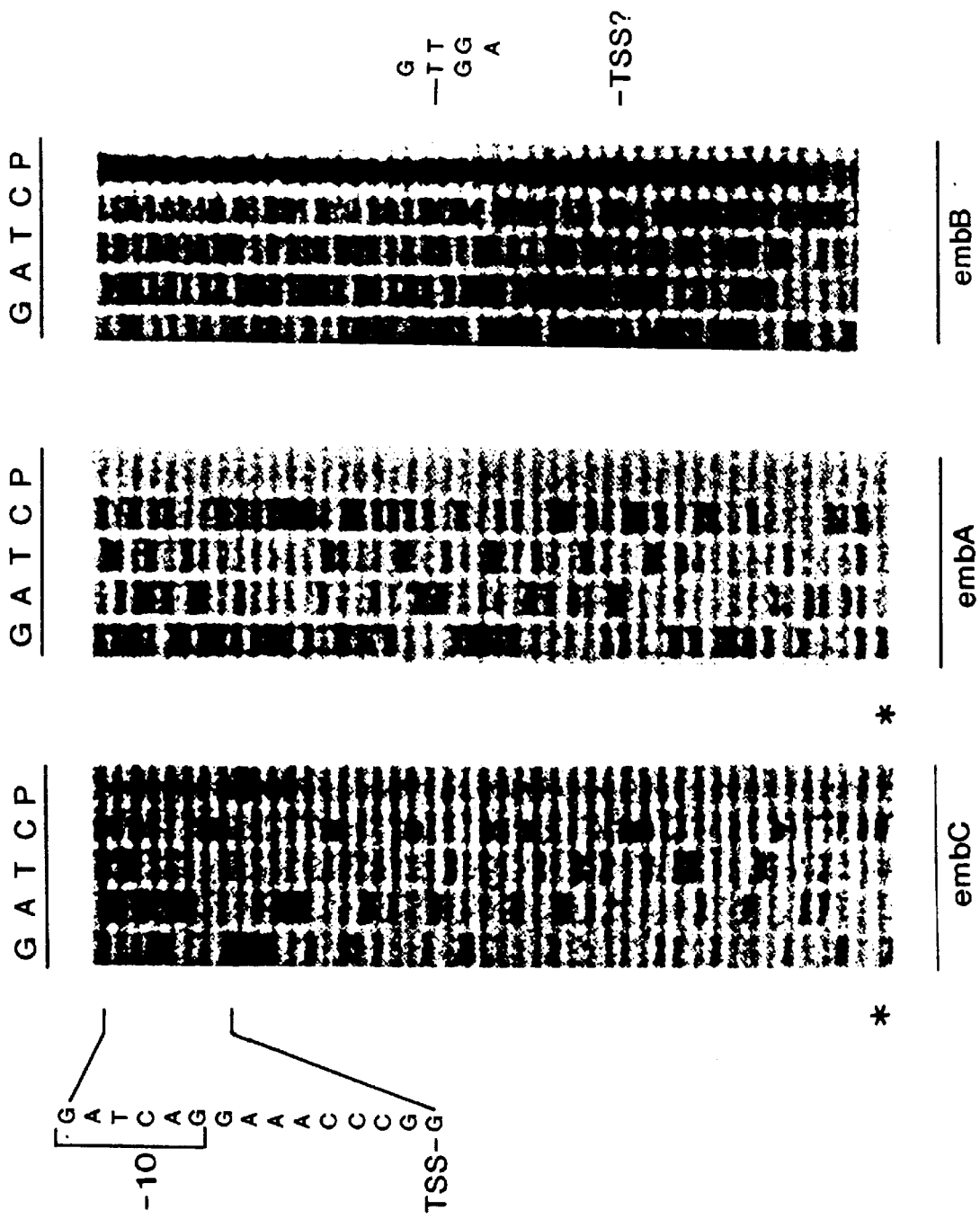

The present invention is directed to the nucleic acid sequences comprising the embCAB operon which encode the proteins comprising the target of action of *M. tuberculosis*, *M. smegmatis* and *M. leprae* for ethambutol (EMB).

The present invention specifically provides purified and isolated wild type nucleic acid sequences comprising the embCAB operon. Also provided are mutated forms of these nucleic acids, such as mutated forms of the embB gene of the embCAB operon. As used herein, an "operon" is a cluster of related genes that encode for open reading frames. The "embCAB operon" as used herein consists of the embC, embA and embB genes arranged in a single operon. The "wild type embCAB operon" is herein defined as the normal form of the embC, embA, and embB genes which express gene products, and includes degenerate forms. The "mutated embCAB operon" is the mutated form of the normal embCAB operon, which contains one or more deletions, insertions, point, substitution, nonsense, missense, polymorphism, or rearrangement mutations, or a combination thereof, that may render the gene products expressed by the mutated embCAB operon resistant to EMB. As used herein, "nucleic acid" may be genomic DNA, cDNA or RNA, and may be the entire nucleic acid sequence comprising the embC, embA, and embB genes, or any portion of the sequence thereof.

The present invention specifically provides for an embCAB nucleic acid sequence isolated from *M. tuberculosis*. This sequence is designated MTBEMB and is set forth in FIG. 4. The present invention also provides for an embCAB nucleic acid which encodes the amino acid sequence set forth in FIG. 2. The embCAB amino acid operon sequence is designated Themba, Thembc, and Thembb.

The present invention additionally provides for an embCAB nucleic acid sequence isolated from *M. smegmatis*. This sequence is designated MSMEMB2 and is set forth in FIG. 6. Also provided by the present invention is an embCAB nucleic acid sequence which encodes the amino acid sequence set forth FIG. 2. The embCAB amino acid operon sequence is designated Smemba, Smembc, and Smembb.

The present invention further provides for mutated nucleic acid sequences of the embCAB operon. In a preferred embodiment of the invention, a mutated nucleic acid sequence of the embCAB operon contains one or more mutations located in codon 306 of the embB nucleic acid sequence. These mutation(s) may be deletions, insertions, substitutions, missense, nonsense, point or rearrangement mutations, or a combination thereof. In a preferred embodiment of the invention, the mutation at codon 306 is a missense mutation. As used herein, a "missense" mutation is an alteration that changes a codon specific for one amino acid to a codon specific for another amino acid. Ordinarily, the wild type embB nucleic acid sequence encodes the amino acid methionine at position 306 (Met-306). In one embodiment of the invention, codon 306 of a mutated embB nucleic acid sequence is mutated to one the following: ATA, ATC or ATT, resulting in the encoding of an isoleucine at codon 306 instead of a methionine; GTG, resulting in the encoding of a valine instead of a methionine; and CTG, resulting in the encoding of a leucine instead of a methionine.

In one embodiment of the invention, a mutation is located in codon 303 of the nucleic acid sequence of the embB gene. Ordinarily, codon 303 of the wild type embB nucleic acid sequence encodes the amino acid isoleucine (Ile-303). In one embodiment of the invention, a mutated embB nucleic acid sequence at codon 303 encodes a phenylalanine instead of an isoleucine; in another, codon 303 encodes a glutamine instead of an isoleucine.

Other mutated embB nucleic acid sequences provided by the present invention include: a missense mutation of codon 285 wherein TTC is mutated to TTA, resulting in a change from phenylalanine to leucine; a missense mutation of codon 330 wherein TTC is mutated to GTC, resulting in a change from phenylalanine to valine; and a missense mutation of codon 630 wherein ACC is mutated to ATC, resulting in a change from threonine to isoleucine.

The present invention further provides a mutated nucleic acid sequence of the embCAB operon that contains one or more mutations located in the embC nucleic acid sequence. In a specific embodiment of the invention, an embC mutated nucleic acid sequence contains a polymorphism of nucleotide 195 resulting in a change from guanine to cytosine. This polymorphism results in the substitution of valine for leucine (Leu-195) in the embC nucleic acid sequence.

The present invention also provides a mutated nucleic acid sequence of the embCAB operon that contains one or more mutations located in the embA nucleic acid sequence. In a particular embodiment of the invention, an embA mutated nucleic acid sequence contains a substitution of guanine for adenine at nucleotide 2898 of embA. Another embodiment provides an embA mutated nucleic acid sequence which contains a missense mutation of codon 5 wherein GGT is mutated to AGT, and results in a change from glycine to serine.

It is to be understood that the present invention also provides for nucleic acid sequences wherein any or all of the above described mutations coexist in the embCAB operon in any combinations thereof.

The wild type and mutant nucleic acid sequences of the embCAB operon can be prepared several ways. For example, they can be prepared by isolating the nucleic acid sequences from a natural source, or by synthesis using recombinant DNA techniques. In addition, mutated nucleic acid sequences of the embCAB operon can be prepared using site mutagenesis techniques. The amino acid sequences may also be synthesized by methods commonly known to one skilled in the art (*Modern Techniques of Peptide and Amino Acid Analysis*, John Wiley & Sons (1981); M. Bodansky, *Principles of Peptide Synthesis*, Springer Verlag (1984)). Examples of methods that may be employed in the synthesis of the amino acids sequences, and mutants of these sequences include, but are not limited to, solid phase peptide synthesis, solution method peptide synthesis, and synthesis using any of the commercially available peptide synthesizers. The amino acid sequences, and mutants thereof, may contain coupling agents and protecting groups used in the synthesis of the protein sequences, and are well known to one of skill in the art.

The present invention also provides single-stranded nucleic acid probes and mixtures thereof for use in detecting drug resistance caused by a mutated nucleic acid of the embCAB operon. The nucleic acid probes may be DNA, cDNA, or RNA, and may be prepared from the mutated and/or wild type nucleic acid sequences comprising the embCAB operon. The probes may be the full length sequence of the nucleic acid sequences comprising the embCAB operon, or fragments thereof. Typical probes are 12 to 40 nucleotides in length. Generally, the probes are complementary to the embC, embA, or embB gene coding sequences, although probes to introns are also contemplated. The probes may be synthesized using an oligonucleotide synthesizer, and may be labeled with a detectable marker such as a fluorescence, enzyme or radiolabeled markers including $^{32}P$ and biotin, and the like. Combinations of two or more labeled probes corresponding to different regions of the embCAB operon also may be included in kits to allow for the detection and/or analysis of the embCAB operon by hybridization.

Specifically, the nucleic acid sequences of the embCAB operon may be used to produce probes capable of identifying the nucleic acids in mycobacteria which encode EMB resistance, which probes can be used in the identification, treatment and prevention of diseases caused by microorganisms, to assess the susceptibility of various mycobacterial strains to EMB, and to determine whether various drugs are effective against mycobacterial strains.

The present invention also provides purified active embCAB proteins, encoded by the embCAB operon. The proteins may be expressed by the wild type or mutated nucleic acid sequences of the embCAB operon, or an analogue thereof. As used herein, "analogue" means functional variants of the wild type protein, and includes embCAB proteins isolated from bacterial sources other then mycobacteria, as well as functional variants thereof. The proteins may also be isolated from native cells, or recombinantly produced.

The present invention also provides antibodies immunoreactive with the proteins expressed by the wild type embCAB operon, and analogues thereof, as well as antibodies immunoreactive with the proteins expressed by the mutated nucleic acid sequences of the embCAB operon. The antibodies may be polyclonal or monoclonal and are produced by standard techniques. The antibodies may be labeled with standard detectable markers (e.g. chemiluminescent detection systems and radioactive labels such as $^{125}I$) for detecting the wild type and mutated embCAB operons. The antibodies may also be presented in kits with detectable labels and other reagents and buffers for such detection.

The present invention also provides a method for detecting the presence of a microorganism exhibiting drug resistance in a subject, comprising detecting the presence of a mutated nucleic acid sequence of an embCAB operon of the subject. Specifically, the method determines whether a mycobacterium is resistant to ethambutol caused by a mutation in the nucleic acid sequence of the embCAB operon by detecting the presence of a mutated nucleic acid sequence of the embCAB operon in nucleic acid of the subject. The method may be used to determine whether persons in the population at large carry diseases resistant to drugs. This method is also useful for diagnosing drug resistant diseases. In a preferred embodiment of the invention, the nucleic acid sequences of the embCAB operons are identified and characterized to determine mycobacterial strains exhibiting resistance to EMB. In this embodiment, the nucleic acid probes employed in the method are mutant nucleic acid sequences of the embCAB operon. These mutant nucleic acid probes may contain one or more deletion, insertion, point, substitution, nonsense, polymorphism, missense, or rearrangement mutations. The mutant nucleic acid probes may be single-stranded, and labeled with a detectable marker.

Non-limiting examples of mycobacteria which can be tested for resistance using the method of the present invention include *Mycobacterium tuberculosis, Mycobacterium avium, Mycobacterium smegmatis, Mycobacterium bovis* BCG, *Mycobacterium leprae, Mycobacterium africanum*, and *Mycobacterium intracellulare*.

The presence of mutated nucleic acid sequences of the embCAB operon may be detected by procedures known to those skilled in the art including, but not limited to, standard nucleic acid sequencing techniques, restriction enzyme digestion analysis, hybridization with one or more probes hybridizable to the mutated and/or wild type sequences of the embCAB operon using standard procedures such as Southern Blot analysis, polymerase chain reaction using sense and antisense primers prepared from the mutated and/or wild type nucleic acid sequences of the embCAB operon, and combinations thereof.

The presence of the mutated nucleic acid sequences of the embCAB operon also may be detected by detecting expression of the protein product of the embCAB operon. Such expression products include both MRNA as well as the protein product itself. MRNA expression may be detected by standard sequencing techniques, hybridization with one or more probes hybridizable to the mutated and/or wild type embCAB operon mRNA using standard procedures such as Northern blot analysis, dot and slot hybridization, S1 nuclease assay, or ribonuclease protection assays, polymerase chain reaction using sense and antisense primers prepared from the mutated and/or wild type nucleic acid sequences of the embCAB operon, and combinations thereof. The protein may be detected using antibodies to the proteins expressed by the mutated embCAB operon and/or the wild type embCAB operon by procedures known in the art including, but not limited to, immunoblotting, immunoprecipitation, solid phase radioimmunoassay (e.g. competition RIAs, immobilized antigen or antibody RIAs, or double antibody RIAs), enzyme-linked immunoabsorbant assay, and the like.

The present invention also provides for a method of assessing the susceptibility of a mycobacterium to EMB in a clinical sample comprising isolating the mycobacterial chromosomal DNA from a clinical sample, preparing oligonucleotides utilizing the wild-type or mutant embCAB operon nucleic acid sequence, amplifying the region of the embCAB operon from the clinical sample, and determining whether a mutated embCAB operon exists in the mycobacterial strain in the clinical sample, the presence of a mutation indicating that the mycobacterial strain is resistant to EMB.

The mycobacteria that may be assessed by this method of the present invention include, but are not limited to, *Mycobacterium tuberculosis, Mycobacterium avium, Mycobacterium smegmatis, Mycobacterium bovis* BCG, *Mycobacterium leprae, Mycobacterium africanum*, and *Mycobacterium intracellulare*.

Non-limiting examples of clinical samples that may assessed by the methods of the present invention are urine, feces, blood, serum, mucus, cerebrospinal fluid, and any mixture thereof.

In a preferred embodiment of the invention, the determination of whether a mutation exists in the nucleic acid sequence of the embCAB operon is performed using single strand conformation polymorphism analysis.

The present invention also provides for a method of treating a mycobacterial infection in a subject by obtaining anti-DNA or anti-RNA nucleic acid sequences capable of inhibiting the mRNA activity of the embCAB operon of a mycobacterium, utilizing a wild type or the mutant nucleic acid of the embCAB operon; and administering an amount of said nucleic acid sequences, either alone or in combination with other compositions to treat the mycobacterial infection in a subject.

The anti-DNA or anti-RNA nucleic acid sequences employed in the method may be mutant or wild-type nucleic acid sequences of the embCAB operon. The mutant nucleic acid sequence may contain one or more deletions, insertions, substitutions, missense, nonsense, polymorphisms, point, or rearrangement mutations. The mutant nucleic acid sequence may be single-stranded, and labeled with a detectable marker.

Non-limiting examples of infections that can be treated using the methods of the present invention include those caused by mycobacteria selected from the group consisting of *Mycobacterium tuberculosis, Mycobacterium avium, Mycobacterium smegmatis, Mycobacterium bovis* BCG, *Mycobacterium leprae, Mycobacterium africanum*, and *Mycobacterium intracellulare*.

The nucleic acid sequences of the present invention are administered in conjunction with a suitable pharmaceutical carrier. Representative examples of suitable carriers include, but are not limited to, mineral oil, alum, and synthetic polymers. Vehicles for vaccines are well known in the art and the selection of a suitable vehicle is deemed to be within the scope of those skilled in the art from the teachings contained herein. The selection of a suitable vehicle is also dependent on the manner in which the nucleic acid sequences are to be administered. The nucleic acid sequences may be administered orally, enterally, subcutaneously, intraperitoneally, intravenously, or intranasally. Accordingly, as used herein, "subject" may be an embryo, fetus, newborn, infant, or adult. Further, as used herein "treating" is contacting a mycobacterium with the nucleic acids of the present invention, alone or in combination with other compositions.

The present invention additionally provides for the use of the nucleic acid sequences of the embCAB operon of the present invention as vaccines, or to improve existing vaccines.

Non-limiting examples of mycobacterial infections that can be treated using the vaccines of the present invention include those caused by mycobacteria selected from the group consisting of *Mycobacterium tuberculosis, Mycobacterium avium, Mycobacterium smegmatis, Mycobacterium bovis* BCG, *Mycobacterium leprae, Mycobacterium africanum*, and *Mycobacterium intracellulare*. For example, *M. tuberculosis* complex strains that are resistant to EMB often have reduced virulence and can be administered as vaccines. In addition, mutated genes of *M. tuberculosis* and *M. bovis* can be added to BCG or tuberculosis vaccines to provide attenuated mutant tuberculosis vaccines. These vaccines can be used to treat and prevent a wide variety of diseases, including tuberculosis, human immunodeficiency viral infection, polio, leprosy, malaria, tetanus, diphtheria, influenza, measles, mumps, hepatitis and rabies.

The present invention is described in the following Experimental Details Section, which is set forth to aid in an understanding of the invention, and should not be construed to limit in any way the invention as defined in the claims which follow thereafter.

Experimental Details Section

A. Materials and Methods

*M. smegmatis* mc$^2$6 (Snapper, S. B., Melton, R. E., Mustafa, S., Kieser, T. & Jacobs Jr., W. R. Isolation and characterization of efficient transformation mutants of *Mycobacterium smegmatis, Mol Microbiol* 4, 1911–1919 (1990)) isogenic mutants were selected on Middlebrook 7H11 (Difco Laboratories, Detroit Mich.) supplemented with oleic acid, bovine serum albumin, dextrose and catalase (OADC, Carr-Scarborough Microbiologicals) by stepwise exposure of $10^8$ bacteria to EMB [2,2'-(ethylenediimino)-di-1-butanol] (Sigman, Buchs, Switzerland). First level mutants, selected on plates containing EMB 2.5 μg ml$^{-1}$, were replated on EMB 20 μg ml$^{-1}$ to obtain second level mutants. Highly resistant (third level) mutants were obtained by plating second level mutants onto EMB 100 μg ml$^{-1}$. Minimum inhibitory concentrations (MICs), indicating the minimal concentration of an antibiotic that must be achieved at the site of infection to inhibit the growth of the microorganism, were determined in microtiter plates containing Middlebrook 7H9/OADC. Clinical isolates of *M. tuberculosis* were tested in 7H10/OADC or Bactec 12B at breakpoint concentrations of 5 or 7.5 μg ml$^{-1}$, respectively.

Chromosomal DNA was obtained from high-level resistant mutant *M. smegmatis* IMM30 after generation of protoplasms through overnight exposure to cycloserine 10 mg ml$^{-1}$, and ampicillin 1 mg ml$^{-1}$. Fragments (35–45 kb) obtained after partial digestion with Sau3A were ligated in Xba1-BamH1 pYUB415 arms (W. R. Jacobs Jr.), in vitro packaged (Gigapack III Gold, Stratagene, La Jolla Calif.) and transduced into *E. coli* colonies, selected on Luria Bertani with ampicillin 50 μg ml$^{-1}$, were pooled, their cosmids extracted, and DNA (1 μg) electroporated into electrocompetent *M. smegmatis* mc$^2$155 (Snapper, S. B., Melton, R. E., Mustafa, S., Kieser, T. & Jacobs Jr., W. R. Isolation and characterization of efficient transformation mutants of *Mycobacterium smegmatis, Mol Microbiol* 4, 1911–1919 (1990)). Transformants were selected on 7H11/OADC containing hygromycin 50 μg ml$^{-1}$ and 2.5, 20, or 100 μg ml$^{-1}$ EMB. Complementing cosmids were extracted from *M. smegmatis* protoplasms and transformed into *E. coli* StbI2 (gibco BRL, Basel, Switzerland). To identify the minimal-size DNA fragment conferring EMB resistance, a Sau3A partial digestion of one of the cosmids (pIMM50) was cloned into pMD31 (Levin, M. E. & Hatfull, G. F. *Mycobacterium smegmatis* RNA polymerase: DNA supercoiling, action of rifampicin and mechanism of rifampicin resistance. *Mol Microbiol* 8, 277–285 (1993)), electroporated into *M. smegmatis* mc$^2$155, and resistant transformants were identified on 7H11/OADC containing kanamycin 50 μg ml$^{-1}$ and 2.5, 20, or 100 μg ml$^{-1}$ EMB. Plasmid preparation was performed as described above and the smallest clone conferring the phenotype (pIMM99) was selected for sequencing. In addition, the 40 kb insert of pIMM50 was mobilized via PacI digestion to the integrative vector pYUB412 (W. R. Jacobs Jr.), and in vitro packaged. The resulting construct, pIMM52, was electroporated into *M. smegmatis* mc$^2$155 to assess its ability to confer an EMB-resistant phenotype as a single copy.

Sequencing was performed after shotgun fragmentation (sonication) of the emb region. Accuracy was assured by a sequence redundancy of 6. Identification of ORFs and prediction of coding sequences was done by using Mac Vector software (Kodak, New Haven Conn.) after construction of an *M. smegmatis* codon usage table. Sequence databases (GenBank, The Institute for Genomic Research, and MycDB World Wide Web sites) were searched for homologies. Topology prediction, and presence of palindromic and stemloop sequences were performed by using PredictProtein EMBL (Rost, B. & Sander, C. Combining evolutionary information and neural networks to predict protein secondary structure. *Proteins* 19, 55–72 (1994)), and the University of Wisconsin GCG package.

Mapping of the emb region on the *M. tuberculosis* chromosome was performed by probing an ordered cosmid library (Philipp, W. J. et al. An integrated map of the genome of the tubercle bacillus, Mycobacterium tuberculosis H37Rv, and comparison with *M. leprae, Proc Natl Acad Sci USA* 93, 3132–3137 (1996)) with a *M. tuberculosis* PCR fragment amplified using degenerated primers based on the *M. smegmatis embA* sequence. A positive clone (Y457) was mapped by restriction analysis and hybridization, and the appropriate fragments subcloned and sequenced using a shotgun approach. The 40 kb insert, was mobilized via PacI digestion to shuttle vector pYUB415, and in vitro packaged. The resulting construct, pIMM128, was electroporated into *M. smegmatis* mc$^2$155 to assess its ability to confer an EMB-resistant phenotype. The embA probe was also used in Southern blot analysis to determine the presence the emb gene cluster, or operon, in other mycobacteria (*M. vaccae, M. terrae, M. nonchromogenicum, M. kansasii, M. marinum, M. intracellulare, M. chitae, M. chelonae, M. aurum*), using *Staphylococcus aureus* and *E. coli* as negative control.

Total RNA was prepared from *M. smegmatis* mc$^2$155 by 5 sec sonication (Branson Sonifier 250 at constant output of 3) of pellets in Triazol (Gibco). After addition of chloroform, the organic phase was separated, and RNA was precipitated. For transcription start analysis, primers complementary to the coding regions of embC (5'-TCGCCATCAGCGTGCCGAGA) (SEQ. ID. NO:53), embA (5'-TCTCCTCCACCGGGAGCAGT) (SEQ. ID. NO:54), and embB (5'-GTTGCGCACGATCACGTCGA) (SEQ. ID. NO:55) were end-labelled by using [γ-32P]-ATP and T4 polynucleotide kinase. Total RNA (10 μg) was used in a primer extension reaction loaded onto a 6% polyacrylamide gel together with the corresponding sequencing reaction.

Mutation analysis of pIMM99, as well as of mutant strains of *M. smegmatis*, was performed by detailed sequence analysis of promoter, intergenetic, 600 bp of C-terminal sequence and the second cytoplasmic loop for all three emb genes. *M. tuberculosis* H37Rv and a collection of 70 clinical isolates were evaluated by targeted sequencing or by SSCP (single strand conformation polymorphism) of the described regions. Automated SSCP screening for embB mutations in *M. tuberculosis* was done as reported (Telenti, A., et al. *Antimicrob Agents Chemother* 37, 2054–2058 (1993)) by using fluorescent-labelled primers:

TE13f (5'-CAATTGCCCAGCTCCTCCTC) (SEQ ID NO:56) and

TE14f (5'-ACAGACTGGCGTCGCTGACA) (SEQ ID NO:57).

B. Results and Discussion

Resistance to EMB was used as a tool to identify genes participating in the biosynthesis of the mycobacterial cell wall, which led to the identification of the embCAB operon. The development of resistance to EMB was evaluated in the rapidly growing *M. smegmatis* (EMB MIC=0.5 μg/ml). Spontaneous EMB-resistant mutants of *M. smegmatis* were selected by stepwise exposure to increasing concentrations of the drug. Attainment of high level EMB resistance required three independent mutations at an approximate frequency of $10^{-7}$ for each step. Low (emb-1) and moderate level (emb-1 emb-2) resistance mutants exhibited EMB MICs of 20 and 100 μg/ml, respectively. High-level resistant mutants (emb-1 emb-2 emb-3) were not inhibited by extremely high concentrations of EMB (MIC>256 μg/ml). These results indicated that three consecutive genetic events, involving an accumulation of multiple mutations in one or more genes had taken place.

To identify the genes conferring EMB resistance, a genomic library from a high level EMB-resistant mutant of *M. smegmatis* was introduced into wild type *M. smegmatis* mc$^2$155 (Snapper, S. B. et al., Mol Microbiol 4, 1911–1919 (1990)). Four overlapping cosmids were identified which conferred a resistant phenotype. The minimum size fragment capable of conferring EMB resistance was 9 kb (pIMM99). Sequencing of pIMM99 plus 7 kb of upstream *M. smegmatis* sequence revealed three homologous open reading frames each approximately 3200 bp (embC, embA, embB), and four additional potential coding regions (see FIG. 1A). An *M. smegmatis* probe was used to identify the corresponding cosmid found from an ordered library (Philipp, W. J. et al., Proc Natl Acad Sci USA 93, 3132–3137 (1996). Sequencing of the *M. tuberculosis* homologue revealed the presence of complete copies of the emb genes. The *M. leprae* emb region was identified in one of the sequenced cosmids from the *M. leprae* genome project (Eiglmeier, K., et al., *Mol Microbiol* 7, 197–206 (1993)). Interestingly, while these mycobacteria presented a conserved organization over a 14 kb region, the emb operon of *M. avium* (Belanger, A. E. et al., *Proc Natl Acad Sci USA* 21, 11919–11924 (1996)) only contains the embaAB genes (see FIG. 1A). The emb genes were found by Southern blot analysis to be present in all mycobacteria tested (results not shown). However, nucleotide and protein searches revealed no significant homology of the emb to any non-mycobacterial submissions to public domain databases.

Figure 1C:
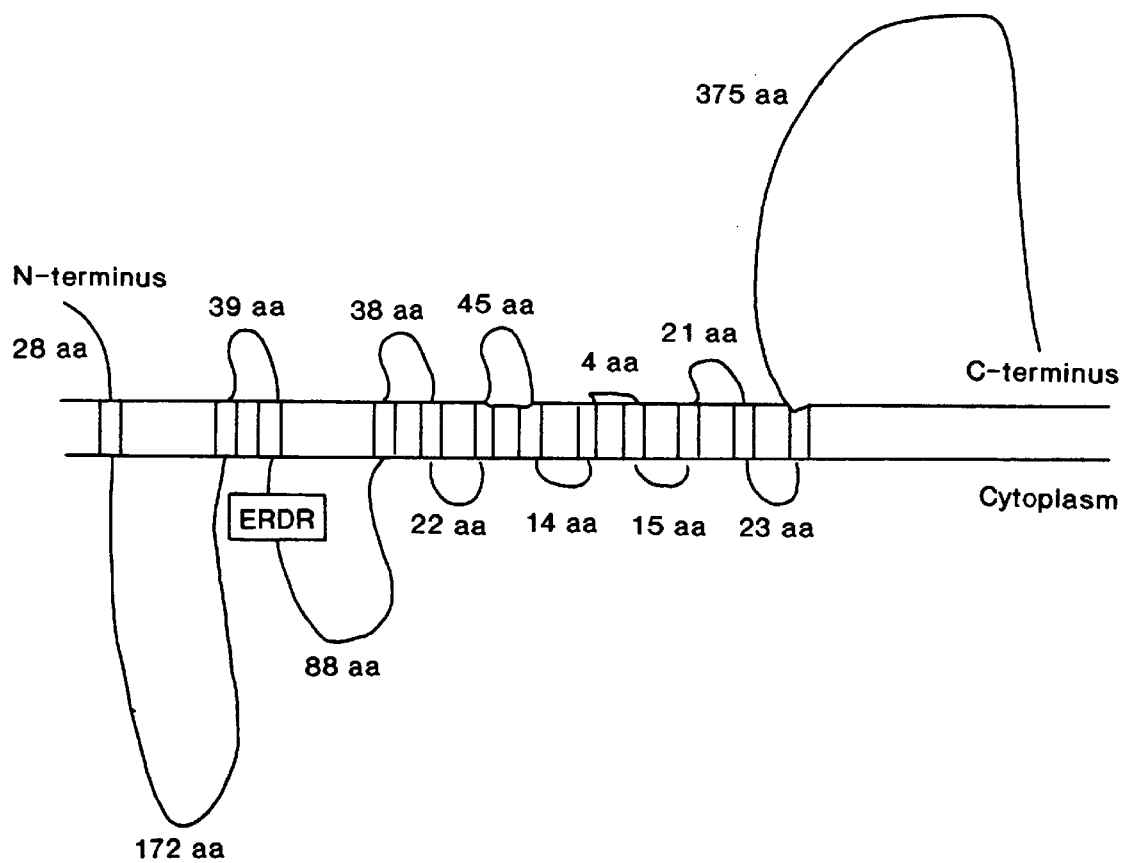

The emb genes represent examples of gene duplication, encoding proteins with amino acid similarities in the range of 61–68%. The emb region is organized as an operon, a concept supported by primer extension data indicating the polycistronic nature of the transcripts (FIG. 1B), and by the finding that there is almost no untranslated intercistronic region between the emb genes, indicating a tight translational coupling typical for proteins with coordinated expression. However, the presence at the junction between embA and embB of a potential secondary promoter in *M. smegmatis*, and of a stem-loop structure in *M. tuberculosis*, indicate that the last emb gene could be differentially regulated. Topology analysis suggests that the EmbCAB are integral membrane proteins with 12 transmembrane domains and a C-terminal globular region of ca. 400 amino acids of predicted periplasmic location (see FIG. 1C).

The feature of the emb products as membrane proteins with coordinated expression is consistent with a role in the synthesis of exopolysaccharides, where the several homologous genes would be responsible for the synthesis of the various arabinan linkage motifs. Indeed, compelling evidence for the role of the EMB proteins as arabinosyl transferases responsible for the polymerization of arabinose into the arabinogalactan has been recently presented by Belanger, et al. (Belanger, A. E. et al. *Proc Natl Acad Sci USA* 21, 11919–11924 (1996)).

Figure 2:
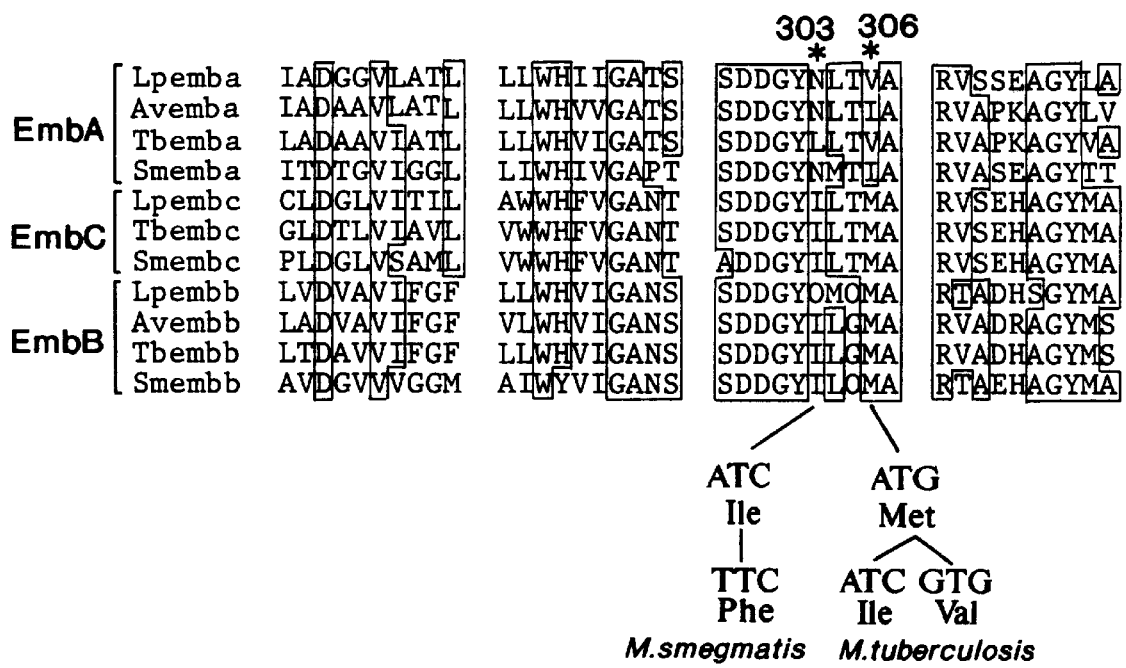
FIG. 2.
Figure 3:
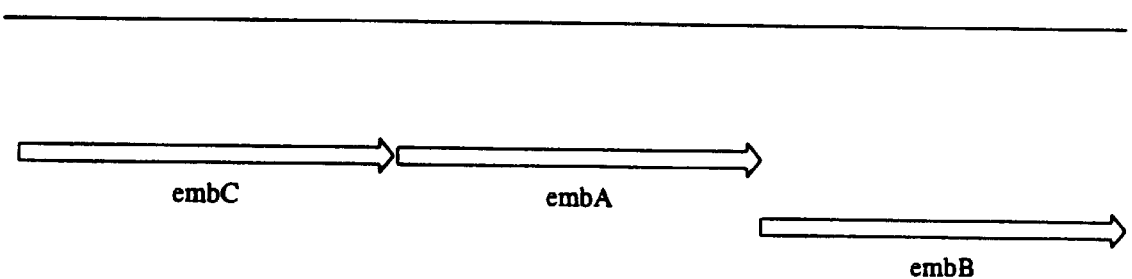
FIG. 3.
Figure 5:
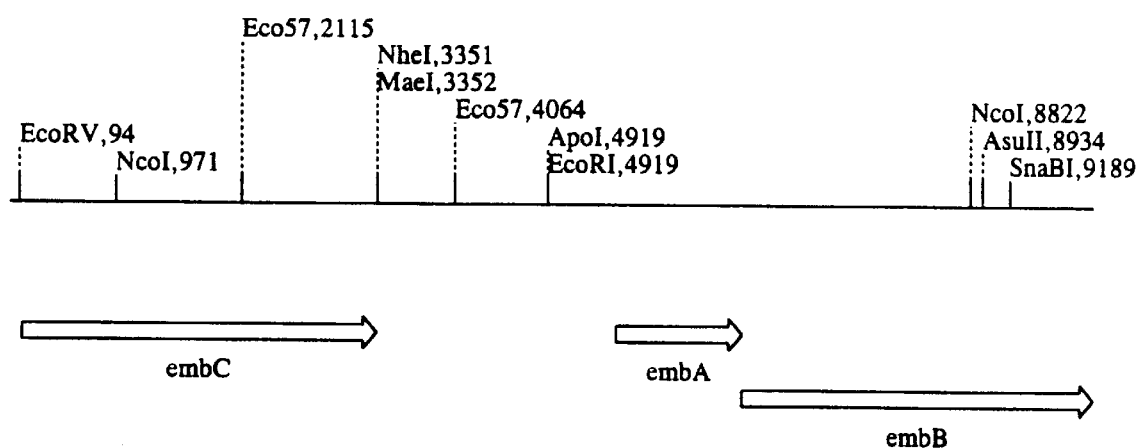
FIG. 5.
Figure 7:
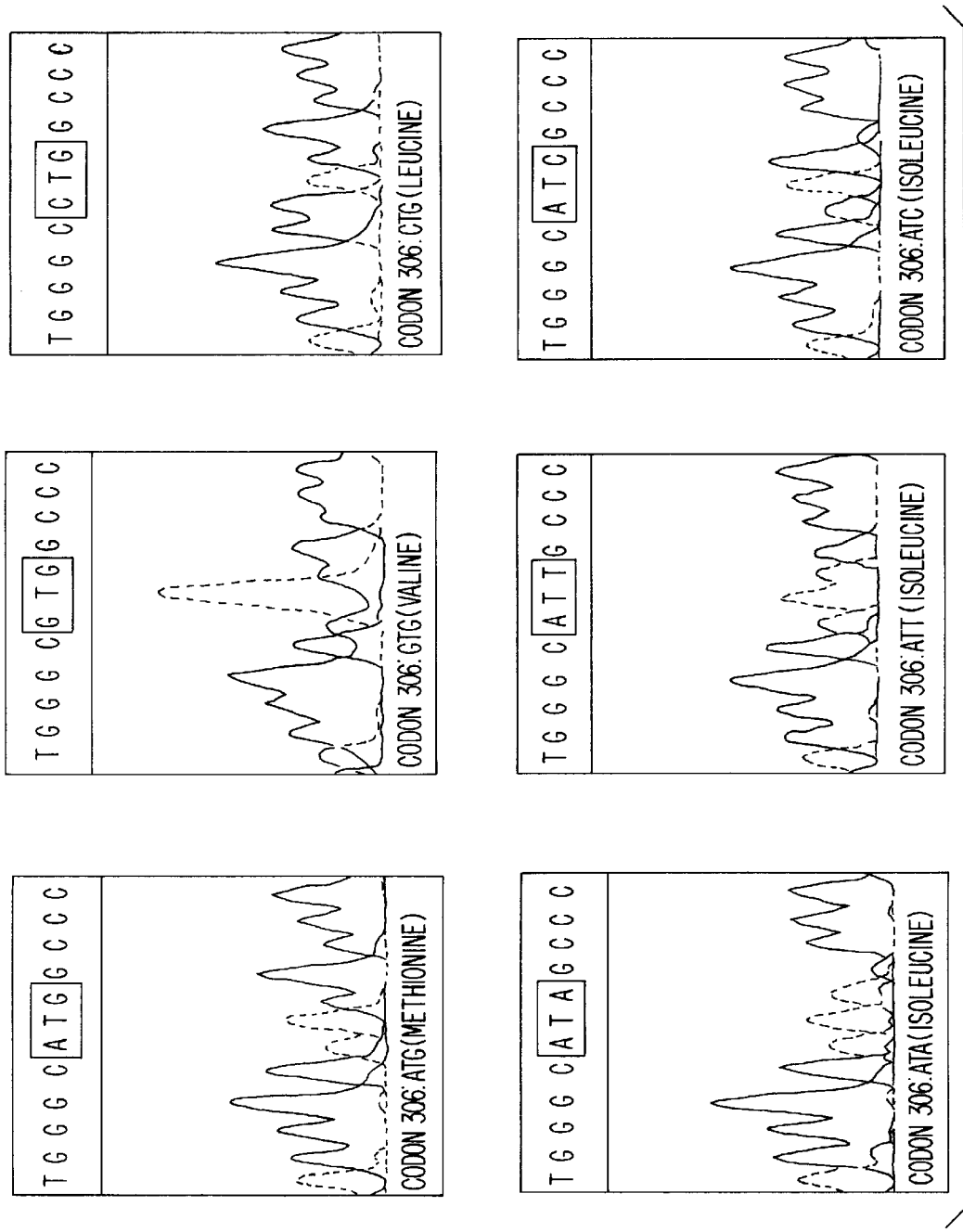
FIG. 7.

Identification of the embCAB genes allowed for the analysis of the molecular basis of resistance of mycobacteria to EMB. For this purpose, the sequence of resistant *M. smegmatis* mutants was compared with that of the parenteral strain, as well as the effect of mutant alleles on the phenotype of recombinant strains. Sequence analysis of pIMM99 and mutant strains of *M. smegmatis* identified an isoleucine to phenylalanine mutation in the embB of intermediate and high level resistant mutants which was not present in the parenteral susceptible strain. This substitution involves a residue (Ile303, *M. tuberculosis* coordinates) located in a loop of predicted cytoplasmic orientation (FIG. 1C) which is conserved among different mycobacterial Emb proteins (FIG. 2). In *M. tuberculosis*, mutations associated with resistance involved Met306, a conserved methionine codon. Mutation of *M. tuberculosis* Met306 to isoleucine or valine was identified in 12 of 278 (44.4%) EMB-resistant, unrelated, clinical isolates, but in none of 43 susceptible strains. Another interesting observation is that *M. leprae* exhibited a glutamine at the conserved Ile303 embB position, while maintaining a isoleucine residue at the homologous embC position. As EMB is not active against this organism (Dr. Pannikar, WHO, personal communication), this finding could represent the molecular basis for the intrinsic EMB resistance of *M. leprae*.

Evidence demonstrating that mutations in embB did confer EMB resistance was further supported with gene transfer experiments. Transformation of susceptible *M. smegmatis* with a multicopy plasmid carrying the mutant embCAB genes (embB2 allele) resulted in a more than 500-fold increase in EMB MIC (MIC>240 µg/ml). In contrast, transformation with the wild type allele from *M. tuberculosis* or *M. smegmatis* resulted in 2- to 20-fold increase in MIC values (MIC=1 and 10 µg/ml, respectively). Single-copy integration into the *M. smegmatis* chromosome of the 40 kb fragment from the high level resistant mutant resulted in a non-significant 2-fold increase in resistance to EMB (MIC= 1.0 µg/ml). This result suggests dominance of the wild type to the embB2 allele in a merodiploid state, and indicates that the additional mutations required to achieve high level resistance, likely of regulatory nature, are not present within the region.

These data confirm the association of a specific mutation to a resistance phenotype and indicate that the emb proteins are a probable target of the drug. Though the actual mechanism of action of the drug remains to be determined, it can be speculated that the mutations modify a glycosyltransferase active site to which EMB, proposed to act as a arabinose analogue (Maddry, J. A., et al. *Res Microbiol* 147, 106–112 (1996)), binds. The complexity of the biological phenomenon of EMB resistance is however underscored by (i) the observation that multiple steps are necessary to achieve high level resistance, and (ii) the yet unmapped location of EMB-resistance mutations in the first- and last-step laboratory resistance mutants of *M. smegmatis*, and in a proportion of *M. tuberculosis* isolates. Thus, additional genes should be operative in the development of resistance, a notion consistent with the observed pleiotropic action of the drug (Deng, L., et al., *Antimicrob Agents Chemother* 39, 694–701 (1995)).

The data in the present manuscript add to the understanding of the mechanism of action and resistance to antituberculous drugs (Musser, J. M., *Clin Microbiol Rev* 8, 496–514 (1995)). To date, 11 mycobacterial genes have been identified associated with drug resistance: katG, mabA/inhA, and ahpC (isoniazid) (Zhang, Y., et al. *Nature* 358, 501–593 (1992); Banerjee, A. et al. *Science* 263, 227–230 (1994); Deretic, V., et al. *Mol Microbiol* 17, 889–900 (1995); Wilson, T. M. & Collins, D. M., *Mol Microbiol* 19, 1025–1034 (1996); Telenti, A., et al. *J. Clin Microbiol* in press, (1996)), rpoB (rifampin) (Telenti, A. et al. *Lancet* 341, 647–650 (1993)), rrs and rpsL streptomycin) (Finken, M., et al. *Mol Microbiol* 9, 1239–1246 (1993)), (Honore, N. & Cole, S. T. *Antimicrob Agents Chemother* 38, 238–242 (1994)), gyrA, gyrB and lfrA (fluoroquinolones) ((Takiff, H. E. et al. *Antimicrob Agents Chemother* 38, 773–780 (1994); Kocagoz, T., et al. *Antimicrob Agents Chemother* 40, 1768–1774 (1996); Takiff, H. E., et al. *Proc Natl Acad Sci USA* 93, 362–366 (1996)), and pncA (pyrazinamide) (Scorpio, A. & Zhang, Y. *Nature Med* 2, 662–667 (1996)). This information allowed the development of novel strategies for detection of drug resistance, reducing the length of testing from weeks to days (Telenti, A. & Persing, D. H. *Res. Microbiol* 147, 73–79 (1996)). Alternative means of testing would prove particularly useful for EMB, as susceptibility testing to this drug remains suboptimally standardized (Lazlo, A., et al. Quality assurance programme for Drug susceptibility testing of *Mycobacterium tuberculosis* in the WHO/IUTLD supranational laboratory network: first round of proficiency testing. *Journal of the International Union against Tuberculosis and Lung Disease* in press, (1997)), due to the poor stability of the agent in growth media (Gangadharam, P. R. & Gonzalez, E. R. *Am Rev Resp Dis* 102, 653–655 (1970)), and to discrepancies encountered when performing the analysis in solid versus liquid media (Heifets, L. B., et al. *Antimicrob Agents Chemother* 30, 927–932 (1986)). In the current study, automated sequencing and automated SSCP was used for detection of embB mutations. Both techniques unambiguously identified the prevalent Met306 mutation in clinical isolates of EMB-resistant *M. tuberculosis*.

In conclusion, the selective and broad-spectrum activity of EMB against mycobacteria correlates with the identification of a unique and conserved operon structure which appears to encode its drug target. Identification of mutations opens the possibility to implement genotype-based tests for the rapid detection of EMB resistance in *M. tuberculosis*. Mapping of additional mutations associated with resistance will guide the efforts to define the mechanism of action of EMB and to identify discrete active domains in the Emb proteins, the putative mycobacterial arabinosyl transferases.

The Role of embB Mutations

I. Materials and Methods

A. Bacterial Strains

The study of the role of embB mutations was based on a sample of 118 *M. tuberculosis* isolates recovered in diverse localities in the United States, Europe, Yemen, Philippines, Japan, and India. The sample includes 85 EMB-resistant and 33 EMB-susceptible organisms. The bacteria were recovered from diseased patients with a variety of distinct clinical manifestations, and included both pulmonary and extrapulmonary sources.

B. IS6110 Genotyping and Genetic Group Assignment

Strain growth and DNA isolation were performed in laboratories equipped with biosafety level 3 facilities. Isolation of chromosomal DNA and IS61100 typing were performed by previously described methods (van Embden, et al., *J. Clin. Microbiol.* 31:406–409 (1993)). Recent data have demonstrated that all *M. tuberculosis* isolates can be assigned to one of three genetic groups based on polymorphisms present at codon 463 of the gene (katG) encoding catalase-peroxide, and codon 95 of the gene (gyrA) encoding the A subunit of DNA gyrase (Srinand, et al., Molecular Population Genetics of katG codon 463 and gyrA codon 95 polymorphisms in the *Mycobacterium tuberculosis* complex (MTC), abstr. U119, p. 122. In *Abstracts of the General Meeting of the American Society for Microbiology*, Washington, D.C.). The group designations used are as follows: group 1, katG463 CTG (Leu) plus gyrA95 ACC (Thr); group 2, katG463 CGG (Arg) plus gyrA95 ACC (Thr); and group 3, katG463 CGG (Arg) plus gyrA95 AGC (Thr).

C. Ethambutol Susceptibility Testing

Routine EMB susceptibility testing was conducted by either the BACTEC radiorespiratory method (7.5 μg/ml) or agar diffusion with Middlebrook 7H10 medium (5 μg/ml). To determine EMB MICs, susceptibility testing was performed by agar diffusion as described previously (National Committee for Clinical Laboratory Studies, 1990. Antimicrobial Susceptibility Testing. Proposed Standard M24-P. National Committee for Clinical Laboratory Standards, Villanova, Pa.). EMB (Sigma Chemical Co., St. Louis, Mo.) was incorporated into 7H10 agar (Difco, Detroit, Mich.) at the following concentrations: 0, 0.5, 1, 2.5, 5, 10, 20, and 40 μg/ml. Frozen cultures of *M. tuberculosis* stored at −70° C. in 7H9 broth in 15% glycerol were recovered on Lowenstain-Jensen slants. Each isolate was then subcultured on 7H10 agar, suspended in 7H9/ADC broth (Difco) in the presence of glass beads to a concentration of $10^7$ CFU/ml, diluted 1:100, and plated in duplicate (0.1 ml per quadrant). The plates were incubated at 35° C. in the presence of 5% $CO_2$. Each plate was checked weekly, and the results were recorded between weeks 3 and 4.

D. Automated DNA Sequencing of the embCAB Locus

The 7.5 kb region of embCAB was sequenced in various stages using a total of 30 primers. A GeneAmp System 9600 thermocycler (Perkin Elmer Corp., Foster City, Calif.) was used for all target amplifications, with the following parameters: annealing temperature at 65° C. for 39 sec, extension at 72° C. for 82 sec, and a denaturation step at 94° C. for 54 sec for a total of 30 cycles. Each reaction was preceded by an initial denaturation step at 94° C. for 60 sec, and terminated with a final extension step at 72° C. for 5 minutes. DNA sequencing reactions were performed with the Taq Dye Deoxy terminator cycle sequencing kit using Amplitaq DNA polymerase FS (Applied Biosystems, Inc., Foster City, Calif.). The forward, reverse, and internal primers were used for sequencing. Sequence data generated with an ABI 377 automated instrument were assembled and edited electronically with EDITSEQ. ALIGN, and MEGALIGN programs (DNASTAR, Madison, Wis.), and compared with a published sequence (Telenti, et al., *Nature Med.* (in press, 1997)) and a sequence generated from *M. tuberculosis* strain H37Rv for the entire embCAB locus.

Nineteen *M. tuberculosis* (16 EMB-resistant and 3 EMB-susceptible) isolates were analyzed for the entire 7.5 kb region except a 75-bp segment located at the beginning of embB. This region is characterized by the presence of a stem loop structure (Telenti, et al., *Nature Med.* (in press, 1997)) and sequence data could not be reproducibly obtained for all isolates. The 5' region (1,892 bp) of embB was analyzed in an additional 69 EMB-resistant and 30-susceptible *M. tuberculosis* isolates from diverse geographic localities, and representing 70 IS6110 fingerprints.

II. Results

A. Alteration in embCAB Locus among 19 Strains Sequenced in Entirety

Analysis of 16 EMB-resistant and 3-susceptible isolates identified a total of four polymorphic nucleotide sites, each located in different regions of the three-gene locus. For example, a polymorphism (G>C) was identified at nucleotide 195 of embC in two EMB resistant and one EMB susceptible isolate. This change would produce a Val→Leu substitution in embC. These same three isolates also had a G→A synonymous substitution at nucleotide 2898 of embA. One resistant isolate also had a missense mutation in codon 5 of embA (GGT→AGT) resulting in G→S alteration. Interestingly, eight EMB-resistant strains had three distinct missense mutations in codon 306 of embB (ATG, Met) resulting in substitution with Ile (ATA and ATC) or Val (GTG). Hence, the sequence data for the entire 7.5 kb embCAB locus suggested that mutations associated with resistance were overrepresented in the 5' portion of embB.

B. Variation in the 5' Segment of embB among 69 EMB-resistant and 30 EMB-susceptible Isolates.

Because the results obtained from sequencing the entire 7.5 kb embCAB region suggested that mutations in codon 306 of embB were important in EMB resistance, a 1,892 bp embB region was sequenced in 69 EMB-resistant and 30 EMB-susceptible organisms. This sample included 51 EMB-resistant and 25 EMB-susceptible strains judged to be epidemiologically unassociated because they had distinct IS6110 patterns. All 30 EMB-susceptible organisms had the same wild type sequence. In striking contrast, the 69 EMB-resistant strains had eight distinct missense mutations in this 1,892-bp region. These mutations occurred in individual codons, including 285 (TTC→TTA, Phe→Leu), 330 (TTC→GTC, Phe→Val), and 630 (ACC→ATC, Thr→Ile). Five distinct missense mutations were identified in codon 306 (ATG): GTG (Val), CTG (Leu), ATA (Ile), ATC (Ile), and ATT (Ile). (See FIG. 7). When only epidemiologically unassociated organisms are considered, 69% of EMB-resistant bacteria had an amino acid change in the region of embb studied, and most replacements (89%) occurred at position 306.

The analysis included two pairs of EMB-resistant and susceptible isolates with two different IS6110 fingerprints. The resistant isolates had either Met306Ile or Met306Val alterations, whereas the paired susceptible isolates had the identical wild type embB sequence.

C. Correlation of embB Mutation with EMB MICs

The relationship of embB mutations with level of resistance to EMB were next studied. MICs were determined for resistant organisms by plating on 7H10 agar containing EMB in a range on concentrations between 0 and 40 μg/ml. Because of this relatively large number of strains characterized for the embB sequence, not all organisms were analyzed for EMB MIC. Rather, a representative subset of strains was studied that together contain a broad array of embB mutation and IS6100 subtypes. A summary of the MICs for the genetically characterized *M. tuberculosis* isolates is presented in Table 1. All isolates with the embB position 306 substitutions had EMB MICs of 20 or 40 μg/ml. Interestingly, regardless of genetic background as indexed by IS6110 typing, and katG463/gyrA95 group, bacteria with a Met306Ile replacement had an MIC of 20 μg/ml, whereas organisms with a Met306Leu or Met306Val change had an MIC of 40 μg/ml. In addition, one organism with a Phe330Val change had an MIC of 40, and two epidemiologically related strains with a Thr630Ile change had an EMB MIC exceeding 40 μg/ml.

III. Discussion

The recent demonstration that mutations in the *M. tuberculosis* embCAB locus are associated with EMB resistance prompted a more thorough examination of sequence variation at this locus in genetically distinct susceptible and resistant organisms. In particular, the aim of the study was to determine if polymorphisms were uniquely present in EMB-resistant versus -susceptible *M. tuberculosis* isolates. The results documented two findings about sequence variation in this 7.5 kb region. First, there is restricted variation in embCAB in natural populations of *M. tuberculosis* recovered from diverse geographic sources. This result confirms data generated in the course of study of several antimicrobial agent target genes including katg, rpoB, strA, rrs, and others. The embCAB data are also consistent with the hypothesis that *M. tuberculosis* is evolutionarily new, perhaps having arisen as recently as 15,000–20,000 years ago. Second, the results document the unique and common association of embB amino acid residue 306 substitutions with EMB resistance. The only reasonable hypothesis to explain the occurrence of five distinct mutant codons resulting in three different amino acid replacements at embB position 306 of EMB resistant organisms is that they have arisen by positive Darwinian selection in the course of drug therapy. Hence, it is likely that these amino acid substitutions mediate EMB resistance, rather than are simply surrogate markers for drug resistant organisms.

The region of embB containing residue Met 306 is highly conserved in *M. tuberculosis, M. avium, M. leprae*, and *M. smegmatis*. Moreover, based on amino acid sequence alignments, a Met residue would be present at position 306 in these four species. Biochemical studies and sequence alignments have suggested that embB is a glycosyltransferase. Telenti, et al. (*Nature Med.* (in press, 1997)) hypothesized that embB is an integral membrane protein with 12 transmembrane domains and a C-terminal globular region of about 400 amino acids with predicted location in the periplasm. The data herein is fully consistent with the idea that these mutations detrimentally affect a glycosyltransferase biding site to where EMB, proposed (Maddry, et al., *Res. Microbiol.* 147:106–112 (1996)) to be an arabinose analog, binds. The identification of a range of embB variants provides an important resource for biochemical and structural studies designed to more fully investigate the molecular mechanisms of EMB action.

The data generated from the EMB susceptibility testing suggest the existence of a non-random association between certain amino acid substitutions at embB position 306 and level of resistance to EMB. Analogous data have been presented for amino acid substitutions in the fluoroquinolone resistance-determining region of the A subunit of DNA gyrase (Xu, et al., *J. Infect. Dis.*, 174:1127–1130 (1996)), changes in the beta subunit of RNA polymerase that confer resistance to rifampin and related drugs, and mutations conferring streptomycin resistance. The association of particular amino acid substitutions with EMB MIC level implies that position 306 contains important structure-function information.

All publications mentioned hereinabove are hereby incorporated by reference in their entirety.

While the foregoing invention has been described in detail for purpose of clarity and understanding, it will be appreciated by one skilled in the art from a reading of the disclosure that various changes in form and detail can be made without departing from the true scope of the invention in the appended claims.

What is claimed is:

1. A purified and isolated nucleic acid sequence of the embCAB operon from *M. tuberculosis* having the nucleotide sequence contained in FIG. 4 (SEQ ID NO:45).

2. The nucleic acid of claim 1 having at least one mutation that results in ethambutol resistance.

3. The nucleic acid of claim 2 wherein the mutation is selected from the group consisting of deletion, insertion, point, substitution, nonsense, missense, polymorphism, and rearrangement mutations.

4. The nucleic acid of claim 3 wherein the mutation is a missense mutation.

5. The nucleic acid of claim 4 wherein the missense mutation is located within SEQ ID NO:45, within the embB nucleic acid sequence of the embCAB operon.

6. The nucleic acid of claim 4 wherein the missense mutation is located within SEQ ID NO:45, in the embA nucleic acid sequence of the embCAB operon.

7. The nucleic acid of claim 3 wherein the mutation is a substitution mutation.

8. The nucleic acid of claim 7 wherein the substitution mutation is located within SEQ ID NO:45, in the embA nucleic acid sequence of the embCAB operon.

9. The nucleic acid of claim 3 wherein the mutation is a polymorphism.

10. The nucleic acid of claim 9 wherein the polymorphism mutation is located within SEQ ID NO:45, in the embC nucleic acid sequence of the embCAB operon.

* * * * *

```
                        SEQUENCE LISTING (1) GENERAL INFORMATION:

(iii) NUMBER OF SEQUENCES:  57

(2) INFORMATION FOR SEQ ID NO:1:

(i) SEQUENCE CHARACTERISTICS:
           (A) LENGTH:  10 amino acids
           (B) TYPE:  amino acid
           (C) STRANDEDNESS:  single
           (D) TOPOLOGY:  linear (ii) MOLECULE TYPE:
           (A) DESCRIPTION:  peptide (iii) HYPOTHETICAL:  NO (v) FRAGMENT TYPE: internal fragment (xi) SEQUENCE DESCRIPTION:  SEQ ID NO: 1:

Ile Ala Asp Gly Gly Val Leu Ala Thr Leu
1               5                   10

(2) INFORMATION FOR SEQ ID NO:2:

(i) SEQUENCE CHARACTERISTICS:
           (A) LENGTH:  10 amino acids
           (B) TYPE:  amino acid
           (C) STRANDEDNESS:  single
           (D) TOPOLOGY:  linear (ii) MOLECULE TYPE:
           (A) DESCRIPTION:  peptide (iii) HYPOTHETICAL:  NO (v) FRAGMENT TYPE: internal fragment (xi) SEQUENCE DESCRIPTION:  SEQ ID NO: 2:

Leu Leu Trp His Ile Ile Gly Ala Thr Ser
```

```
1               5                  10

(2) INFORMATION FOR SEQ ID NO:3:

(i) SEQUENCE CHARACTERISTICS:
         (A) LENGTH:  10 amino acids
         (B) TYPE:  amino acid
         (C) STRANDEDNESS:  single
         (D) TOPOLOGY:  linear (ii) MOLECULE TYPE:
         (A) DESCRIPTION:  peptide (iii) HYPOTHETICAL:  NO (v) FRAGMENT TYPE: internal fragment (xi) SEQUENCE DESCRIPTION:  SEQ ID NO: 3:

Ser Asp Asp Gly Tyr Asn Leu Thr Val Ala
1               5                  10

(2) INFORMATION FOR SEQ ID NO:4:

(i) SEQUENCE CHARACTERISTICS:
         (A) LENGTH:  10 amino acids
         (B) TYPE:  amino acid
         (C) STRANDEDNESS:  single
         (D) TOPOLOGY:  linear (ii) MOLECULE TYPE:
         (A) DESCRIPTION:  peptide (iii) HYPOTHETICAL:  NO (v) FRAGMENT TYPE: internal fragment (xi) SEQUENCE DESCRIPTION:  SEQ ID NO: 4:

Arg Val Ser Ser Glu Ala Gly Tyr Leu Ala
1               5                  10

(2) INFORMATION FOR SEQ ID NO:5:

(i) SEQUENCE CHARACTERISTICS:
         (A) LENGTH:  10 amino acids
         (B) TYPE:  amino acid
         (C) STRANDEDNESS:  single
         (D) TOPOLOGY:  linear (ii) MOLECULE TYPE:
         (A) DESCRIPTION:  peptide (iii) HYPOTHETICAL:  NO (v) FRAGMENT TYPE: internal fragment (xi) SEQUENCE DESCRIPTION:  SEQ ID NO: 5:

Ile Ala Asp Ala Ala Val Leu Ala Thr Leu
1               5                  10

(2) INFORMATION FOR SEQ ID NO:6:

(i) SEQUENCE CHARACTERISTICS:
         (A) LENGTH:  10 amino acids
         (B) TYPE:  amino acid
         (C) STRANDEDNESS:  single
         (D) TOPOLOGY:  linear (ii) MOLECULE TYPE:
         (A) DESCRIPTION:  peptide (iii) HYPOTHETICAL:  NO (v) FRAGMENT TYPE: internal fragment
```

(xi) SEQUENCE DESCRIPTION: SEQ ID NO: 6:

Leu Leu Trp His Val Val Gly Ala Thr Ser
1               5                   10

(2) INFORMATION FOR SEQ ID NO:7:

(i) SEQUENCE CHARACTERISTICS:
        (A) LENGTH:  10 amino acids
        (B) TYPE:  amino acid
        (C) STRANDEDNESS:  single
        (D) TOPOLOGY:  linear (ii) MOLECULE TYPE:
        (A) DESCRIPTION:  peptide (iii) HYPOTHETICAL:  NO (v) FRAGMENT TYPE: internal fragment (xi) SEQUENCE DESCRIPTION: SEQ ID NO: 7:

Ser Asp Asp Gly Tyr Asn Leu Thr Ile Ala
1               5                   10

(2) INFORMATION FOR SEQ ID NO:8:

(i) SEQUENCE CHARACTERISTICS:
        (A) LENGTH:  10 amino acids
        (B) TYPE:  amino acid
        (C) STRANDEDNESS:  single
        (D) TOPOLOGY:  linear (ii) MOLECULE TYPE:
        (A) DESCRIPTION:  peptide (iii) HYPOTHETICAL:  NO (v) FRAGMENT TYPE: internal fragment (xi) SEQUENCE DESCRIPTION: SEQ ID NO: 8:

Arg Val Ala Pro Lys Ala Gly Tyr Leu Val
1               5                   10

(2) INFORMATION FOR SEQ ID NO:9:

(i) SEQUENCE CHARACTERISTICS:
        (A) LENGTH:  10 amino acids
        (B) TYPE:  amino acid
        (C) STRANDEDNESS:  single
        (D) TOPOLOGY:  linear (ii) MOLECULE TYPE:
        (A) DESCRIPTION:  peptide (iii) HYPOTHETICAL:  NO (v) FRAGMENT TYPE: internal fragment (xi) SEQUENCE DESCRIPTION: SEQ ID NO: 9:

Leu Ala Asp Ala Ala Val Ile Ala Thr Leu
1               5                   10

(2) INFORMATION FOR SEQ ID NO:10:

(i) SEQUENCE CHARACTERISTICS:
        (A) LENGTH:  10 amino acids
        (B) TYPE:  amino acid
        (C) STRANDEDNESS:  single
        (D) TOPOLOGY:  linear (ii) MOLECULE TYPE:
        (A) DESCRIPTION:  peptide (iii) HYPOTHETICAL:  NO (v) FRAGMENT TYPE: internal fragment (xi) SEQUENCE DESCRIPTION:  SEQ ID NO: 10:

Leu Leu Trp His Val Ile Gly Ala Thr Ser
1               5                  10

(2) INFORMATION FOR SEQ ID NO:11:

(i) SEQUENCE CHARACTERISTICS:
          (A) LENGTH:  10 amino acids
          (B) TYPE:  amino acid
          (C) STRANDEDNESS:  single
          (D) TOPOLOGY:  linear (ii) MOLECULE TYPE:
          (A) DESCRIPTION:  peptide (iii) HYPOTHETICAL:  NO (v) FRAGMENT TYPE: internal fragment (xi) SEQUENCE DESCRIPTION:  SEQ ID NO: 11:

Ser Asp Asp Gly Tyr Leu Leu Thr Val Ala
1               5                  10

(2) INFORMATION FOR SEQ ID NO:12:

(i) SEQUENCE CHARACTERISTICS:
          (A) LENGTH:  10 amino acids
          (B) TYPE:  amino acid
          (C) STRANDEDNESS:  single
          (D) TOPOLOGY:  linear (ii) MOLECULE TYPE:
          (A) DESCRIPTION:  peptide (iii) HYPOTHETICAL:  NO (v) FRAGMENT TYPE: internal fragment (xi) SEQUENCE DESCRIPTION:  SEQ ID NO: 12:

Arg Val Ala Pro Lys Ala Gly Tyr Val Ala
1               5                  10

(2) INFORMATION FOR SEQ ID NO:13:

(i) SEQUENCE CHARACTERISTICS:
          (A) LENGTH:  10 amino acids
          (B) TYPE:  amino acid
          (C) STRANDEDNESS:  single
          (D) TOPOLOGY:  linear (ii) MOLECULE TYPE:
          (A) DESCRIPTION:  peptide (iii) HYPOTHETICAL:  NO (v) FRAGMENT TYPE: internal fragment (xi) SEQUENCE DESCRIPTION:  SEQ ID NO: 13:

Ile Thr Asp Thr Gly Val Ile Gly Gly Leu
1               5                  10

(2) INFORMATION FOR SEQ ID NO:14:

(i) SEQUENCE CHARACTERISTICS:
          (A) LENGTH:  10 amino acids
          (B) TYPE:  amino acid
          (C) STRANDEDNESS:  single

```
            (D) TOPOLOGY:  linear (ii) MOLECULE TYPE:
            (A) DESCRIPTION:  peptide (iii) HYPOTHETICAL:  NO (v) FRAGMENT TYPE: internal fragment (xi) SEQUENCE DESCRIPTION:  SEQ ID NO: 14:

Leu Ile Trp His Ile Val Gly Ala Pro Thr
1               5                   10

(2) INFORMATION FOR SEQ ID NO:15:

(i) SEQUENCE CHARACTERISTICS:
            (A) LENGTH:  10 amino acids
            (B) TYPE:  amino acid
            (C) STRANDEDNESS:  single
            (D) TOPOLOGY:  linear (ii) MOLECULE TYPE:
            (A) DESCRIPTION:  peptide (iii) HYPOTHETICAL:  NO (v) FRAGMENT TYPE: internal fragment (xi) SEQUENCE DESCRIPTION:  SEQ ID NO: 15:

Ser Asp Asp Gly Tyr Asn Met Thr Ile Ala
1               5                   10

(2) INFORMATION FOR SEQ ID NO:16:

(i) SEQUENCE CHARACTERISTICS:
            (A) LENGTH:  10 amino acids
            (B) TYPE:  amino acid
            (C) STRANDEDNESS:  single
            (D) TOPOLOGY:  linear (ii) MOLECULE TYPE:
            (A) DESCRIPTION:  peptide (iii) HYPOTHETICAL:  NO (v) FRAGMENT TYPE: internal fragment (xi) SEQUENCE DESCRIPTION:  SEQ ID NO: 16:

Arg Val Ala Ser Glu Ala Gly Tyr Thr Thr
1               5                   10

(2) INFORMATION FOR SEQ ID NO:17:

(i) SEQUENCE CHARACTERISTICS:
            (A) LENGTH:  10 amino acids
            (B) TYPE:  amino acid
            (C) STRANDEDNESS:  single
            (D) TOPOLOGY:  linear (ii) MOLECULE TYPE:
            (A) DESCRIPTION:  peptide (iii) HYPOTHETICAL:  NO (v) FRAGMENT TYPE: internal fragment (xi) SEQUENCE DESCRIPTION:  SEQ ID NO: 17:

Cys Leu Asp Gly Leu Val Ile Thr Ile Leu
1               5                   10

(2) INFORMATION FOR SEQ ID NO:18:
```

```
    (i) SEQUENCE CHARACTERISTICS:
         (A) LENGTH:  10 amino acids
         (B) TYPE:  amino acid
         (C) STRANDEDNESS:  single
         (D) TOPOLOGY:  linear (ii) MOLECULE TYPE:
         (A) DESCRIPTION:  peptide (iii) HYPOTHETICAL:  NO (v) FRAGMENT TYPE: internal fragment (xi) SEQUENCE DESCRIPTION:  SEQ ID NO: 18:

Ala Trp Trp His Phe Val Gly Ala Asn Thr
1               5                  10

(2) INFORMATION FOR SEQ ID NO:19:

(i) SEQUENCE CHARACTERISTICS:
         (A) LENGTH:  10 amino acids
         (B) TYPE:  amino acid
         (C) STRANDEDNESS:  single
         (D) TOPOLOGY:  linear (ii) MOLECULE TYPE:
         (A) DESCRIPTION:  peptide (iii) HYPOTHETICAL:  NO (v) FRAGMENT TYPE: internal fragment (xi) SEQUENCE DESCRIPTION:  SEQ ID NO: 19:

Ser Asp Asp Gly Tyr Ile Leu Thr Met Ala
1               5                  10

(2) INFORMATION FOR SEQ ID NO:20:

(i) SEQUENCE CHARACTERISTICS:
         (A) LENGTH:  10 amino acids
         (B) TYPE:  amino acid
         (C) STRANDEDNESS:  single
         (D) TOPOLOGY:  linear (ii) MOLECULE TYPE:
         (A) DESCRIPTION:  peptide (iii) HYPOTHETICAL:  NO (v) FRAGMENT TYPE: internal fragment (xi) SEQUENCE DESCRIPTION:  SEQ ID NO: 20:

Arg Val Ser Glu His Ala Gly Tyr Met Ala
1               5                  10

(2) INFORMATION FOR SEQ ID NO:21:

(i) SEQUENCE CHARACTERISTICS:
         (A) LENGTH:  10 amino acids
         (B) TYPE:  amino acid
         (C) STRANDEDNESS:  single
         (D) TOPOLOGY:  linear (ii) MOLECULE TYPE:
         (A) DESCRIPTION:  peptide (iii) HYPOTHETICAL:  NO (v) FRAGMENT TYPE: internal fragment (xi) SEQUENCE DESCRIPTION:  SEQ ID NO: 21:

Gly Leu Asp Thr Leu Val Ile Ala Val Leu
1               5                  10
```

```
(2) INFORMATION FOR SEQ ID NO:22:

(i) SEQUENCE CHARACTERISTICS:
        (A) LENGTH:  10 amino acids
        (B) TYPE:  amino acid
        (C) STRANDEDNESS:  single
        (D) TOPOLOGY:  linear (ii) MOLECULE TYPE:
        (A) DESCRIPTION:  peptide (iii) HYPOTHETICAL:  NO (v) FRAGMENT TYPE: internal fragment (xi) SEQUENCE DESCRIPTION:  SEQ ID NO: 22:

Val Trp Trp His Phe Val Gly Ala Asn Thr
1               5                   10

(2) INFORMATION FOR SEQ ID NO:23:

(i) SEQUENCE CHARACTERISTICS:
        (A) LENGTH:  10 amino acids
        (B) TYPE:  amino acid
        (C) STRANDEDNESS:  single
        (D) TOPOLOGY:  linear (ii) MOLECULE TYPE:
        (A) DESCRIPTION:  peptide (iii) HYPOTHETICAL:  NO (v) FRAGMENT TYPE: internal fragment (xi) SEQUENCE DESCRIPTION:  SEQ ID NO: 23:

Ser Asp Asp Gly Tyr Ile Leu Thr Met Ala
1               5                   10

(2) INFORMATION FOR SEQ ID NO:24:

(i) SEQUENCE CHARACTERISTICS:
        (A) LENGTH:  10 amino acids
        (B) TYPE:  amino acid
        (C) STRANDEDNESS:  single
        (D) TOPOLOGY:  linear (ii) MOLECULE TYPE:
        (A) DESCRIPTION:  peptide (iii) HYPOTHETICAL:  NO (v) FRAGMENT TYPE: internal fragment (xi) SEQUENCE DESCRIPTION:  SEQ ID NO: 24:

Arg Val Ser Glu His Ala Gly Tyr Met Ala
1               5                   10

(2) INFORMATION FOR SEQ ID NO:25:

(i) SEQUENCE CHARACTERISTICS:
        (A) LENGTH:  10 amino acids
        (B) TYPE:  amino acid
        (C) STRANDEDNESS:  single
        (D) TOPOLOGY:  linear (ii) MOLECULE TYPE:
        (A) DESCRIPTION:  peptide (iii) HYPOTHETICAL:  NO (v) FRAGMENT TYPE: internal fragment
```

```
        (xi) SEQUENCE DESCRIPTION: SEQ ID NO: 25:

Pro Leu Asp Gly Leu Val Ser Ala Met Leu
1               5                   10

(2) INFORMATION FOR SEQ ID NO:26:

(i) SEQUENCE CHARACTERISTICS:
         (A) LENGTH: 10 amino acids
         (B) TYPE: amino acid
         (C) STRANDEDNESS: single
         (D) TOPOLOGY: linear (ii) MOLECULE TYPE:
         (A) DESCRIPTION: peptide (iii) HYPOTHETICAL: NO (v) FRAGMENT TYPE: internal fragment (xi) SEQUENCE DESCRIPTION: SEQ ID NO: 26:

Val Trp Trp His Phe Val Gly Ala Asn Thr
1               5                   10

(2) INFORMATION FOR SEQ ID NO:27:

(i) SEQUENCE CHARACTERISTICS:
         (A) LENGTH: 10 amino acids
         (B) TYPE: amino acid
         (C) STRANDEDNESS: single
         (D) TOPOLOGY: linear (ii) MOLECULE TYPE:
         (A) DESCRIPTION: peptide (iii) HYPOTHETICAL: NO (v) FRAGMENT TYPE: internal fragment (xi) SEQUENCE DESCRIPTION: SEQ ID NO: 27:

Ala Asp Asp Gly Tyr Ile Leu Thr Met Ala
1               5                   10

(2) INFORMATION FOR SEQ ID NO:28:

(i) SEQUENCE CHARACTERISTICS:
         (A) LENGTH: 10 amino acids
         (B) TYPE: amino acid
         (C) STRANDEDNESS: single
         (D) TOPOLOGY: linear (ii) MOLECULE TYPE:
         (A) DESCRIPTION: peptide (iii) HYPOTHETICAL: NO (v) FRAGMENT TYPE: internal fragment (xi) SEQUENCE DESCRIPTION: SEQ ID NO: 28:

Arg Val Ser Glu His Ala Gly Tyr Met Ala
1               5                   10

(2) INFORMATION FOR SEQ ID NO:29:

(i) SEQUENCE CHARACTERISTICS:
         (A) LENGTH: 10 amino acids
         (B) TYPE: amino acid
         (C) STRANDEDNESS: single
         (D) TOPOLOGY: linear (ii) MOLECULE TYPE:
         (A) DESCRIPTION: peptide
```

(iii) HYPOTHETICAL: NO (v) FRAGMENT TYPE: internal fragment (xi) SEQUENCE DESCRIPTION: SEQ ID NO: 29:

Leu Val Asp Val Ala Val Ile Phe Gly Phe
1               5                   10

(2) INFORMATION FOR SEQ ID NO:30:

(i) SEQUENCE CHARACTERISTICS:
          (A) LENGTH: 10 amino acids
          (B) TYPE: amino acid
          (C) STRANDEDNESS: single
          (D) TOPOLOGY: linear (ii) MOLECULE TYPE:
          (A) DESCRIPTION: peptide (iii) HYPOTHETICAL: NO (v) FRAGMENT TYPE: internal fragment (xi) SEQUENCE DESCRIPTION: SEQ ID NO: 30:

Leu Leu Trp His Val Ile Gly Ala Asn Ser
1               5                   10

(2) INFORMATION FOR SEQ ID NO:31:

(i) SEQUENCE CHARACTERISTICS:
          (A) LENGTH: 10 amino acids
          (B) TYPE: amino acid
          (C) STRANDEDNESS: single
          (D) TOPOLOGY: linear (ii) MOLECULE TYPE:
          (A) DESCRIPTION: peptide (iii) HYPOTHETICAL: NO (v) FRAGMENT TYPE: internal fragment (xi) SEQUENCE DESCRIPTION: SEQ ID NO: 31:

Ser Asp Asp Gly Tyr Gln Met Gln Met Ala
1               5                   10

(2) INFORMATION FOR SEQ ID NO:32:

(i) SEQUENCE CHARACTERISTICS:
          (A) LENGTH: 10 amino acids
          (B) TYPE: amino acid
          (C) STRANDEDNESS: single
          (D) TOPOLOGY: linear (ii) MOLECULE TYPE:
          (A) DESCRIPTION: peptide (iii) HYPOTHETICAL: NO (v) FRAGMENT TYPE: internal fragment (xi) SEQUENCE DESCRIPTION: SEQ ID NO: 32:

Arg Thr Ala Asp His Ser Gly Tyr Met Ala
1               5                   10

(2) INFORMATION FOR SEQ ID NO:33:

(i) SEQUENCE CHARACTERISTICS:
          (A) LENGTH: 10 amino acids
          (B) TYPE: amino acid
          (C) STRANDEDNESS: single
          (D) TOPOLOGY: linear

```
    (ii) MOLECULE TYPE:
         (A) DESCRIPTION: peptide (iii) HYPOTHETICAL: NO (v) FRAGMENT TYPE: internal fragment (xi) SEQUENCE DESCRIPTION: SEQ ID NO: 33:

Leu Ala Asp Val Ala Val Ile Phe Gly Phe
1               5                   10

(2) INFORMATION FOR SEQ ID NO:34:

(i) SEQUENCE CHARACTERISTICS:
         (A) LENGTH: 10 amino acids
         (B) TYPE: amino acid
         (C) STRANDEDNESS: single
         (D) TOPOLOGY: linear (ii) MOLECULE TYPE:
         (A) DESCRIPTION: peptide (iii) HYPOTHETICAL: NO (v) FRAGMENT TYPE: internal fragment (xi) SEQUENCE DESCRIPTION: SEQ ID NO: 34:

Val Leu Trp His Val Ile Gly Ala Asn Ser
1               5                   10

(2) INFORMATION FOR SEQ ID NO:35:

(i) SEQUENCE CHARACTERISTICS:
         (A) LENGTH: 10 amino acids
         (B) TYPE: amino acid
         (C) STRANDEDNESS: single
         (D) TOPOLOGY: linear (ii) MOLECULE TYPE:
         (A) DESCRIPTION: peptide (iii) HYPOTHETICAL: NO (v) FRAGMENT TYPE: internal fragment (xi) SEQUENCE DESCRIPTION: SEQ ID NO: 35:

Ser Asp Asp Gly Tyr Ile Leu Gly Met Ala
1               5                   10

(2) INFORMATION FOR SEQ ID NO:36:

(i) SEQUENCE CHARACTERISTICS:
         (A) LENGTH: 10 amino acids
         (B) TYPE: amino acid
         (C) STRANDEDNESS: single
         (D) TOPOLOGY: linear (ii) MOLECULE TYPE:
         (A) DESCRIPTION: peptide (iii) HYPOTHETICAL: NO (v) FRAGMENT TYPE: internal fragment (xi) SEQUENCE DESCRIPTION: SEQ ID NO: 36:

Arg Val Ala Asp Arg Ala Gly Tyr Met Ser
1               5                   10

(2) INFORMATION FOR SEQ ID NO:37:

(i) SEQUENCE CHARACTERISTICS:
```

(A) LENGTH: 10 amino acids
            (B) TYPE:  amino acid
            (C) STRANDEDNESS:  single
            (D) TOPOLOGY:  linear (ii) MOLECULE TYPE:
            (A) DESCRIPTION:  peptide (iii) HYPOTHETICAL:  NO (v) FRAGMENT TYPE: internal fragment (xi) SEQUENCE DESCRIPTION:  SEQ ID NO: 37:

Leu Thr Asp Ala Val Val Ile Phe Gly Phe
1               5                   10

(2) INFORMATION FOR SEQ ID NO:38:

(i) SEQUENCE CHARACTERISTICS:
            (A) LENGTH: 10 amino acids
            (B) TYPE:  amino acid
            (C) STRANDEDNESS:  single
            (D) TOPOLOGY:  linear (ii) MOLECULE TYPE:
            (A) DESCRIPTION:  peptide (iii) HYPOTHETICAL:  NO (v) FRAGMENT TYPE: internal fragment (xi) SEQUENCE DESCRIPTION:  SEQ ID NO: 38:

Leu Leu Trp His Val Ile Gly Ala Asn Ser
1               5                   10

(2) INFORMATION FOR SEQ ID NO:39:

(i) SEQUENCE CHARACTERISTICS:
            (A) LENGTH: 10 amino acids
            (B) TYPE:  amino acid
            (C) STRANDEDNESS:  single
            (D) TOPOLOGY:  linear (ii) MOLECULE TYPE:
            (A) DESCRIPTION:  peptide (iii) HYPOTHETICAL:  NO (v) FRAGMENT TYPE: internal fragment (xi) SEQUENCE DESCRIPTION:  SEQ ID NO: 39:

Ser Asp Asp Gly Tyr Ile Leu Gly Met Ala
1               5                   10

(2) INFORMATION FOR SEQ ID NO:40:

(i) SEQUENCE CHARACTERISTICS:
            (A) LENGTH: 10 amino acids
            (B) TYPE:  amino acid
            (C) STRANDEDNESS:  single
            (D) TOPOLOGY:  linear (ii) MOLECULE TYPE:
            (A) DESCRIPTION:  peptide (iii) HYPOTHETICAL:  NO (v) FRAGMENT TYPE: internal fragment (xi) SEQUENCE DESCRIPTION:  SEQ ID NO: 40:

Arg Val Ala Asp His Ala Gly Tyr Met Ser
1               5                   10

(2) INFORMATION FOR SEQ ID NO:41:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE:
        (A) DESCRIPTION: peptide (iii) HYPOTHETICAL: NO (v) FRAGMENT TYPE: internal fragment (xi) SEQUENCE DESCRIPTION: SEQ ID NO: 41:

```
Ala Val Asp Gly Val Val Val Gly Gly Met
1               5                   10
```

(2) INFORMATION FOR SEQ ID NO:42:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE:
        (A) DESCRIPTION: peptide (iii) HYPOTHETICAL: NO (v) FRAGMENT TYPE: internal fragment (xi) SEQUENCE DESCRIPTION: SEQ ID NO: 42:

```
Ala Ile Trp Tyr Val Ile Gly Ala Asn Ser
1               5                   10
```

(2) INFORMATION FOR SEQ ID NO:43:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE:
        (A) DESCRIPTION: peptide (iii) HYPOTHETICAL: NO (v) FRAGMENT TYPE: internal fragment (xi) SEQUENCE DESCRIPTION: SEQ ID NO: 43:

```
Ser Asp Asp Gly Tyr Ile Leu Gln Met Ala
1               5                   10
```

(2) INFORMATION FOR SEQ ID NO:44:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE:
        (A) DESCRIPTION: peptide (iii) HYPOTHETICAL: NO (v) FRAGMENT TYPE: internal fragment (xi) SEQUENCE DESCRIPTION: SEQ ID NO: 44:

```
Arg Thr Ala Glu His Ala Gly Tyr Met Ala
 1               5                   10

(2) INFORMATION FOR SEQ ID NO:45:

(i) SEQUENCE CHARACTERISTICS:
        (A) LENGTH: 10095
        (B) TYPE: nucleic acid
        (C) STRANDEDNESS: double
        (D) TOPOLOGY: linear (ii) MOLECULE TYPE: Genomic DNA (iii) HYPOTHETICAL: NO (xi) SEQUENCE DESCRIPTION: SEQ ID NO: 45:
```

| | | | | | |
|---|---|---|---|---|---|
| GCGGCTGGCC | CAGGACGTCT | ACCCCAACCA | GCCCAATGTT | CGCCGCTACA | 50 |
| CGGTGGACCT | ACGGACCGCC | CTCTTCGCCG | ACCCGCGTTT | CGTCGTCGAG | 100 |
| GACATTGGCC | CGTTCGTGCT | GGCCATCCGC | AAGCCGCAGG | AGAGCGCGTG | 150 |
| ATGGCTACCG | AAGCCGCCCC | ACCCCGTATC | GCCGTCCGGC | TACCATCTAC | 200 |
| CTCCGTGCGC | GACGCGGGAG | CAAACTACCG | GATCGCCCGG | TACGTCGCTG | 250 |
| TGGTGGCGGG | TCTGCTAGGC | GCTGTGCTGG | CCATCGCCAC | CCCACTGCTG | 300 |
| CCGGTCAACC | AGACCACCGC | GCAATTGAAC | TGGCCCCAAA | ACGGCACGTT | 350 |
| CGCCAGTGTC | GAGGCACCGC | TGATTGGCTA | CGTGGCCACC | GACTTGAACA | 400 |
| TCACCGTCCC | CTGCCAGGCC | GCCGCCGGAC | TGGCCGGATC | GCAGAACACC | 450 |
| GGCAAGACGG | TGTTGTTGTC | AACGGTGCCC | AAGCAGGCGC | CTAAGGCCGT | 500 |
| CGATCGCGGG | CTGCTGCTGC | AACGGGCCAA | CGACGACCTG | GTGCTTGTGG | 550 |
| TGCGTAATGT | CCCGTTGGTC | ACCGCCCCGC | TGAGTCAGGT | GCTCGGCCCG | 600 |
| ACCTGTCAGC | GGTTGACATT | CACCGCGCAC | GCCGATCGGG | TCGCCGCCGA | 650 |
| ATTCGTCGGA | CTGGTGCAGG | GACCCAATGC | TGAGCACCCC | GGTGCACCGC | 700 |
| TGCGCGGTGA | GCGCAGCGGC | TACGACTTCC | GCCCGCAGAT | CGTCGGGGTG | 750 |
| TTCACCGACC | TGGCCGGGCC | GGCGCCACCG | GGTCTGAGCT | TCTCGGCGAG | 800 |
| CGTGGATACC | CGCTACAGCA | GCAGCCCCAC | GCCGCTGAAG | ATGGCCGCCA | 850 |
| TGATCCTCGG | GGTAGCGCTC | ACCGGCGCCG | CCCTGGTGGC | GCTGCACATC | 900 |
| CTGGACACCG | CCGACGGCAT | GCGGCACCGG | CGGTTCCTGC | CCGCGCGCTG | 950 |
| GTGGTCGACC | GGCGGTCTGG | ACACCCTGGT | TATCGCCGTG | CTGGTGTGGT | 1000 |
| GGCATTTCGT | CGGGGCCAAC | ACCTCCGACG | ACGGCTACAT | CCTGACCATG | 1050 |
| GCCCGGGTGT | CCGAGCATGC | GGGCTATATG | GCCAACTACT | ACCGCTGGTT | 1100 |
| CGGCACACCC | GAGGCGCCTT | TCGGCTGGTA | CTACGACCTG | CTGGCGCTGT | 1150 |
| GGGCTCATGT | CAGCACGGCC | AGTATCTGGA | TGCGCCTACC | CACCCTGGCG | 1200 |
| ATGGCGCTCA | CCTGCTGGTG | GGTAATCAGC | CGTGAGGTCA | TTCCCCGGCT | 1250 |
| GGGGCACGCC | GTCAAGACGA | GCCGGGCAGC | GGCGTGGACG | GCGGCGGGCA | 1300 |
| TGTTTCTGGC | TGTCTGGCTG | CCGCTGGACA | ACGGCCTTCG | GCCCGAGCCG | 1350 |
| ATCATCGCCC | TGGGCATCCT | GCTGACCTGG | TGCTCGGTGG | AGCGGGCGGT | 1400 |
| GGCCACCAGC | CGGCTGCTGC | CGGTGGCAAT | CGCCTGCATC | ATCGGTGCCT | 1450 |
| TGACCCTGTT | CTCCGGGCCG | ACGGGCATCG | CCTCGATCGG | TGCGCTGCTG | 1500 |
| GTCGCGATCG | GGCCGCTACG | GACCATCCTG | CACCGGCGTT | CCAGGCGGTT | 1550 |

-continued

| | |
|---|---|
| CGGCGTGCTA CCACTGGTGG CGCCGATCCT GGCCGCGGCC ACCGTCACCG | 1600 |
| CGATCCCGAT CTTTCGTGAT CAGACCTTCG CGGGCGAGAT CCAGGCCAAC | 1650 |
| CTCCTCAAGC GTGCCGTAGG GCCCAGCCTG AAGTGGTTCG ACGAACACAT | 1700 |
| CCGCTACGAG CGGCTGTTCA TGGCCAGCCC CGACGGCTCG ATCGCCCGCC | 1750 |
| GCTTCGCCGT GCTGGCCTTG GTGCTGGCGC TCGCGGTATC GGTGGCAATG | 1800 |
| TCGTTACGTA AGGGCCGCAT TCCAGGTACC GCTGCTGGAC CGAGCCGCCG | 1850 |
| CATCATCGGC ATCACGATCA TTTCCTTCCT CGCGATGATG TTCACCCCGA | 1900 |
| CAAAGTGGAC CCATCACTTC GGGGTGTTCG CGGGGTTGGC CGGGTCGCTG | 1950 |
| GGGGCGCTTG CCGCGGTCGC GGTGACGGGC GCTGCGATGC GCTCGCGGCG | 2000 |
| GAACCGGACC GTGTTCGCCG CCGTGGTGGT CTTCGTGTTG GCCCTGTCGT | 2050 |
| TCGCCAGTGT CAACGGCTGG TGGTACGTGT CCAACTTCGG TGTGCCATGG | 2100 |
| TCGAACTCGT TTCCGAAGTG GCGATGGTCG CTTACCACCG CACTCCTCGA | 2150 |
| GCTGACGGTG CTGGTGCTGC TGCTAGCGGC ATGGTTCCAC TTCGTCGCCA | 2200 |
| ACGGTGACGG GCGCCGAACA GCCAGGCCAA CCCGGTTTAG GGCACGACTA | 2250 |
| GCCGGAATTG TCCAGTCCCC GTTGGCAATT GCCACGTGGT TGCTGGTGCT | 2300 |
| TTTCGAGGTG GTATCGCTGA CCCAGGCGAT GATTTCCCAG TACCCGGCGT | 2350 |
| GGTCGGTTGG CCGGTCTAAC CTACAGGCTT TGGCCGGCAA GACCTGCGGG | 2400 |
| CTGGCCGAAG ACGTGCTGGT GGAGCTGGAT CCCAACGCAG GCATGCTGGC | 2450 |
| GCCGGTGACC GCGCCGTTGG CCGACGCCCT GGGAGCCGGC CTGTCTGAAG | 2500 |
| CCTTCACACC CAACGGCATT CCCGCCGACG TCACCGCCGA CCCGGTGATG | 2550 |
| GAACGTCCAG GGGATCGCAG TTTCCTCAAC GACGACGGGC TGATCACCGG | 2600 |
| CAGCGAACCC GGCACCGAAG GGGGCACCAC GGCCGCACCG GGAATCAACG | 2650 |
| GCTCCCGCGC CCGGCTGCCC TACAACCTGG ACCCGGCCCG TACACCGGTG | 2700 |
| CTGGGCAGCT GGCGAGCCGG CGTGCAGGTG CCCGCCATGC TGCGGTCGGG | 2750 |
| CTGGTACCGG CTGCCCACCA ACGAGCAGCG GGACAGGGCG CCGCTGCTGG | 2800 |
| TGGTGACGGC GGCCGGGCGA TTCGACTCCC GCGAGGTCCG GTTGCAGTGG | 2850 |
| GCCACCGACG AGCAAGCGGC CGCCGGACAC CACGGTGGGT CGATGGAATT | 2900 |
| CGCCGACGTC GGTGCCGCGC CGGCCTGGCG CAACCTGCGC GCACCACTGT | 2950 |
| CCGCCATCCC GAGCACCGCC ACCCAGGTCC GGTTGGTCGC CGACGACCAG | 3000 |
| GATCTGGCGC CGCAGCACTG GATCGCCCTC ACACCACCGC GGATTCCGCG | 3050 |
| GGTGCGCACG CTGCAGAACG TGGTGGGCGC AGCGGATCCG GTGTTCCTGG | 3100 |
| ACTGGCTGGT GGGGCTGGCA TTCCCCTGCC AACGCCCGTT CGGCCACCAA | 3150 |
| TACGGCGTCG ACGAGACACC CAAGTGGCGG ATCCTGCCGG ACCGGTTCGG | 3200 |
| CGCCGAAGCC AACTCACCGG TGATGGATCA CAATGGCGGT GGCCCGCTGG | 3250 |
| GCATCACCGA GCTGCTGATG CGCGCAACCA CGGTGGCCAG CTACCTCAAA | 3300 |
| GACGACTGGT TTAGGGACTG GGGCGCGTTA CAGCGGTTGA CGCCTTACTA | 3350 |
| CCCCGACGCC CAGCCCGCTG ATCTGAACCT AGGAACGGTG ACTCGCAGCG | 3400 |
| GGCTGTGGAG TCCGGCGCCG TTGCGCCGCG GCTAGAAGTG CCGTGGCCAC | 3450 |
| CGACTCGGCG ACAACCTCCG CGGCCCCGCA TCCTCACCGC CCTTAACCGC | 3500 |
| GTCGCCTACC ATCGAGCCTC GTGCCCCACG ACGGTAATGA GCGATCTCAC | 3550 |

| | |
|---|---|
| CGGATCGCAC GCCTAGCAGC CGTCGTCTCG GGAATCGCGG GTCTGCTGCT | 3600 |
| GTGCGGCATC GTTCCGCTGC TTCCGGTGAA CCAAACCACC GCGACCATCT | 3650 |
| TCTGGCCGCA GGGCAGCACC GCCGACGGCA ACATCACCCA GATCACCGCC | 3700 |
| CCTCTGGTAT CCGGGCGCC ACGCGCGCTG GACATCTCGA TCCCCTGCTC | 3750 |
| GGCCATCGCC ACGCTGCCCG CCAACGGCGG CCTGGTGCTG TCCACACTGC | 3800 |
| CGGCCGGTGG CGTGGATACC GGTAAGGCCG GGCTGTTCGT CCGCGCCAAC | 3850 |
| CAGGACACGG TCGTGGCGTT CCGCGACTCG GTGGCCGCGG TGGCGGCCCG | 3900 |
| CTCCACGATC GCAGCGGGAG GCTGTAGCGC GCTGCATATC TGGGCCGATA | 3950 |
| CCGGCGGCGC GGGCGCTGAT TTTATGGGTA TACCCGGCGG CGCCGGGACC | 4000 |
| CTGCCGCCGG AGAAGAAGCC ACAGGTTGGC GGCATCTTCA CCGACCTGAA | 4050 |
| GGTCGGAGCG CAGCCCGGGC TGTCGGCCCG CGTCGACATC GACACTCGGT | 4100 |
| TTATCACGAC GCCCGGCGCG CTCAAGAAGG CCGTGATGCT CCTCGGCGTG | 4150 |
| CTGGCGGTCC TGGTAGCCAT GGTGGGGCTG GCCGCGCTGG ACCGGCTCAG | 4200 |
| CAGGGGCCGC ACCCTGCGCG ACTGGCTGAC CCGATATCGC CCGCGGGTGC | 4250 |
| GGGTCGGATT CGCCAGCCGG CTCGCTGACG CAGCGGTGAT CGCGACCTTG | 4300 |
| TTGCTCTGGC ATGTCATCGG CGCCACCTCG TCCGATGACG GCTACCTTCT | 4350 |
| GACCGTCGCC CGGGTCGCCC CGAAGGCCGG CTATGTAGCC AACTACTACC | 4400 |
| GGTATTTCGG CACGACGGAG GCGCCGTTCG ACTGGTATAC ATCGGTGCTT | 4450 |
| GCCCAGCTGG CGGCGGTGAG CACCGCCGGC GTCTGGATGC GCCTGCCCGC | 4500 |
| CACCCTGGCC GGAATCGCCT GCTGGCTGAT CGTCAGCCGT TTCGTGCTGC | 4550 |
| GGCGGCTGGG ACCGGGCCCG GGCGGGCTGG CGTCCAACCG GGTCGCTGTG | 4600 |
| TTCACCGCTG GTGCGGTGTT CCTGTCCGCC TGGCTGCCGT TCAACAACGG | 4650 |
| CCTGCGTCCC GAGCCGCTGA TCGCGCTGGG TGTGCTGGTC ACGTGGGTGT | 4700 |
| TGGTGGAACG GTCGATCGCG CTCGGACGGC TGGCCCCGGC CGCGGTAGCC | 4750 |
| ATCATCGTGG CGACGCTTAC CGCGACGCTG GCACCGCAGG GGTTGATCGC | 4800 |
| GCTGGCCCCG CTGCTGACTG GTGCGCGCGC CATCGCCCAG AGGATCCGGC | 4850 |
| GCCGCCGGGC GACCGATGGA CTGCTGGCGC CGCTGGCGGT GCTGGCCGCG | 4900 |
| GCGTTGTCGC TGATCACCGT GGTGGTGTTT CGGGACCAGA CGCTGGCCAC | 4950 |
| GGTGGCCGAA TCGGCACGCA TCAAGTACAA GGTCGGCCCG ACCATCGCCT | 5000 |
| GGTACCAGGA CTTCCTGCGC TACTACTTCC TTACCGTGGA GAGCAACGTT | 5050 |
| GAGGGGTCGA TGTCCCGCCG GTTCGCGGTG CTGGTGTTGC TGTTCTGCCT | 5100 |
| GTTCGGGGTG CTGTTCGTGC TGCTGCGCG CGGCCGGGTG GCGGGGCTGG | 5150 |
| CCAGCGGCCC GGCCTGGCGA CTGATCGGCA CTACGGCGGT CGGCCTGCTG | 5200 |
| CTGCTCACGT TCACGCCAAC CAAGTGGGCC GTGCAGTTCG GCGCATTCGC | 5250 |
| CGGGCTGGCC GGGGTGTTGG GTGCGGTCAC CGCGTTCACC TTTGCCCGCA | 5300 |
| TCGGTCTACA TAGTCGACGC AACCTCACGC TGTACGTGAC CGCGTTGCTG | 5350 |
| TTCGTGCTGG CGTGGGCAAC CTCGGGCATC AACGGGTGGT TCTACGTCGG | 5400 |
| CAACTACGGG GTGCCGTGGT ATGACATCCA GCCCGTCATC GCCAGCCACC | 5450 |
| CGGTGACGTC GATGTTTCTG ACGCTGTCGA TCCTCACCGG ATTGCTGGCA | 5500 |
| GCCTGGTATC ACTTCCGGAT GGACTACGCC GGGCACACCG AAGTCAAAGA | 5550 |

-continued

| | |
|---|---|
| CAACCGGCGC AACCGCATCT TGGCCTCTAC GCCACTGCTG GTGGTCGCGG | 5600 |
| TGATCATGGT CGCAGGCGAA GTCGGCTCGA TGGCCAAGGC CGCGGTGTTC | 5650 |
| CGTTACCCGC TTTACACCAC CGCCAAGGCC AACCTGACCG CGCTCAGCAC | 5700 |
| CGGGCTGTCC AGCTGTGCGA TGGCCGACGA CGTGCTGGCC GAGCCCGACC | 5750 |
| CCAATGCCGG CATGCTGCAA CCGGTTCCGG GCCAGGCGTT CGGACCGGAC | 5800 |
| GGACCGCTGG GCGGTATCAG TCCCGTCGGC TTCAAACCCG AGGGCGTGGG | 5850 |
| CGAGGACCTC AAGTCCGACC CGGTGGTCTC CAAACCCGGG CTGGTCAACT | 5900 |
| CCGATGCGTC GCCCAACAAA CCCAACGCCG CCATCACCGA CTCCGCGGGC | 5950 |
| ACCGCCGGAG GGAAGGGCCC GGTCGGGATC AACGGGTCGC ACGCGGCGCT | 6000 |
| GCCGTTCGGA TTGGACCCGG CACGTACCCC GGTGATGGGC AGCTACGGGG | 6050 |
| AGAACAACCT GGCCGCCACG GCCACCTCGG CCTGGTACCA GTTACCGCCC | 6100 |
| CGCAGCCCGG ACCGGCCGCT GGTGGTGGTT TCCGCGGCCG GCGCCATCTG | 6150 |
| GTCCTACAAG GAGGACGGCG ATTTCATCTA CGGCCAGTCC CTGAAACTGC | 6200 |
| AGTGGGGCGT TCACCGGCCG GACGGCCGCA TCCAGCCACT GGGGCAGGTA | 6250 |
| TTTCCGATCG ACATCGGACC GCAACCCGCG TGGCGCAATC TGCGGTTTCC | 6300 |
| GCTGGCCTGG GCGCCGCCGG AGGCCGACGT GGCGCGCATT GTCGCCTATG | 6350 |
| ACCCGAACCT GAGCCCTGAG CAATGGTTCG CCTTCACCCC GCCCCGGGTT | 6400 |
| CCGGTGCTGG AATCTCTGCA GCGGTTGATC GGGTCAGCGA CACCGGTGTT | 6450 |
| GATGGACATC GCGACCGCAG CCAACTTCCC CTGCCAGCGA CCGTTTTCCG | 6500 |
| AGCATCTCGG CATTGCCGAG CTTCCGCAGT ACCGGATCCT GCCGGACCAC | 6550 |
| AAGCAGACGG CGGCGTCGTC GAACCTATGG CAGTCCAGCT CGACCGGCGG | 6600 |
| TCCGTTCCTG TTCACCCAGG CGCTGCTGCG CACCTCGACG ATCGCCACGT | 6650 |
| ACCTGCGTGG GGACTGGTAT CGCGACTGGG GATCGGTGGA GCAGTACCAC | 6700 |
| CGGCTGGTGC CGGCCGATCA GGCTCCAGAC GCCGTTGTCG AGGAGGGCGT | 6750 |
| GATCACTGTG CCCGGCTGGG GTCGGCCAGG ACCGATCAGG GCGCTGCCAT | 6800 |
| GACACAGTGC GCGAGCAGAC GCAAAAGCAC CCCAAATCGG GCGATTTTGG | 6850 |
| GGGCTTTTGC GTCTGCTCGC GGGACGCGCT GGGTGGCCAC CATCGCCGGG | 6900 |
| CTGATTGGCT TTGTGTTGTC GGTGGCGACG CCGCTGCTGC CCGTCGTGCA | 6950 |
| GACCACCGCG ATGCTCGACT GGCCACAGCG GGGGCAACTG GGCAGCGTGA | 7000 |
| CCGCCCCGCT GATCTCGCTG ACGCCGGTCG ACTTTACCGC CACCGTGCCG | 7050 |
| TGCGACGTGG TGCGCGCCAT GCCACCCGCG GCGGGGTGG TGCTGGGCAC | 7100 |
| CGCACCCAAG CAAGGCAAGG ACGCCAATTT GCAGGCGTTG TTCGTCGTCG | 7150 |
| TCAGCGCCCA GCGCGTGGAC GTCACCGACC GCAACGTGGT GATCTTGTCC | 7200 |
| GTGCCGCGCG AGCAGGTGAC GTCCCCGCAG TGTCAACGCA TCGAGGTCAC | 7250 |
| CTCTACCCAC GCCGGCACCT TCGCCAACTT CGTCGGGCTC AAGGACCCGT | 7300 |
| CGGGCGCGCC GCTGCGCAGC GGCTTCCCCG ACCCCAACCT GCGCCCGCAG | 7350 |
| ATTGTCGGGG TGTTCACCGA CCTGACCGGG CCCGCGCCGC CGGGCTGGC | 7400 |
| GGTCTCGGCA ACCATCGACA CCCGGTTCTC CACCCGGCCG ACCACGCTGA | 7450 |
| AACTGCTGGC GATCATCGGG GCGATCGTGG CCACCGTCGT CGCACTGATC | 7500 |
| GCGTTGTGGC GCCTGGACCA GTTGGACGGG CGGGGCTCAA TTGCCCAGCT | 7550 |

```
CCTCCTCAGG CCGTTCCGGC CTGCATCGTC GCCGGCGGC  ATGCGCCGGC      7600

TGATTCCGGC AAGCTGGCGC ACCTTCACCC TGACCGACGC CGTGGTGATA      7650

TTCGGCTTCC TGCTCTGGCA TGTCATCGGC GCGAATTCGT CGGACGACGG      7700

CTACATCCTG GGCATGGCCC GAGTCGCCGA CCACGCCGGC TACATGTCCA      7750

ACTATTTCCG CTGGTTCGGC AGCCCGGAGG ATCCCTTCGG CTGGTATTAC      7800

AACCTGCTGG CGCTGATGAC CCATGTCAGC GACGCCAGTC TGTGGATGCG      7850

CCTGCCAGAC CTGGCCGCCG GGCTAGTGTG CTGGCTGCTG CTGTCGCGTG      7900

AGGTGCTGCC CCGCCTCGGG CCGGCGGTGG AGGCCAGCAA ACCCGCCTAC      7950

TGGGCGGCGG CCATGGTCTT GCTGACCGCG TGGATGCCGT TCAACAACGG      8000

CCTGCGGCCG GAGGGCATCA TCGCGCTCGG CTCGCTGGTC ACCTATGTGC      8050

TGATCGAGCG GTCCATGCGG TACAGCCGGC TCACACCGGC GGCGCTGGCC      8100

GTCGTTACCG CCGCATTCAC ACTGGGTGTG CAGCCCACCG GCCTGATCGC      8150

GGTGGCCGCG CTGGTGGCCG GCGGCCGCCC GATGCTGCGG ATCTTGGTGC      8200

GCCGYCATCG CCTGGTCGGC ACGTTGCCGT TGGTGTCGCC GATGCTGGCC      8250

GCCGGCACCG TCATCCTGAC CGTGGTGTTC GCCGACCAGA CCCTGTCAAC      8300

GGTGTTGGAA GCCACCAGGG TTCGCGCCAA AATCGGGCCG AGCCAGGCGT      8350

GGTATACCGA GAACCTGCGT TACTACTACC TCATCCTGCC CACCGTCGAC      8400

GGTTCGCTGT CGCGGCGCTT CGGCTTTTTG ATCACCGCGC TATGCCTGTT      8450

CACCGCGGTG TTCATCATGT TGCGGCGCAA GCGAATTCCC AGCGTGGCCC      8500

GCGGACCGGC GTGGCGGCTG ATGGGCGTCA TCTTCGGCAC CATGTTCTTC      8550

CTGATGTTCA CGCCCACCAA GTGGGTGCAC CACTTCGGGC TGTTCGCCGC      8600

CGTAGGGGCG GCGATGGCCG CGCTGACGAC GGTGTTGGTA TCCCCATCGG      8650

TGCTGCGCTG GTCGCGCAAC CGGATGGCGT TCCTGGCGGC GTTATTCTTC      8700

CTGCTGGCGT TGTGTTGGGC CACCACCAAC GGCTGGTGGT ATGTCTCCAG      8750

CTACGGTGTG CCGTTCAACA GCGCGATGCC GAAGATCGAC GGGATCACAG      8800

TCAGCACAAT CTTTTTCGCC CTGTTTGCGA TCGCCGCCGG CTATGCGGCC      8850

TGGCTGCACT TCGCGCCCCG CGGCGCCGGC GAAGGGCGGC TGATCCGCGC      8900

GCTGACGACA GCCCCGGTAC CGATCGTGGC CGGTTTCATG GCGGCGGTGT      8950

TCGTCGCGTC CATGGTGGCC GGGATCGTGC GACAGTACCC GACCTACTCC      9000

AACGGCTGGT CCAACGTGCG GGCGTTTGTC GGCGGCTGCG GACTGGCCGA      9050

CGACGTACTC GTCGAGCCTG ATACCAATGC GGGTTTCATG AAGCCGCTGG      9100

ACGGCGATTC GGGTTCTTGG GGCCCCTTGG GCCCGCTGGG TGGAGTCAAC      9150

CCGGTCGGCT TCACGCCCAA CGGCGTACCG GAACACACGG TGGCCGAGGC      9200

GATCGTGATG AAACCCAACC AGCCCGGCAC CGACTACGAC TGGGATGCGC      9250

CGACCAAGCT GACGAGTCCT GGCATCAATG GTTCTACGGT GCCGCTGCCC      9300

TATGGGCTCG ATCCCGCCCG GGTACCGTTG GCAGGCACCT ACACCACCGG      9350

CGCACAGCAA CAGAGCACAC TCGTCTCGGC GTGGTATCTC CTGCCTAAGC      9400

CGGACGACGG GCATCCGCTG GTCGTGGTGA CCGCCGCGGG CAAGATCGCC      9450

GGCAACAGCG TGCTGCACGG GTACACCCCC GGGCAGACTG TGGTGCTCGA      9500

ATACGCCATG CCGGGACCCG GAGCGCTGGT ACCCGCCGGG CGGATGGTGC      9550
```

```
CCGACGACCT ATACGGAGAG CAGCCCAAGG CGTGGCGCAA CCTGCGCTTC      9600

GCCCGAGCAA AGATGCCCGC CGATGCCGTC GCGGTCCGGG TGGTGGCCGA      9650

GGATCTGTCG CTGACACCGG AGGACTGGAT CGCGGTGACC CCGCCGCGGG      9700

TACCGGACCT GCGCTCACTG CAGGAATATG TGGGCTCGAC GCAGCCGGTG      9750

CTGCTGGACT GGGCGGTCGG TTTGGCCTTC CCGTGCCAGC AGCCGATGCT      9800

GCACGCCAAT GGCATCGCCG AAATCCCGAA GTTCCGCATC ACACCGGACT      9850

ACTCGGCTAA GAAGCTGGAC ACCGACACGT GGGAAGACGG CACTAACGGC      9900

GGCCTGCTCG GGATCACCGA CCTGTTGCTG CGGGCCCACG TCATGGCCAC      9950

CTACCTGTCC CGCGACTGGG CCCGCGATTG GGGTTCCCTG CGCAAGTTCG      10000

ACACCCTGGT CGATGCCCCT CCCGCCCAGC TCGAGTTGGG CACCGCGACC      10050

CGCAGCGGCC TGTGGTCACC GGGCAAGATC CGAATTGGTC CATAG           10095
```

(2) INFORMATION FOR SEQ ID NO:46:

(i) SEQUENCE CHARACTERISTICS:
        (A) LENGTH: 9960
        (B) TYPE: nucleic acid
        (C) STRANDEDNESS: double
        (D) TOPOLOGY: linear (ii) MOLECULE TYPE: Genomic DNA (iii) HYPOTHETICAL: NO (xi) SEQUENCE DESCRIPTION: SEQ ID NO: 46:

```
TGTTCGACGA TCCGCGGTTC GAGGTGTCCG ACCACGGTCC GTTCGTGCTC      50

GCGATCAGGA AACCCGGGGG AAAGCCGGAG ACCGATGGCC ACTGATATCC      100

CGTTAGCATC GAAGCCCGTG ACCGGTCCGC ATGCAGCGGG TGGCAGCAAC      150

CACCGCACCG CGCGGCTCGT CGCGATCATC GCCGGACTTC TCGGCACGCT      200

GATGGCGATC GCGACGCCGC TGCTGCCGGT CGAGCAGACC ACCGCCGAGC      250

TCAACTGGCC GCAGAACGGC GTCTGGCAGA GCGTCGACGC GCCGCTGATC      300

GGCTACGTCG CGACCGACCT GACCGTCACC GTGCCGTGCC AGGCCGCCGC      350

GGGCCTGGTG GGACCGGAGA ACCGCAACCG CAGCGTGCTG TTGTCGACGG      400

TGCCCAAGCA GGCCCCCAAG GCCATCGACC GCGGCCTGCT GATCGAACGC      450

ATCAACAACG ACCTCACGGT CATCGTGCGC AACACCCCGG TCGTCAGCGC      500

ACCGCTGGAG CAGGTGCTCA GCCCCGACTG CCGGTACCTG ACGTTCACCG      550

CGCACGCCGA CAAGGTGACC GGTGAGTTCG TCGGCCTCAC GCAGGGTCCC      600

GATGACGACG ACCCGGGCGA GGCGGTGCGC GGCGAGCGCA GCGGCTACGA      650

CTTCCGTCCC CAGATCGTCG GTGTGTTCAC CGACCTGTCC GGCCCGGCGC      700

CCGAAGGGCT GCAGTTGTCG GCGACCATCG ACACGCGCTA CAGCACGTCG      750

CCGACCCTGC TGAAACTGCT CGCGATGATC GTGGGCGTCG CGATGACCGT      800

CATCGCGCTC GGCGCGCTGC ACGTGCTGGA CTGCGCCGAC GGCCGGCGCC      850

ACAAGCGCTT CCTGCCGTCG CGCTGGTGGT CGATGACGCC GCTGGACGGG      900

CTGGTCAGCG CGATGCTGGT GTGGTGGCAC TTCGTCGGCG CCAACACGGC      950

CGACGACGGC TACATCCTGA CCATGGCCCG TGTGTCCGAG CACGCCGGCT      1000

ACATGGCCAA CTACTACCGC TGGTTCGGTA CGCCTGAGTC GCCGTTCGGC      1050
```

-continued

| | |
|---|---|
| TGGTACTACG ACCTGCTGGC GTTGTGGGCG CACGTGTCGA CGGCCAGCGT | 1100 |
| GTGGATGCGC TTCCCCACGC TGCTCATGGG TCTGGCCTGC TGGTGGGTGA | 1150 |
| TCAGCCGCGA GGTCATCCCG CGCCTGGGCG CCGCCGCCAA GCACAGCCGC | 1200 |
| GCCGCGGCAT GGACCGCCGC GGGCCTGTTC CTGGCGTTCT GGCTGCCGCT | 1250 |
| CAACAACGGG TTGCGCCCCG AGCCCATCAT CGCGCTGGGC ATCCTGCTGA | 1300 |
| CGTGGTGCTC GGTGGAGCGC GGCGTCGCGA CCAGCAGGCT GCTGCCGGTG | 1350 |
| GCCGTCGCCA TCATCATCGG TGCACTCACG CTGTTCTCCG GCCCCACCGG | 1400 |
| CATCGCCGCT GTCGGCGCCC TGCTGGTCGC CATCGGACCG CTGAAAACCA | 1450 |
| TTGTGGCCGC GCATGTTTCA CGGTTCGGCT ATTGGGCACT GCTGGCGCCG | 1500 |
| ATCGCCGCGG CGGGCACCGT CACGATCTTC CTGATCTTCC GCGACCAGAC | 1550 |
| CCTGGCCGCC GAACTGCAGG CCAGCAGCTT CAAGTCGGCC GTCGGCCCCA | 1600 |
| GCCTGGCCTG GTTCGACGAG CACATCCGCT ACTCACGCCT GTTCACCACA | 1650 |
| AGCCCCGACG GTTCGGTGGC GCGGCGCTTC GCGGTGCTCA CGCTGCTGCT | 1700 |
| CGCGCTGGCG GTGTCGATCG CGATGACGCT GCGCAAGGGC CGCATCCCCG | 1750 |
| GCACCGCGCT GGGCCCGAGC AGACGCATCA TCGGCATCAC GATCATCTCG | 1800 |
| TTCCTCGCGA TGATGTTCAC CCCGACCAAG TGGACCCACC AATTCGGTGT | 1850 |
| GTTCGCCGGC CTCGCGGGGT GCCTCGGCGC CCTGGCCGCC GTCGCGGTCA | 1900 |
| CCACGACCGC GATGAAGTCG CGGCGTAACC GCACGGTGTT CGGCGCGGCA | 1950 |
| GTGCTGTTCG TGACGGCGCT GTCGTTCGCG ACGGTCAACG GCTGGTGGTA | 2000 |
| CGTGTCCAAT TTCGGTGTGC CCTGGTCGAA CTCGTTCCCC GAGTTCAAGT | 2050 |
| TCGGGTTCAC CACGATGCTG CTGGGCCTGT CGGTGCTCGC GCTGCTGGTC | 2100 |
| GCGGCATGGT TCCACTTCAG CGGGCGCGAC GTCTCGCCCG ACCGGCCGCA | 2150 |
| ACGGCGCTGG CAGCGCCTTC TGGTCGCCCC GCTCGCGGTC GCCACGTGGG | 2200 |
| CACTGGTGAT CTTCGAGGTG GTCTCGCTGA CGCTGGGGAT GATCAACCAG | 2250 |
| TACCCGGCGT GGTCGGTGGG CCGCTCCAAC CTCAACGCCC TGACCGGCAA | 2300 |
| GACCTGCGGA CTGGCCAACG ACGTGCTGGT CGAGCAGAAC GCCAACGCGG | 2350 |
| GCATGCTCAC CCCGATCGGT GAGCCGGCCG GTCAGGCGCT CGGCGCCGTG | 2400 |
| ACCTCGCTGG GCTTCGGGCC GAACGGCATC CCCTCGGATG TCTCCGCGGA | 2450 |
| CCCCGTCATG GAGCAGCCCG GCACGGACAA CTTCGCCGAC AGCGACTCCG | 2500 |
| GCGTCGTCAC CGGCACCGAG GTCGGCACGG AAGGCGGCAC CACAGCTGCC | 2550 |
| GCGGGCATCA ACGGATCCCG CGCGCGCCTG CCGTACGGCC TGAACCCGGC | 2600 |
| CACCACGCCG GTGCTCGGTT CGTGGCGTTC GGGCACACAG CAGCCCGCGG | 2650 |
| TGCTGCGCTC GGCGTGGTAC CGGCTGCCCG ACCGCGACCA GGCGGGCCCG | 2700 |
| CTGCTCGTGG TGTCGGCCGC CGGTCGGTTC GACCAGGGCG AGGTCGAGGT | 2750 |
| GCAGTGGGCC ACCGACGAGC AGGCCGCGGC CAACGAGCCG GGCGGCAGCA | 2800 |
| TCACCTTCGG TGACGTCGGC GCGGCCCCGG CCTGGCGCAA CCTGCGCGCC | 2850 |
| CCGCTGAGCT CGATCCCGCC CGAGGCCACC CAGATCCGGC TGGTCGCCAG | 2900 |
| CGACGACGAT CTCGCACCCC AGCACTGGAT CGCCCTGACC CCGCCGCGCA | 2950 |
| TCCCCGAGCT GCGCACGCTG CAGGAGGTCG TCGGATCGTC CGACCCGGTG | 3000 |
| ATGCTGGACT GGCTCGTAGG CCTGGCGTTC CCGTGCCAGC GGCCGTTCGA | 3050 |

| | |
|---|---|
| CCACCGCTAC GGCGTCGTCG AGGTGCCCAA GTGGCGCATC CTGCCGGACC | 3100 |
| GGTTCGGCGC CGAGGCCAAT TCGCCGGTCA TGGACTACCT GGGCGGCGGC | 3150 |
| CCGCTCGGCA TCACCGAGCT GCTGCTGCGC CCGTCGTCGG TGCCGACCTA | 3200 |
| CCTCAAGGAC GACTGGTACC GCGACTGGGG CTCGTTGCAG CGGCTGACGC | 3250 |
| CGTGGTACCC GGACGCCCAG CCGGCGCGCC TGGACCTCGG CACGGCCACG | 3300 |
| CGCAGCGGCT GGTGGAGCCC GGCGCCCCTG CGGCTGAGTT GAGCGGCTGA | 3350 |
| GCTAGCGGCT GAGCGATCAC GGTAGGGCCG ACGCGCGCCC GCATGGCCGA | 3400 |
| CGCTCACATG CGGGTCGCAT ACCATCGAGC CTCGTGCCGG GCGATGAACA | 3450 |
| GCGTGAGCGA ACAGCAGATG ACGCAGTGAC CGAACCGTCC CGCATCGCAC | 3500 |
| GCCTGATCGC TGTCGTCGCC GGCATCGCGG GCGTGTTGTT GTGCGGTCTG | 3550 |
| GTTCCACTGC TCCCGGTGGA GGAGACCACC GCGACCGTCC TGTGGCCGCA | 3600 |
| GGGTGTGGGT GCCGACGGCA ACGTCACCGA ACTGACGGCC CCGCTGGTGG | 3650 |
| CCGGGGCGCC GCGGGCACTC GACGTCACGA TCCCGTGCCG CGCCGTGGCC | 3700 |
| GAGCTTCCCG CCGACGGCGG CGTGGTGTTC TCGACGAACC CGGCAGGCGG | 3750 |
| CATCGAGGCC GGCCGCAACG GCATGTTCAT CCGCGCCAAC GCCGACGTGG | 3800 |
| TCTACGTCGC GTTCCGCGAC ACGGTCGCCG CGGTCGCACC GCGTGAGGCC | 3850 |
| GTCGATTCCG GCGCGTGCAG TGAGATCCAC GTCTGGGCCG ACGTCAGCGC | 3900 |
| GGTGGGCGCC GACTTCGCCG GTATCCCCGA CGCCAGCGGA ACCCTGCCCG | 3950 |
| TCGACAAGCG CCCCCAGGTC TCGGGTGTCT TCACCGACCT CAAGGTGCCC | 4000 |
| GCGCAGCCCG GCCTGGCCGC GCGCATCGAC ATCGACACCC GCTTCATCAC | 4050 |
| GTCACCGACC CTGCTGAAGA CCGCCGTGAT GGTGCTCGGC CTCGCGTGCG | 4100 |
| TCATCGGGTC GATCGTCGCG CTGGCCCTGT TGGACCGCGG ATGGCGCAGG | 4150 |
| CGCCCNGCGC GCACGCGCGG ACGCGCCGGG CTGTGGACGT GGATCACCGA | 4200 |
| CACCGGCGTG ATCGGCGGCC TGCTCATCTG GCACATCGTC GGCGCGCCCA | 4250 |
| CGTCCGACGA CGGCTACAAC ATGACCATCG CCCGGGTGGC GTCCGAGGCG | 4300 |
| GGTTACACGA CGAACTACTA CCGCTACTTC GGCGCGTCCG AGGCCCCGTT | 4350 |
| CGACTGGTAC CAGAGCGTGC TGTCGCACCT GGCCTCGATC AGCACCGCGG | 4400 |
| GCGTGTGGAT GCGGCTGCCC GCCACGGCGG CCGCTATCGC GACGTGGCTG | 4450 |
| ATCATCAGCC GCTGCGTGCT GCCCCGCATC GGCAGGCGCG TCGCGGCCAA | 4500 |
| CCGCGTCGCG ATGCTCACCG CGGGTGCGAC GTTCCTGGCC GCGTGGCTGC | 4550 |
| CGTTCAACAA CGGTTTGCGT CCCGAACCGC TGATCGCGTT CGCGGTGATC | 4600 |
| ACGGTGTGGA TGCTGGTGGA GAACTCCATC GGCACGCGGC GCCTGTGGCC | 4650 |
| CGCGGCCGTC GCGATCGTCA TCGCGATGTT CTCCGTCACA CTCGCCCCGC | 4700 |
| AGGGCCTGAT CGCGCTGGCG CCGCTGCTGG TCGGCGCGCG CGCCATCGGC | 4750 |
| CGCGTCGTCA CCGCCCGCCG TGCGGCACCG GGATCCTGGC GTCCCTGCCC | 4800 |
| GCTCGCGGCG TCGGTCGCCG TGGTCTTCGT GATCATCTTC CGCGATCAGA | 4850 |
| CCCTGGCCAC GGTCGCCGAG TCGGTGCGCA TCAAGTACGT CGTGGGACCG | 4900 |
| ACCATCCCCT GGTACCAGGA ATTCCTGCGG TACTACTTCC TCACGGTCGA | 4950 |
| GGACAGCGTC GACGGATCCC TGACCCGCCG ATTCGCGGTG CTGGTGCTGC | 5000 |
| TGCTGTGCCT GTTCGGCCTC ATCATGGTGC TGCTGCGCCG CGGCCGGGTG | 5050 |

-continued

| | |
|---|---|
| CCCGGCGCGG TGAGCGGGCC GCTGTGGCGG CTGTGCGGAT CGACCGCGAT | 5100 |
| CGGCCTGCTG CTGTTGATCC TCACCCCCAC CAAGTGGGCG ATCCAGTTCG | 5150 |
| GCGCGTTCGC GGGCCTGGCC GGCGCCCTCG GTGGTGTGAC GGCATTCGCG | 5200 |
| TTCGCGCGCG TGGGCCTGCA CAGCCGACGC AACCTCGCGC TGTACGTCAC | 5250 |
| CGCGCTGCTG TTCATCCTGG CGTGGGCCAC CTCGGGCCTC AACGGCTGGT | 5300 |
| TCTACGTCGG CAACTACGGC GTGCCGTGGT TCGACAAGCA GCCTGTGATC | 5350 |
| GCGCATTACC CGGTCACCAC GATCTTCCTG GTGCTCGCGA TCGTCGGCGG | 5400 |
| TCTGCTCGCA GGCTGGCTGC ACTTCCGCAT GGACTACGCG GGGCACACCG | 5450 |
| AGGTGGCCGA CACCGGCAGA AACCGCGCGC TCGCCTCGAC GCCGCTGTTG | 5500 |
| ATCGTCGCGA CCATCATGGT GGTGCTCGAA CTCGGCTCGA TGGTCAAGGC | 5550 |
| CACCGTGGGC CGCTACCCCG TCTACACCGT GGGCTCGGCC AACATCGCCG | 5600 |
| CGCTGCGCTC GGCCGGCGAC AGCTGTGCGA TGGCCGACGC CGTGCTGGTC | 5650 |
| GAGGCCGACC CCAACGAGGG CATGCTGCAA CCGGTTCCGG GCCAGCGGTT | 5700 |
| CGGTGACTAC GGCCCGCTGG GCGGCGAGGA CCCCGTCGGC TTCACCCCCA | 5750 |
| GCGGCGTCAG CGAACACCTC GAACCCGAGC CGTCGGGAC CAACCCGGGC | 5800 |
| ACCCCGAACT CCGAGGGGCC GGTCGACAAG CCCAACATCG GTATCGCCTA | 5850 |
| CGCCGGGGAC ACCGGCGGCG GCTACGCCCC CGAGGGCGTC AACGGGTCGC | 5900 |
| GGGTGTTCCT GCCCTTCGGC CTGGACCCGT CCCGCACCCC GGTGATGGGC | 5950 |
| AGCTACGGCG AGAACAAGCT GGCCGCCAAG GCCACGTCGG CCTGGTACCA | 6000 |
| GCTGCCGCCC CGCACGCCGG ACCGCCCGCT GGTGACCGTC GCCGCGGCAG | 6050 |
| GCGCCATCTG GTACTACGAG GAAGACGGCT CGTTCAACTA CGGCCAGTCG | 6100 |
| CTCAAGCTGC AGTGGGGTGT GCACCGGCCC GACGGCACCT ACCAGGCGCT | 6150 |
| GTCGGAGGTC CAGCCCATCG ACATCTTCCA GCAGAAGGCG TGGCGCAACC | 6200 |
| TGCGGTTCCC GCTCGCGTGG GCGCCGCCGG AGGCCAACGT CGCGCGCATC | 6250 |
| GTCGCCGACG ACCCCAACCT GTCCGAGGAC CAGTGGTGCG CGTTCACGCC | 6300 |
| GCCGCGCGTT CCGGTGCTGC AGACCGCGCA GCAGTTCCTC GGATCGCAGA | 6350 |
| CCCCGGTGCT CATGGACATC GCCACGGCCG CGAACTTCCC GTGCCAGCGG | 6400 |
| CCATTCGCCG AGCGGCTCGG TGTTGCCGAG TTGCCCGAGT ACCGCATCAT | 6450 |
| CCCCAACTTC AAGCAGATGG TGGTGTCGTC CAACCAGTGG CAGTCCGCCG | 6500 |
| CCGACGGTGG GCCGTTCCTG TTCATCCAGG CGCTGCTGAG GACCGAGGCG | 6550 |
| ATCCCGACCT ATCTGCGTGA CGACTGGTAC CGCGACTGGG GCTCGATCGA | 6600 |
| GCGCTACATC CGGGTGGTAC CGCAGGAGCA GGCGCCCACA GCCGCCATCG | 6650 |
| AGGAAGGATC GACGCGAGTG TTCGGATGGA GTCGCGGCGG ACCGATCAGG | 6700 |
| GCACTGCCGT GAGCGGCAAC ATGGATGAAG CCGTGAGCGG CAACATGGAT | 6750 |
| GAAGCCGTGA GCGCCGGCAA GGACGTGCGG ATCGCACGCT GGGTCGCCAC | 6800 |
| CATCGCGGGC CTGCTCGGAT TCGTGCTCTC CGTGTCCATC CCGCTGCTGC | 6850 |
| CGGTCACGCA GACCACGGCC ACGCTGAACT GGCCGCAGCA GGGCAGGCTC | 6900 |
| GACAACGTCA CCGCTCCGCT GATCTCGCAG GCCCCGTTGG AGCTGACCGC | 6950 |
| GACCGTGCCG TGCTCGGTGG TGCGCGACCT GCCCCCCGAG GGCGGCCTGG | 7000 |
| TGTTCGGCAC CGCACCCGCC GAGGGCCGCG ACGCCGCACT CAACGCGATG | 7050 |

```
CTGGTCAACG TCACCGAGAC CCGCGTCGAC GTGATCGTGC GCAACGTCGT           7100

CGTCGCGAGC GTGAACCGCG ACCGCGTCGC GGGACCTGAC TGCCAACGCA           7150

TCGAGATCAC GTCGAACCTG GATGGCACCT ACGCCGATTT CGTCGGTCTC           7200

ACACAGATTT CCGGTGAGGA CGCGGGCAAG CTGCAGCGCA CCGGCTACCC           7250

CGACCCGAAT CTGCGGCCCG CGATCGTCGG TGTGTTCACC GACCTCACCG           7300

GCCCTGCGCC GCAGGGACTG TCGGTGTCGG CGGAGATCGA CACGCGCTTC           7350

ACGACGCACC CCACGGCGCT CAAGCTCGCG GCCATGCTGC TGGCGATCGT           7400

GTCGACCGTC ATCGCGCTGC TCGCGCTGTG GCGCCTCGAC CGGCTCGACG           7450

GGCGGCGCAT GCACCGCCTG ATCCCGACGC GCTGGCGCAC GGTCACCGCG           7500

GTCGACGGCG TGGTGGTCGG CGGCATGGCG ATCTGGTACG TGATCGGCGC           7550

CAACTCGTCC GACGACGGCT ACATCCTGCA GATGGCGCGC ACGGCCGAGC           7600

ACGCGGGCTA CATGGCGAAC TACTTCCGCT GGTTCGGCAG CCCCGAGGAC           7650

CCGTTCGGCT GGTACTACAA CGTGCTGGCG CTCATGACCA AGGTGAGCGA           7700

CGCCAGCATC TGGATCCGAT TGCCCGACTT GATCTGTGCC CTGATCTGCT           7750

GGCTGCTGCT GTCCCGTGAG GTGCTGCCGC GGCTGGGACC CGCGGTGGCC           7800

GGCAGTCGCG CGGCGATGTG GGCCGCGGGC CTGGTGCTGC TTGGTGCGTG           7850

GATGCCGTTC AACAACGGCC TGCGCCCCGA GGGCCAGATC GCCACGGGCG           7900

CGCTGATCAC CTATGTCCTG ATCGAACGCG CCGTCACCTC GGGCCGGCTC           7950

ACCCCGGCGG CGCTGGCCAT CACGACGGCC GCGTTCACGC TCGGTATCCA           8000

GCCGACCGGT CTGATCGCCG TCGCCGCACT GCTGGCCGGT GGCCGTCCGA           8050

TCCTGCGCAT CGTCATCCGC CGCCGTCGCC TCGACGGGAC CTGGCCGCTG           8100

ATCGCGCCAC TGCTGGCCGC GGGCACCGTG ATCCTGGCCG TGGTGTTCGC           8150

CGACCAGACC ATCGCAACGG TGCTGGAGGC CACCAGGATC CGCACCGCGA           8200

TCGGGCCCAG CCAGGAGTGG TGGACCGAGA AGCTGCGCTA CTACTACCTG           8250

ATCCTGCCGA CCACCGACGG CGCGATCTCG CGGCGCGTGG CGTTCGTGTT           8300

CACCGCGATG TGCCTGTTCC CCTCGCTGTT CATGATGTTG CGGCGCAAGC           8350

ACATCGCGGG CGTCGCACGC GGCCCGGCCT GGCGCCTAAT GGGCATCATC           8400

TTCGCCACCA TGTTCTTCCT GATGTTCACG CCCACCAAGT GGACCCACCA           8450

CTTCGGCCTG TTCGCCGCGG TGGGCGGTGC GATGGCCGCG CTGGCGACCG           8500

TGCTGGTGTC GCCCACGGTG CTGCGCTCGG CGCGCAACCG GATGGCGTTC           8550

CTGTCGCTCG TGTTGTTCGT GCTGGCGTTC TGCTTCGCCT CCACCAACGG           8600

CTGGTGGTAC GTGTCGAACT TCGGTGCGCC GTTCAACAAT TCGGTGCCCA           8650

AGGTCGGCGG TGTCCAGATC AGCGCGATCT TCTTCGCGCT GTCGGCGATC           8700

GCGGCCCTGT GGGCGTTCTG GTTGCACCTG ACGCGTCGCA CCGAATCCCG           8750

TGTGGTGGAC CGGTTGACCG CGGCGCCCAT CCCCGTCGCG GCCGGGTTCA           8800

TGGTCGTGGT GATGATGGCG TCCATGGCGA TCGGCGTGGT GCGCCAGTAC           8850

CCGACGTACT CCAACGGGTG GGCCAACATC CGCGCGTTCG CGGGCGGTTG           8900

CGGCCTGGCC GACGACGTTC TGGTGGAACC GGATTCGAAC GCGGGCTTCC           8950

TCACGCCGCT GCCCGGCGCG TACGGTCCGC TTGGCCCGCT GGGCGGCGAG           9000

GACCCGCAGG GCTTCTCCCC CGACGGTGTT CCCGACCGCA TCATCGCCGA           9050
```

| | |
|---|---|
| GGCCATCCGC CTCAACAATC CGCAGCCGGG CACCGATTAC GACTGGAACC | 9100 |
| GACCGATCAA GCTCGACGAG CCGGGCATCA ACGGTTCCAC CGTGCCGCTG | 9150 |
| CCCTACGGCC TCGACCCGAA GCGGGTTCCG GTCGCGGGTA CGTACTCCAC | 9200 |
| CGAGGCGCAA CAGGAGAGCA GGCTGTCCTC GGCGTGGTAC GAGCTTCCAG | 9250 |
| CCCGCGACGA GACCGAACGG GCTGCGCATC CGCTGGTGGT CATCACCGCC | 9300 |
| GCGGGCACCA TCACCGGCGA GAGCGTCGCC AACGGCCTGA CGACCGGCCA | 9350 |
| GACCGTGGAC CTGGAGTACG CGACCCGCGG CCCGGACGGC ACCCTGGTGC | 9400 |
| CCGCGGGCCG GGTGACACCG TACGACGTGG GGCCCACCCC GTCGTGGCGC | 9450 |
| AACCTGCGCT ACCCGCGCTC GGAGATCCCC GACGATGCCG TCGCGGTGCG | 9500 |
| CGTGGTGGCC GAGGATCTGT CACTGAGCCA GGGCGACTGG ATCGCGGTGA | 9550 |
| CCCCGCCGCG GGTGCCCGAG CTGCAGTCGG TGCAGGAGTA CGTCGGCTCC | 9600 |
| GATCAGCCCG TGCTGATGGA CTGGGCCGTG GGTCTGGCGT TCCCGTGCCA | 9650 |
| GCAGCCCATG CTGCACGCCA ACGGCGTCAC CGAGGTGCCC AAGTTCCGCA | 9700 |
| TCTCGCCGGA CTACTACGCC AAGCTGCAGA GCACCGACAC GTGGCAGGAC | 9750 |
| GGCATCAACG GCGGCCTGCT GGGCATCACC GACCTGCTGC TGCGGGCCTC | 9800 |
| GGTGATGTCG ACCTACCTGT CGCAGGACTG GGGCCAGGAC TGGGGTTCGT | 9850 |
| TGCGCAAGTT CGACACCGTC GTCGAAGCGA CGCCTGCCGA ACTCGATTTC | 9900 |
| GGCTCCCAGA CCCACAGCGG TCTCTACAGC CCGGGGCCTT TGCGCATCCG | 9950 |
| ACCTTGACAT | 9960 |

(2) INFORMATION FOR SEQ ID NO:47:

(i) SEQUENCE CHARACTERISTICS:
        (A) LENGTH: 12
        (B) TYPE: nucleic acid
        (C) STRANDEDNESS: single
        (D) TOPOLOGY: linear (ii) MOLECULE TYPE: other nucleic acid (iii) HYPOTHETICAL: NO (xi) SEQUENCE DESCRIPTION: SEQ ID NO: 47:

| | |
|---|---|
| TGGGCATGGC CC | 12 |

(2) INFORMATION FOR SEQ ID NO:48:

(i) SEQUENCE CHARACTERISTICS:
        (A) LENGTH: 12
        (B) TYPE: nucleic acid
        (C) STRANDEDNESS: single
        (D) TOPOLOGY: linear (ii) MOLECULE TYPE: other nucleic acid (iii) HYPOTHETICAL: NO (xi) SEQUENCE DESCRIPTION: SEQ ID NO: 48:

| | |
|---|---|
| TGGGCGTGGC CC | 12 |

(2) INFORMATION FOR SEQ ID NO:49:

(i) SEQUENCE CHARACTERISTICS:
        (A) LENGTH: 12
        (B) TYPE: nucleic acid
        (C) STRANDEDNESS: single
        (D) TOPOLOGY: linear

```
    (ii) MOLECULE TYPE: other nucleic acid (iii) HYPOTHETICAL: NO (xi) SEQUENCE DESCRIPTION: SEQ ID NO: 49:

TGGGCCTGGC CC                                                        12

(2) INFORMATION FOR SEQ ID NO:50:

(i) SEQUENCE CHARACTERISTICS:
        (A) LENGTH: 12
        (B) TYPE: nucleic acid
        (C) STRANDEDNESS: single
        (D) TOPOLOGY: linear (ii) MOLECULE TYPE: other nucleic acid (iii) HYPOTHETICAL: NO (xi) SEQUENCE DESCRIPTION: SEQ ID NO: 50:

TGGGCATAGC CC                                                        12

(2) INFORMATION FOR SEQ ID NO:51:

(i) SEQUENCE CHARACTERISTICS:
        (A) LENGTH: 12
        (B) TYPE: nucleic acid
        (C) STRANDEDNESS: single
        (D) TOPOLOGY: linear (ii) MOLECULE TYPE: other nucleic acid (iii) HYPOTHETICAL: NO (xi) SEQUENCE DESCRIPTION: SEQ ID NO: 51:

TGGGCATTGC CC                                                        12

(2) INFORMATION FOR SEQ ID NO:52:

(i) SEQUENCE CHARACTERISTICS:
        (A) LENGTH: 12
        (B) TYPE: nucleic acid
        (C) STRANDEDNESS: single
        (D) TOPOLOGY: linear (ii) MOLECULE TYPE: other nucleic acid (iii) HYPOTHETICAL: NO (xi) SEQUENCE DESCRIPTION: SEQ ID NO: 52:

TGGGCATCGC CC                                                        12

(2) INFORMATION FOR SEQ ID NO:53:

(i) SEQUENCE CHARACTERISTICS:
        (A) LENGTH: 20
        (B) TYPE: nucleic acid
        (C) STRANDEDNESS: single
        (D) TOPOLOGY: linear (ii) MOLECULE TYPE: other nucleic acid (iii) HYPOTHETICAL: NO (xi) SEQUENCE DESCRIPTION: SEQ ID NO: 53:

TCGCCATCAG CGTGCCGAGA                                                20

(2) INFORMATION FOR SEQ ID NO:54:
```

```
        (i) SEQUENCE CHARACTERISTICS:
            (A) LENGTH:  20
            (B) TYPE:  nucleic acid
            (C) STRANDEDNESS:  single
            (D) TOPOLOGY:  linear (ii) MOLECULE TYPE: other nucleic acid (iii) HYPOTHETICAL:  NO (xi) SEQUENCE DESCRIPTION:  SEQ ID NO: 54:

TCTCCTCCAC CGGGAGCAGT                                                         20

(2) INFORMATION FOR SEQ ID NO:55:

(i) SEQUENCE CHARACTERISTICS:
            (A) LENGTH:  20
            (B) TYPE:  nucleic acid
            (C) STRANDEDNESS:  single
            (D) TOPOLOGY:  linear (ii) MOLECULE TYPE: other nucleic acid (iii) HYPOTHETICAL:  NO (xi) SEQUENCE DESCRIPTION:  SEQ ID NO: 55:

GTTGCGCACG ATCACGTCGA                                                         20

(2) INFORMATION FOR SEQ ID NO:56:

(i) SEQUENCE CHARACTERISTICS:
            (A) LENGTH:  20
            (B) TYPE:  nucleic acid
            (C) STRANDEDNESS:  single
            (D) TOPOLOGY:  linear (ii) MOLECULE TYPE: other nucleic acid (iii) HYPOTHETICAL:  NO (xi) SEQUENCE DESCRIPTION:  SEQ ID NO: 56:

CAATTGCCCA GCTCCTCCTC                                                         20

(2) INFORMATION FOR SEQ ID NO:57:

(i) SEQUENCE CHARACTERISTICS:
            (A) LENGTH:  20
            (B) TYPE:  nucleic acid
            (C) STRANDEDNESS:  single
            (D) TOPOLOGY:  linear (ii) MOLECULE TYPE: other nucleic acid (iii) HYPOTHETICAL:  NO (xi) SEQUENCE DESCRIPTION:  SEQ ID NO: 57:

ACAGACTGGC GTCGCTGACA                                                         20
```